(12) United States Patent
Moffat et al.

(10) Patent No.: US 11,220,551 B2
(45) Date of Patent: Jan. 11, 2022

(54) CD133-BINDING AGENTS AND USES THEREOF

(71) Applicants: The Governing Council of the University of Toronto, Toronto (CA); McMaster University, Hamilton (CA)

(72) Inventors: Jason Moffat, Toronto (CA); Jarrett Adams, Toronto (CA); Guohua Pan, Oakville (CA); Sachdev Sidhu, Toronto (CA); Rashida Williams, Mississauga (CA); Xiaoyu Zhang, Toronto (CA); Sheila K. Singh, Hamilton (CA); Parvez Vora, Hamilton (CA); Chitra Venugopal, Burlintong (CA)

(73) Assignees: The Governing Council of the University of Toronto, Toronto (CA); McMaster University, Hamilton (CA)

( * ) Notice: Subject to any disclaimer, the term of this patent is extended or adjusted under 35 U.S.C. 154(b) by 153 days.

(21) Appl. No.: 16/342,807

(22) PCT Filed: Oct. 19, 2017

(86) PCT No.: PCT/CA2017/051245
§ 371 (c)(1),
(2) Date: Apr. 17, 2019

(87) PCT Pub. No.: WO2018/072025
PCT Pub. Date: Apr. 26, 2018

(65) Prior Publication Data
US 2019/0330362 A1 Oct. 31, 2019

Related U.S. Application Data

(60) Provisional application No. 62/410,162, filed on Oct. 19, 2016, provisional application No. 62/472,209, filed on Mar. 16, 2017.

(51) Int. Cl.
| | | |
|---|---|---|
| A61K 39/00 | (2006.01) | |
| C07K 16/28 | (2006.01) | |
| A61K 47/68 | (2017.01) | |
| A61P 35/04 | (2006.01) | |
| A61P 35/00 | (2006.01) | |
| A61K 35/17 | (2015.01) | |
| C07K 14/725 | (2006.01) | |
| C07K 14/705 | (2006.01) | |
| C07K 16/46 | (2006.01) | |
| G01N 33/574 | (2006.01) | |

(52) U.S. Cl.
CPC .......... *C07K 16/2896* (2013.01); *A61K 35/17* (2013.01); *A61K 47/6849* (2017.08); *A61P 35/00* (2018.01); *A61P 35/04* (2018.01); *C07K 14/7051* (2013.01); *C07K 14/70517* (2013.01); *C07K 14/70521* (2013.01); *C07K 16/2809* (2013.01); *C07K 16/468* (2013.01); *G01N 33/57407* (2013.01); *A61K 2039/505* (2013.01); *C07K 2317/21* (2013.01); *C07K 2317/31* (2013.01); *C07K 2317/33* (2013.01); *C07K 2317/52* (2013.01); *C07K 2317/55* (2013.01); *C07K 2317/565* (2013.01); *C07K 2317/567* (2013.01); *C07K 2317/622* (2013.01); *C07K 2317/92* (2013.01); *C07K 2319/02* (2013.01); *C07K 2319/30* (2013.01)

(58) Field of Classification Search
CPC ................................. A61K 2039/505
See application file for complete search history.

(56) References Cited

U.S. PATENT DOCUMENTS

2011/0004952 A1* 1/2011 Bosio .................. C07K 14/705
800/13

FOREIGN PATENT DOCUMENTS

| EP | 2769989 A1 | 8/2014 |
| WO | 2016/154623 A2 | 9/2016 |

OTHER PUBLICATIONS

Bao et al.: "Glioma stem cells promote radioresistance by preferential activation of the DNA damage response", Dec. 7, 2006, Nature, vol. 444, pp. 756-760.
Vora, P. et al.: "IMST-53. The Efficacy of CD133 BiTEs and CAR-T Cells in Preclinical Model of Recurrent Glioblastoma", Nov. 2016, Article in Neuro-Oncology; vol. 18(6): vi98.
Evans et al.: "Design of nonpeptidal ligands for a peptide receptor: cholecystokinin antagonists", Jul. 1987, J. Med. Chem., vol. 30(7), pp. 1229-1239.
Fauchere: "Discovery and optimization of pseudopeptide leads towards peptidomimetic drugs", Nov. 1995, Letters in Peptide Science, vol. 2, pp. 115-120.
Ferrandina et al.: "Targeting CD133 antigen in cancer", published online Jun. 17, 2009, Expert Opinion on Therapeutic Targets, vol. 13, issue 7, pp. 823-837.
Vora, P. et al.: "Abstract 3758: The efficacy of CD 133 BiTEs and CAR-T cells in preclinical model of glioblastoma", Jul. 2017, Cancer Research, Proceedings: AACR Annual Meeting Apr. 1-5, 2017, vol. 77 , Issue 13 Supplement.

(Continued)

*Primary Examiner* — Stephen L Rawlings
(74) *Attorney, Agent, or Firm* — Melanie Szweras; Ainslie Parsons; Bereskin & Parr LLP/S.E.N.C.R.L., s.r.l.

(57) ABSTRACT

This disclosure is directed to novel CD133-binding agents. The disclosure is also directed to uses of novel CD133-binding agents for detecting CD133-expressing cells and/or quantitating levels of cellular CD133 expression, for targeting CD133-expressing cells, for decreasing levels of CD133 in CD133-expressing cells and for treating or preventing cancer.

27 Claims, 32 Drawing Sheets
Specification includes a Sequence Listing.

(56) References Cited

OTHER PUBLICATIONS

Gershoni J. et al.: "Epitope mapping—The first step in developing epitope-based vaccines", Biodrugs, ADIS International LTD, NZ, Jan. 1, 2007, vol. 21, No. 3, pp. 145-156.

Extended European Search Report, received in connection to copending European Patent Application No. 17863201.4, dated Mar. 26, 2020.

Kostelny et al.: "Formation of a bispecific antibody by the use of leucine zippers", Mar. 1, 1992, J. Immunol; vol. 148, No. 5, pp. 1547-1553.

Kozbor et al.: "The production of monoclonal antibodies from human lymphocytes", Mar. 1983, Immunology Today, vol. 4, issue 3, pp. 72-79.

Lam: "Application of combinatorial library methods in cancer research and drug discovery", Mini Review, Apr. 1997, Anti-Cancer Drug Design, vol. 12, issue 3, pp. 145-167.

Malmqvist M.: "Biospecific interaction analysis using biosensor technology", Jan. 14, 1993, Nature, vol. 361, pp. 186-187.

Shopes: "A genetically engineered human IgG mutant with enhanced cytolytic activity", May 1, 1992, The Journal of Immunology, vol. 148, Issue 9, pp. 2918-2922.

Veber et al.: "The design of metabolically-stable peptide analogs", Sep. 1985, TINS, Reviews, vol. 8, pp. 392-396.

Wilkinson D: "Ultimate abs—Immunochemical techniques inspire development of new antibody purification methods", Apr. 2000, The Scientist Magazine, pp. 1-13.

Winter et al.: "Humanized antibodies", May 1993, TiPS, vol. 14, issue 5, pp. 139-143.

Williams, R.: "Generation of Anti-CD133 Human Synthetic Antibodies as Tools for Exploring CD133 Function", Nov. 12, 2013, Department of Molecular Genetics, University of Toronto, p. 1-65.

Vora, P. et al.: Abstract No. B079: "The efficacy of CD133 BiTEs and CAR-T cells in preclinical model of recurrent glioblastoma", Nov. 2016; Cancer Immunol Res 2016; vol. 4 Issue 11 Supplement.

Vora, P. et al.: Abstract 1481: "Preclinical validation of a novel CD133/CD3 bispecific T-cell engager (BiTE) antibody to target patient-derived glioblastoma cells". Cancer Res, vol. 76, issue 14 Supplement, Proceedings: AACR 107th Annual Meeting 2016; April 16-26; New Orleans; published Jul. 2016.

Bostad, M. et al.: "Light-controlled endosomal escape of the novel CD133-targeting immunotoxin AC133-saporin by photochemical internalization—A minimally invasive cancer stem cell-targeting strategy", Available online Mar. 7, 2015, Journal of Controlled Release, vol. 206, pp. 37-48.

Vora, P. et al.: "Abstract 1481: Preclinical validation of a novel CD133/CD3 bispecific T-cell engager (BiTE) antibody to target patient-derived glioblastoma cells", published Jul. 2016; Proceedings: AACR 107th Annual Meeting Apr. 16-20, 2016; vol. 76, Issue 14 Supplement.

Vora, P. et al.: Poster: Preclinical validation of a novel CD133/CD3 bispecific T-cell engager (BiTE) antibody to target patient-derived glioblastoma cells, Proceedings: AACR 107th Annual Meeting Apr. 16-20, 2016.

Vora, P. et al.: "Abstract 2300: Human CD133-specific chimeric antigen receptor (CAR) modified T cells target patient-derived glioblastoma brain tumors" published Jul. 2016, Proceedings: AACR 107th Annual Meeting Apr. 16-20, 2016.

Vora, P. et al.: Poster: Human CD133-specific chimeric antigen receptor (CAR) modified T cells target patient-derived glioblastoma brain tumors, Proceedings: AACR 107th Annual Meeting Apr. 16-20, 2016.

Abate-Daga et al.: "CAR models: next-generation CAR modifications for enhanced T-cell formation", Molecular Therapy—Oncolytics, published online May 18, 2016, vol. 3, 16014.

Altschul et al.: "Gapped BLAST and PSI-BLAST: a new generation of protein database search programs", published Sep. 1, 1997, Nucleic Acids Res , vol. 25, pp. 3389-3402.

Boman et al.: "Cancer Stem Cells: A Step Toward the Cure", published Jun. 10, 2008, J. Clin. Oncol., vol. 26, No. 17, pp. 2795-2799.

Brown et al.: "Regression of Glioblastoma after Chimeric Antigen Receptor T-Cell Therapy", Dec. 29, 2016, N Engl J Med , vol. 375(26):2561-2569.

Caron et al.: "Engineered Humanized Dimeric Forms of IgG Are More Effective Antibodies", Oct. 1992, J Exp Med., vol. 176(4), pp. 1191-1195.

Choi, et al.: "Human regulatory T cells kill tumor cells through granzyme-dependent cytotoxicity upon retargeting with a bispecific antibody", Sep. 2013, Cancer Immunology Research, vol. 1(3), pp. 163-167.

Collins et al.: "Prospective identification of tumorigenic prostate cancer stem cells", Dec. 1, 2005. Cancer res 2005, vol. 65(23), pp. 10946-10951.

Cote et al.: "Generation of human monoclonal antibodies reactive with cellular antigens", Apr. 1983. Proc. Natl. Acad. Sci. USA, vol. 80, pp. 2026-2030, Immunology.

Davies et al.: "Antibody-Antigen Complexes", 1990. Annual Rev. Biochem., Jul. 1990, vol. 59, pp. 439-473.

Evangelista et al.: "The hedgehog signaling pathway in cancer", Oct. 15, 2006, Clin. Cancer Res., vol. 12(20), pp. 5924-5928.

Wang et al.: "Clinical manufacturing of CAR T cells: foundation of a promising therapy", Jun. 15, 2016, Molecular Therapy—Oncolytics, vol. 3, 16015.

Hermann et al.: "Distinct populations of cancer stem cells determine tumor growth and metastatic activity in human pancreatic cancer", Sep. 12, 2007, Cell Stem Cell, vol. 1, pp. 313-323.

Holliger et al.: ""Diabodies"—: Small bivalent and bispecific antibody fragments", Jul. 1993, Proc. Natl. Acad. Sci. USA, vol. 90, No. 14, pp. 6444-6448, Biophysics.

Karlin et al.: Methods for assessing the statistical significance of molecular sequence features by using general scoring schemes, Mar. 1990 Proc. Natl. Acad Sci. U S A , vol. 87, pp. 2264-2268; Evolution.

Karlin et al.: "Applications and Statistics for multiple high-scoring segments in molecular sequences", Jun. 1993. Proc. Natl. Acad. Sci. U.S.A. vol. 90, pp. 5873-5877, Evolution.

Lefranc et al.: "IMGT unique numbering for immunoglobulin and T cell receptor variable domains and Ig superfamily V-like domains", Jan. 2003. Developmental and Comparative Immunology, vol. 27, Issue 1, pp. 55-77.

Liu et al. "Chimeric mouse-human IgG1 antibody that can mediate lysis of cancer cells", May 1987, Proc. Natl. Acad. Sci U.S A., vol. 84, pp. 3439-3443.

Wei et al.: "Cancer stem-like cells in human prostate carcinoma cells DU145: the seeds of the cell line?", published online May 30, 2007, Cancer Biology & Therapy, vol. 6, issue 5, pp. e1-e6.

Lugli et al.: "Prognostic impact of the expression of putative cancer stem cell markers CD133, CD166, CD44s, EpCAM, and ALDH1 in colorectal cancer", published online Jul. 6, 2010, British Journal of Cancer, vol. 103, pp. 382-390.

Mak et al.: "Regulation of CD133 by HDAC6 Promotes β-Catenin Signaling to Suppress Cancer Cell Differentiation", Oct. 25, 2012, Cell Reports Article, vol. 2, pp. 951-963.

Mak et al.: "The Mixed Lineage Leukemia (MLL) Fusion-Associated Gene AF4 Promotes CD133 Transcription", published first online Feb. 14, 2012, Cancer research, vol. 72(8), pp. 1929-1934.

Maus et al.: "Making better chimeric antigen receptors for adoptive T-cell therapy", Apr. 15, 2016, Clin Cancer Res., vol. 22(8), pp. 1875-1884.

McEnaney et al.: "Chemically synthesized molecules with the targeting and effector functions of antibodies", Dec. 16, 2014, J Am Chem Soc., vol. 136, pp. 18034-18043.

Miki et al.: "Identification of Putative Stem Cell Markers, CD133 and CXCR4, in hTERT—Immortalized Primary Nonmalignant and Malignant Tumor-Derived Human Prostate Epithelial Cell Lines and in Prostate Cancer Specimens", Apr. 1, 2007, Cancer research, vol. 67, pp. 3153-3161.

Missol-Kolka et al. "Prominin-1 (CD133) is not restricted to stem cells located in the basal compartment of murine and human

(56) References Cited

OTHER PUBLICATIONS prostate", first published online in Willey Online Library, Aug. 17, 2010, The Prostate, vol. 71, Issue 3, pp. 254-267.
Moriyama et al.: "Enhanced cell migration and invasion of CD133+ pancreatic cancer cells cocultured with pancreatic stromal cells", Original article, published online Apr. 28, 2010, Cancer, vol. 116, Issue 14, pp. 3357-3368.
Myers et al.: "Optimal alignments in linear space", Mar. 1, 1988. CABIOS, vol. 4, No. 1, pp. 11-17.
O'Brien et al.: "A human colon cancer cell capable of initiating tumour growth in immunodeficient mice", Nov. 19, 2006. Nature, vol. 445, pp. 106-110.
Parashar: "Aptamers in Therapeutics", Jun. 1, 2016, Journal of Clinical and Diagnostic Research, vol. 10(6): BE01-BE06.
Pfeiffer et al.: "Stem cell characteristics in prostate cancer cell lines", Published online ahead of print on Jan. 19, 2009, European Urology, vol. 57, pp. 246-255.
Prasad et al.: "Effective Eradication of Glioblastoma Stem Cells by Local Application of an AC133/CD133-Specific T-cell-Engaging Antibody and CD8 T Cells", Jun. 1, 2015 Cancer Research, vol. 75, issue 11, pp. 2166-2176.
Rappa et al.: "The stem cell-associated antigen CD133 (Prominin-1) is a molecular therapeutic target for metastatic melanoma", first published online in Stem cells Express Sep. 18, 2008, vol. 26, pp. 3008-3017.
Zhong et al.: "Clinicopathological significance and prognostic value of the expression of the cancer stem cell marker CD133 in hepatocellular carcinoma: a meta-analysis", published online Apr. 29, 2015, Tumor Biol., Research article, vol. 36, pp. 7623-7630.
Reverdatto et al.: "Peptide aptamers: development and applications", Apr. 2015, Curr Top Med Chem., vol. 15 (12), pp. 1082-1101.
Ricci-Vitiani et al.: "Identification and expansion of human colon-cancer-initiating cells", online publication Nov. 19, 2006, Nature, vol. 445(7123), pp. 111-115.
Rizo et al.: "Constrained peptides: models of bioactive peptides and protein substructures", volume publication Jul. 1992, Ann Rev Biochem., vol. 61, pp. 387-416.
Schmohl et al.: "CD133, Selectively Targeting the Root of Cancer", May 28, 2016, Toxins (Basel), vol. 8, 165, pp. 1-19.

Shmelkov: "Alternative promoters regulate transcription of the gene that encodes stem cell surface protein AC133", Apr. 2004, Article, Blood, vol. 103, No. 6, pp. 2055-2061.
Singh et al.: "Identification of a cancer stem cell in human brain tumors", Sep. 15, 2003, Cancer Res., vol. 63; pp. 5821-5828.
Singh et al.: "Identification of human brain tumour initiating cells", Nov. 18, 2004, Nature; vol. 432, pp. 396-401.
Smith et al.: "CD133/prominin-1 is a potential therapeutic target for antibody-drug conjugates in hepatocellular and gastric cancers", published online Jun. 10, 2008, British journal of cancer, vol. 99, pp. 100-109.
Takenobu et al.: "CD133 suppresses neuroblastoma cell differentiation via signal pathway modification", Jan. 2011, Oncogene, vol. 30, pp. 97-105.
Traunecker et al.: "Bispecific single chain molecules (Janusins) target cytotoxic lymphocytes on HIV infected cells" Dec. 1991, The EMBO Journal, vol. 10; pp. 3655-3659.
Tutt et al.: "Trispecific F (ab') 3 derivatives that use cooperative signaling via the TCR/CD3 complex and CD2 to activate and redirect resting cytotoxic T cells", Jul. 1, 1991, The Journal of Immunology, vol. 147, pp. 60-69.
Ulasov et al.: "Inhibition of Sonic hedgehog and Notch pathways enhances sensitivity of CD133+ glioma stem cells to temozolomide therapy", Jan.-Feb. 2011, Mol. Med., vol. 17(1-2), pp. 103-112.
Venugopal et al.: "Pyrvinium targets CD133 in human glioblastoma brain tumor-initiating cells", published OnlineFirst Jul. 7, 2015, Clinical cancer research: an official journal of the American Association for Cancer Research, vol. 21(23), pp. 5324-5337.
Vincke et al.: "General strategy to humanize a camelid single-domain antibody and identification of a universal humanized nanobody scaffold", Jan. 30, 2009; the Journal of Biological Chemistry, vol. 284(5), pp. 3273-3284.
Horst et al.: "The cancer stem cell marker CDI33 has high prognostic impact but unknown functional relevance for the metastasis of human colon cancer", Journal of Pathology, published online Jun. 25, 2009 in Wiley InterScience, vol. 219: pp. 427-434.
Bauer et al.: New Insights Into the Cell Biology of Hematopoietic Progenitors by Studying Prominin-1 (CD133), Cells Tissues Organs, published online Dec. 21, 2007, vol. 188: pp. 127-138.

* cited by examiner

FIGURE 1A

Library F

| CD133 | HEK293 | CD133 | HEK293 | CD133 | HEK293 | CD133 | HEK293 | CD133 | HEK293 | CD133 | HEK293 |
|---|---|---|---|---|---|---|---|---|---|---|---|
| 1.797 | 0.93 | 1.666 | 0.958 | 0.956 | 0.822 | 1.639 | 0.934 | 1.576 | 0.948 | 1.644 | 0.848 |
| 1.704 | 0.947 | 1.685 | 0.875 | 0.875 | 0.905 | 1.64 | 0.771 | 1.668 | 0.845 | 1.681 | 0.834 |
| 1.739 | 0.83 | 1.579 | 0.808 | 0.808 | 0.811 | 1.611 | 0.875 | 1.609 | 0.714 | 1.609 | 0.652 |
| 1.788 | 0.933 | 1.65 | 0.838 | 0.838 | 0.841 | 1.572 | 0.734 | 1.541 | 0.744 | 1.642 | 0.663 |
| 1.778 | 0.824 | 1.663 | 0.638 | 0.638 | 0.751 | 1.498 | 0.718 | 1.426 | 0.715 | 1.54 | 0.706 |
| 1.759 | 0.787 | 1.471 | 0.84 | 0.64 | 1.303 | 1.605 | 0.688 | 0.948 | 0.674 | 1.463 | 0.587 |
| 1.744 | 0.802 | 1.808 | 0.831 | 0.831 | 0.853 | 1.529 | 0.706 | 1.701 | 0.77 | 1.62 | 0.71 |
| 1.621 | 0.765 | 1.153 | 0.465 | 0.465 | 0.666 | 1.692 | 0.793 | 1.602 | 0.729 | 1.56 | 0.66 |

| CD133 | HEK293 | CD133 | HEK293 | CD133 | HEK293 | CD133 | HEK293 | CD133 | HEK293 | CD133 | HEK293 |
|---|---|---|---|---|---|---|---|---|---|---|---|
| 1.642 | 0.746 | 1.62 | 0.903 | 1.474 | 0.778 | 1.584 | 0.873 | 1.52 | 1.011 | 1.603 | 0.685 |
| 1.551 | 0.76 | 1.628 | 0.787 | 1.568 | 0.777 | 1.588 | 0.845 | 1.52 | 0.856 | 1.615 | 0.87 |
| 1.513 | 0.676 | 1.561 | 0.734 | 1.573 | 0.821 | 1.62 | 0.859 | 1.565 | 0.927 | 1.223 | 1.049 |
| 1.545 | 0.729 | 1.51 | 0.732 | 1.564 | 0.735 | 1.666 | 0.777 | 1.502 | 0.735 | 1.673 | 0.725 |
| 1.495 | 0.686 | 1.592 | 0.639 | 1.545 | 0.718 | 1.551 | 0.665 | 1.621 | 0.73 | 1.531 | 0.674 |
| 1.596 | 0.704 | 1.501 | 0.682 | 1.568 | 0.72 | 1.563 | 0.713 | 1.608 | 0.812 | 1.568 | 0.678 |
| 1.634 | 0.743 | 1.538 | 0.814 | 1.601 | 0.68 | 1.527 | 0.762 | 1.705 | 0.757 | 1.697 | 0.716 |
| 1.592 | 0.699 | 1.674 | 0.656 | 1.464 | 0.658 | 1.505 | 0.639 | 1.701 | 0.687 | 0.191 | 0.161 |

Library G

| CD133 | HEK293 | CD133 | HEK293 | CD133 | HEK293 | CD133 | HEK293 | CD133 | HEK293 | CD133 | HEK293 |
|---|---|---|---|---|---|---|---|---|---|---|---|
| 0.6 | 0.411 | 0.44 | 0.355 | 0.365 | 0.335 | 0.369 | 0.325 | 0.334 | 0.259 | 0.456 | 0.354 |
| 0.405 | 0.424 | 0.537 | 0.518 | 0.477 | 0.377 | 0.405 | 0.334 | 0.301 | 0.248 | 0.313 | 0.257 |
| 0.36 | 0.339 | 0.422 | 0.331 | 0.291 | 0.257 | 0.317 | 0.245 | 0.376 | 0.268 | 0.384 | 0.26 |
| 0.304 | 0.338 | 0.253 | 0.236 | 0.411 | 0.3 | 0.235 | 0.223 | 0.337 | 0.258 | 0.351 | 0.302 |
| 0.236 | 0.265 | 0.301 | 0.319 | 0.353 | 0.292 | 0.331 | 0.289 | 0.331 | 0.287 | 0.294 | 0.242 |
| 0.226 | 0.259 | 0.207 | 0.236 | 0.311 | 0.267 | 0.443 | 0.388 | 0.214 | 0.2 | 0.301 | 0.269 |
| 0.248 | 0.261 | 0.334 | 0.304 | 0.459 | 0.309 | 0.311 | 0.245 | 0.235 | 0.223 | 0.274 | 0.224 |
| 0.248 | 0.183 | 0.239 | 0.203 | 0.369 | 0.241 | 0.232 | 0.176 | 0.243 | 0.163 | 0.244 | 0.175 |

| CD133 | HEK293 | CD133 | HEK293 | CD133 | HEK293 | CD133 | HEK293 | CD133 | HEK293 | CD133 | HEK293 |
|---|---|---|---|---|---|---|---|---|---|---|---|
| 0.378 | 0.359 | 0.307 | 0.265 | 0.661 | 0.639 | 0.341 | 0.312 | 0.424 | 0.477 | 0.311 | 0.295 |
| 0.321 | 0.237 | 0.42 | 0.338 | 0.443 | 0.303 | 0.435 | 0.364 | 0.319 | 0.328 | 0.456 | 0.416 |
| 0.288 | 0.207 | 0.293 | 0.234 | 0.364 | 0.275 | 0.562 | 0.42 | 0.359 | 0.273 | 0.355 | 0.374 |
| 0.268 | 0.244 | 0.32 | 0.354 | 0.525 | 0.33 | 0.335 | 0.262 | 0.489 | 0.345 | 0.279 | 0.227 |
| 0.342 | 0.332 | 0.305 | 0.277 | 0.259 | 0.235 | 0.288 | 0.24 | 0.241 | 0.223 | 0.252 | 0.215 |
| 0.258 | 0.201 | 0.314 | 0.303 | 0.322 | 0.277 | 0.262 | 0.222 | 0.356 | 0.313 | 0.313 | 0.228 |
| 0.369 | 0.267 | 0.457 | 0.51 | 0.276 | 0.2 | 0.55 | 0.442 | 0.273 | 0.211 | 0.347 | 0.272 |
| 0.254 | 0.181 | 0.291 | 0.196 | 0.22 | 0.166 | 0.512 | 0.345 | 0.326 | 0.239 | 0.186 | 0.168 | a.

b.

BiTE #1

BiTE #2

FIGURE 11A con't
BiTE #1
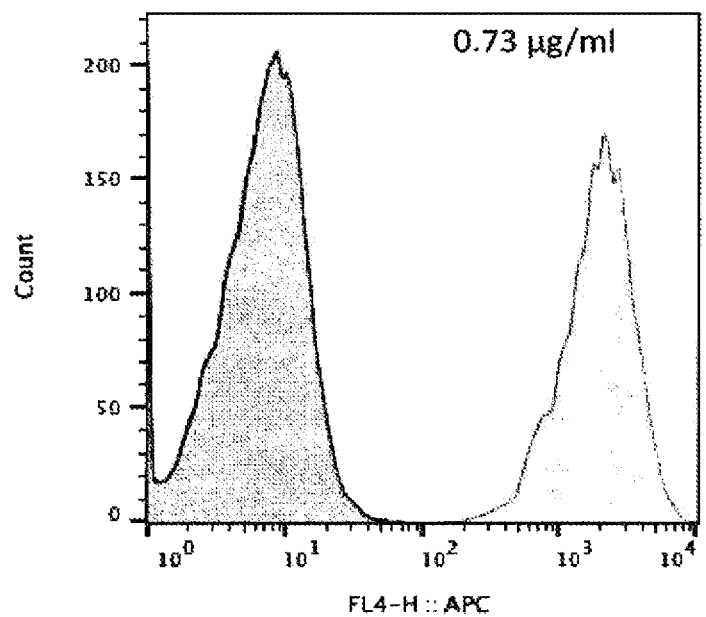
BiTE #2
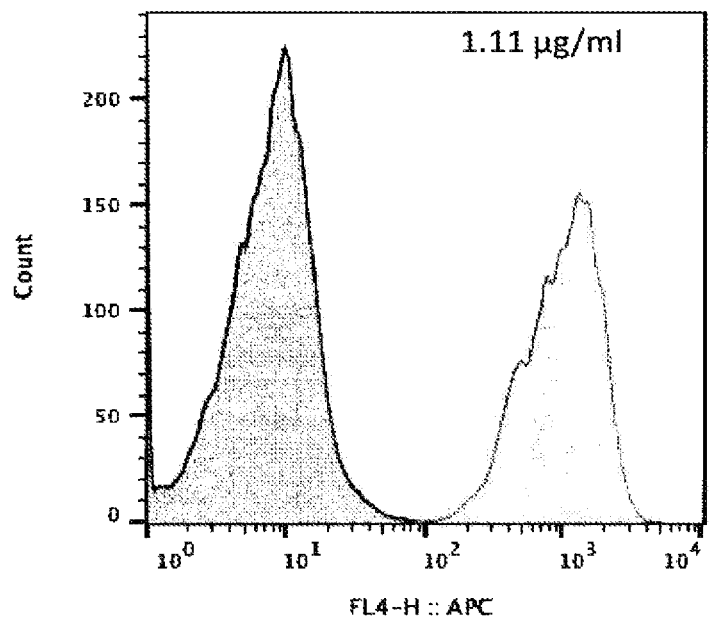

FIGURE 11A con't
BiTE #1
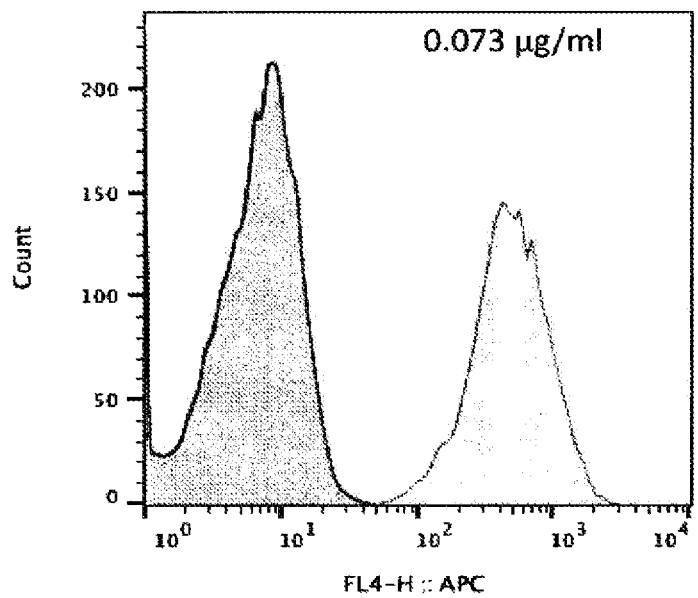
BiTE #2
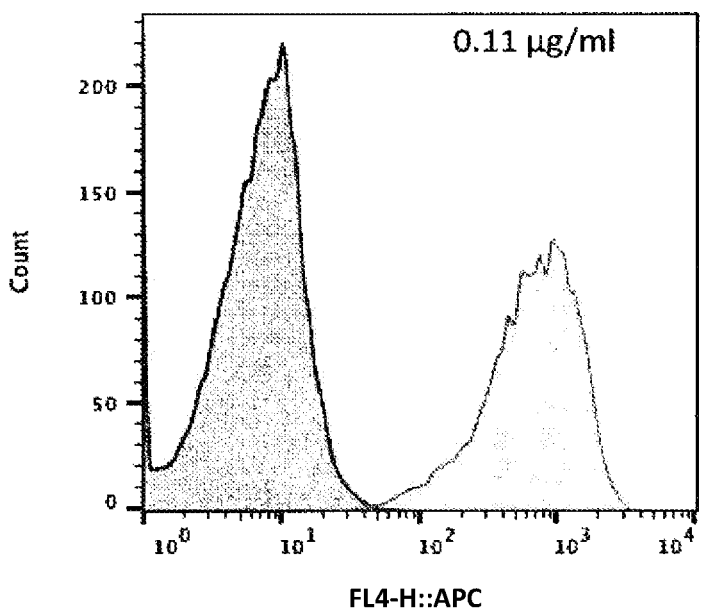

FIGURE 11B con't
BiTE #3
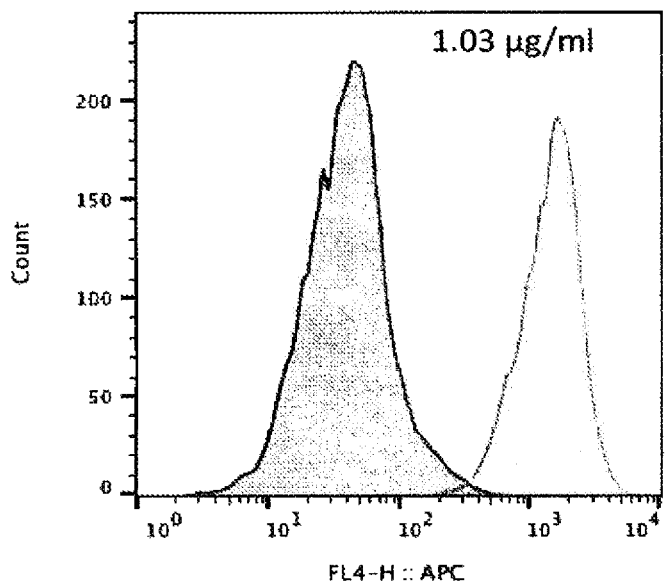
BiTE #4
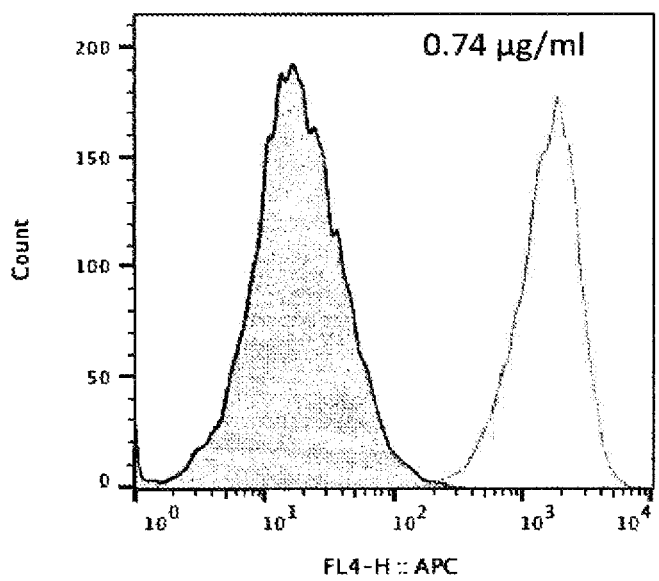

FIGURE 11B con't
BiTE #3
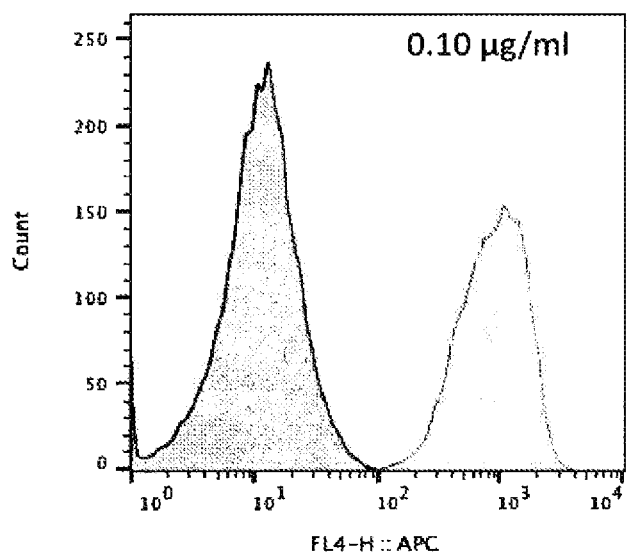
BiTE #4
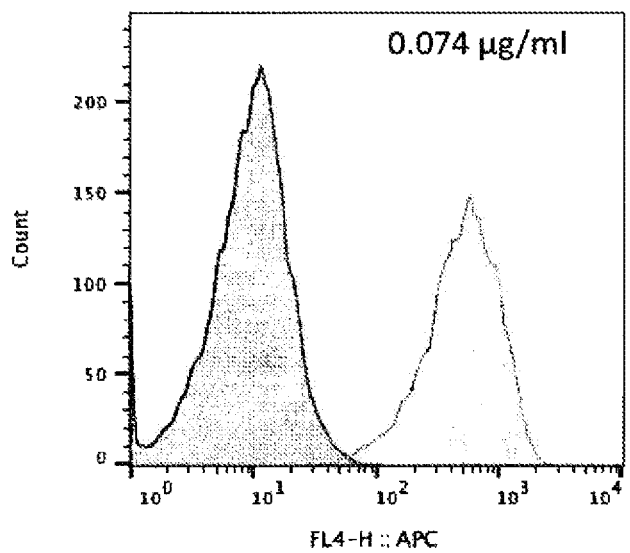

E:T = 1:1
Time = 18 hours

FIGURE 17 con't
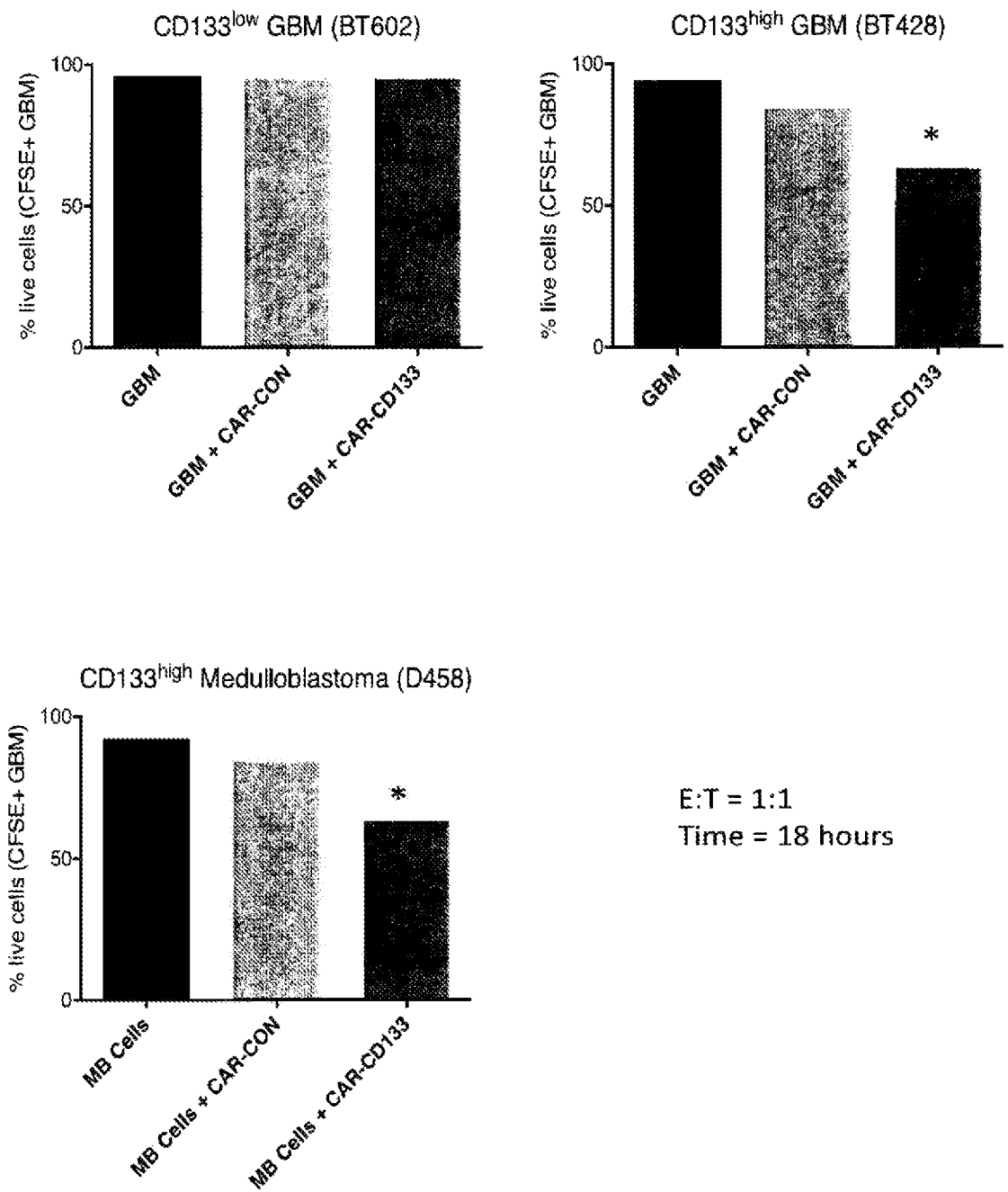

CD133-specific CAR-T

Treatment Delivery: Intracranial
Dose: 1million x 2 doses (2 week)

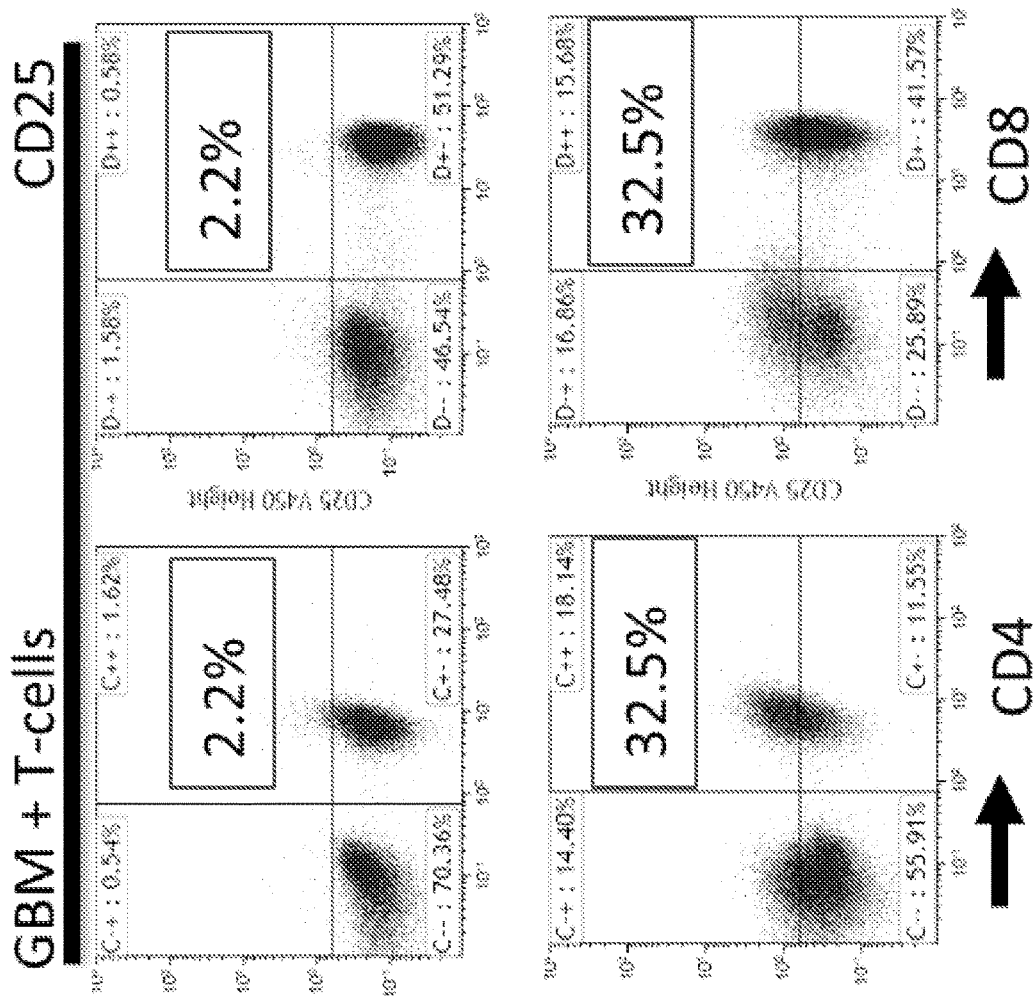
FIGURE 21con't

SEQUENCE LISTING

<160> NUMBER OF SEQ ID NOS: 55

<210> SEQ ID NO 1
<211> LENGTH: 864
<212> TYPE: PRT
<213> ORGANISM: Homo sapiens

<400> SEQUENCE: 1

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285
```

-continued

Ser Ser Leu Thr Ser Val Lys Thr Ser Leu Arg Ser Leu Asn Asp
    290             295             300

Pro Leu Cys Leu Val His Pro Ser Ser Glu Thr Cys Asn Ser Ile Arg
305             310             315             320

Leu Ser Leu Ser Gln Leu Asn Ser Asn Pro Glu Leu Arg Gln Leu Pro
            325             330             335

Pro Val Asp Ala Glu Leu Asp Asn Val Asn Asn Val Leu Arg Thr Asp
            340             345             350

Leu Asp Gly Leu Val Gln Gln Gly Tyr Gln Ser Leu Asn Asp Ile Pro
            355             360             365

Asp Arg Val Gln Arg Gln Thr Thr Thr Val Val Ala Gly Ile Lys Arg
    370             375             380

Val Leu Asn Ser Ile Gly Ser Asp Ile Asp Asn Val Thr Gln Arg Leu
385             390             395             400

Pro Ile Gln Asp Ile Leu Ser Ala Phe Ser Val Tyr Val Asn Asn Thr
                405             410             415

Glu Ser Tyr Ile His Arg Asn Leu Pro Thr Leu Glu Glu Tyr Asp Ser
            420             425             430

Tyr Trp Trp Leu Gly Gly Leu Val Ile Cys Ser Leu Leu Thr Leu Ile
            435             440             445

Val Ile Phe Tyr Tyr Leu Gly Leu Leu Cys Gly Val Cys Gly Tyr Asp
    450             455             460

Arg His Ala Thr Pro Thr Thr Arg Gly Cys Val Ser Asn Thr Gly Gly
465             470             475             480

Val Phe Leu Met Val Gly Val Gly Leu Ser Phe Leu Phe Cys Trp Ile
                485             490             495

Leu Met Ile Ile Val Val Leu Thr Phe Val Phe Gly Ala Asn Val Glu
            500             505             510

Lys Leu Ile Cys Glu Pro Tyr Thr Ser Lys Glu Leu Phe Arg Val Leu
            515             520             525

Asp Thr Pro Tyr Leu Leu Asn Glu Asp Trp Glu Tyr Tyr Leu Ser Gly
    530             535             540

Lys Leu Phe Asn Lys Ser Lys Met Lys Leu Thr Phe Glu Gln Val Tyr
545             550             555             560

Ser Asp Cys Lys Lys Asn Arg Gly Thr Tyr Gly Thr Leu His Leu Gln
                565             570             575

Asn Ser Phe Asn Ile Ser Glu His Leu Asn Ile Asn Glu His Thr Gly
            580             585             590

Ser Ile Ser Ser Glu Leu Glu Ser Leu Lys Val Asn Leu Asn Ile Phe
            595             600             605

Leu Leu Gly Ala Ala Gly Arg Lys Asn Leu Gln Asp Phe Ala Ala Cys
    610             615             620

Gly Ile Asp Arg Met Asn Tyr Asp Ser Tyr Leu Ala Gln Thr Gly Lys
625             630             635             640

Ser Pro Ala Gly Val Asn Leu Leu Ser Phe Ala Tyr Asp Leu Glu Ala
                645             650             655

Lys Ala Asn Ser Leu Pro Pro Gly Asn Leu Arg Asn Ser Leu Lys Arg
            660             665             670

Asp Ala Gln Thr Ile Lys Thr Ile His Gln Gln Arg Val Leu Pro Ile
    675             680             685

Glu Gln Ser Leu Ser Thr Leu Tyr Gln Ser Val Lys Ile Leu Gln Arg
    690             695             700

Thr Gly Asn Gly Leu Leu Glu Arg Val Thr Arg Ile Leu Ser Leu Asp
705                 710                 715                 720

Phe Ala Gln Asn Phe Ile Thr Asn Asn Thr Ser Ser Val Ile Ile Glu
            725                 730                 735

Glu Thr Lys Lys Tyr Gly Arg Thr Ile Ile Gly Tyr Phe Glu His Tyr
            740                 745                 750

Leu Gln Trp Ile Glu Phe Ser Ile Ser Glu Lys Val Ala Ser Cys Lys
            755                 760                 765

Pro Val Ala Thr Ala Leu Asp Thr Ala Val Asp Val Phe Leu Cys Ser
            770                 775                 780

Tyr Ile Ile Asp Pro Leu Asn Leu Phe Trp Phe Gly Ile Gly Lys Ala
785                 790                 795                 800

Thr Val Phe Leu Leu Pro Ala Leu Ile Phe Ala Val Lys Leu Ala Lys
            805                 810                 815

Tyr Tyr Arg Arg Met Asp Ser Glu Asp Val Tyr Asp Val Glu Thr
            820                 825                 830

Ile Pro Met Lys Asn Met Glu Asn Gly Asn Asn Gly Tyr His Lys Asp
            835                 840                 845

His Val Tyr Gly Ile His Asn Pro Val Met Thr Ser Pro Ser Gln His
850                 855                 860

<210> SEQ ID NO 2
<211> LENGTH: 213
<212> TYPE: PRT
<213> ORGANISM: Artificial Sequence
<220> FEATURE:
<223> OTHER INFORMATION: Synthetic construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ser Ser Tyr Val
            20                  25                  30

Ala Trp Tyr Gln Gln Lys Pro Gly Lys Ala Pro Lys Leu Leu Ile Tyr
            35                  40                  45

Ser Ala Ser Tyr Leu Tyr Ser Gly Val Pro Ser Arg Phe Ser Gly Ser
50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Gly Val Trp Ser Leu Ile Thr
            85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 3
<211> LENGTH: 456
<212> TYPE: PRT
<213> ORGANISM: Artificial Sequence
<220> FEATURE:
<223> OTHER INFORMATION: Synthetic construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Tyr
            20                  25                  30

Gly Ser Met His Trp Val Arg Gln Ala Pro Gly Lys Gly Leu Glu Trp
        35                  40                  45

Val Ala Ser Ile Ser Pro Tyr Tyr Gly Ser Thr Tyr Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg His Ala Ser Ser Gly Tyr Gly His Tyr Ala Val Tyr Gly
            100                 105                 110

Ile Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

```
Arg Glu Pro Gln Val Tyr Thr Leu Pro Pro Ser Arg Glu Met Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 4
<211> LENGTH: 216
<212> TYPE: PRT
<213> ORGANISM: Artificial Sequence
<220> FEATURE:
<223> OTHER INFORMATION: Synthetic construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser His Ala Gly His
                85                  90                  95

Leu Phe Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 5
<211> LENGTH: 448
<212> TYPE: PRT
<213> ORGANISM: Artificial Sequence
<220> FEATURE:
```

<223> OTHER INFORMATION: Synthetic construct

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Tyr Ser Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Ser Val Ala Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 6
<211> LENGTH: 5
<212> TYPE: PRT
<213> ORGANISM: Artificial Sequence
<220> FEATURE:
<223> OTHER INFORMATION: Synthetic construct

<400> SEQUENCE: 6

Gln Gly Ser Ser Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic construct

<400> SEQUENCE: 7

Ser Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthetic construct

<400> SEQUENCE: 8

Gln Gln Gly Val Trp Ser Leu Ile Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic construct

<400> SEQUENCE: 9

Gly Phe Asn Ile Tyr Tyr Tyr Gly Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Ile Ser Pro Tyr Tyr Gly Ser Thr
1               5

<210> SEQ ID NO 11
<211> LENGTH: 18
<212> TYPE: PRT
<213> ORGANISM: Artificial Sequence

```
<220> FEATURE:
<223> OTHER INFORMATION: Synthetic construct

<400> SEQUENCE: 11

Ala Arg His Ala Ser Ser Gly Tyr Gly His Tyr Ala Val Tyr Gly Ile
1               5                   10                  15
Asp Tyr

<210> SEQ ID NO 12
<211> LENGTH: 6
<212> TYPE: PRT
<213> ORGANISM: Artificial Sequence
<220> FEATURE:
<223> OTHER INFORMATION: Synthetic construct

<400> SEQUENCE: 12

Gln Ser Val Ser Ser Ala
1               5

<210> SEQ ID NO 13
<211> LENGTH: 3
<212> TYPE: PRT
<213> ORGANISM: Artificial Sequence
<220> FEATURE:
<223> OTHER INFORMATION: Synthetic construct

<400> SEQUENCE: 13

Ser Ala Ser
1

<210> SEQ ID NO 14
<211> LENGTH: 11
<212> TYPE: PRT
<213> ORGANISM: Artificial Sequence
<220> FEATURE:
<223> OTHER INFORMATION: Synthetic construct

<400> SEQUENCE: 14

Gln Gln Tyr Ser His Ala Gly His Leu Phe Thr
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic construct

<400> SEQUENCE: 15

Gly Phe Asn Leu Ser Ser Ser Ser
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic construct

<400> SEQUENCE: 16

Ile Tyr Pro Tyr Tyr Ser Tyr Thr
1               5

<210> SEQ ID NO 17
<211> LENGTH: 11
<212> TYPE: PRT
```

```
<213> ORGANISM: Artificial Sequence
<220> FEATURE:
<223> OTHER INFORMATION: Synthetic construct

<400> SEQUENCE: 17

Ala Arg Phe Gly Ser Val Ala Gly Phe Asp Tyr
1               5                   10

<210> SEQ ID NO 18
<211> LENGTH: 644
<212> TYPE: DNA
<213> ORGANISM: Artificial Sequence
<220> FEATURE:
<223> OTHER INFORMATION: Synthetic construct

<400> SEQUENCE: 18
gatatccaga tgacccagtc cccgagctcc ctgtccgcct ctgtgggcga tagggtcacc      60
atcacctgcc gtgccagtca gggttcttct tacgtagcct ggtatcaaca gaaaccagga    120
aaagctccga agcttctgat ttactctgca tcctacctct actctactct ggagtccctt    180
ctcgcttctc tggtagccgt tccgggacgg atttcactct gaccatcagc agtctgcagc    240
cggaagactt cgcaacttat tactgtcagc aaggtgtttg gtctctgatc acgttcggac    300
agggtaccaa ggtggagatc aaacgtacgg tggctgcacc atctgtcttc atcttcccgc    360
catctgatga gcagttgaaa tctggaactg cctctgttgt gtgcctgctg aataacttct    420
atcccagaga ggccaaagta cagtggaagg tggataacgc cctccaatcg ggtaactccc    480
aggagagtgt cacagagcag gacagcaagg acagcaccta cagcctcagc agcaccctga    540
cgctgagcaa agcagactac gagaaacaca agtctacgc ctgcgaagtc acccatcagg    600
gcctgagctc gcccgtcaca aagagcttca cagggagga gtgt                      644

<210> SEQ ID NO 19
<211> LENGTH: 1368
<212> TYPE: DNA
<213> ORGANISM: Artificial Sequence
<220> FEATURE:
<223> OTHER INFORMATION: Synthetic construct

<400> SEQUENCE: 19
gaggttcagc tggtggagtc tggcggtggc ctggtgcagc caggggctc actccgtttg       60 tcctgtgcag cttctggctt caacatctac tactacggtt ctatgcactg ggtgcgtcag    120
gccccgggta agggcctgga atgggttgca tctatttctc cttactacgg ctctacttac    180
tatgccgata gcgtcaaggg ccgtttcact ataagcgcag acacatccaa aaacacagcc    240
tacctacaaa tgaacagctt aagagctgag gacactgccg tctattattg tgctcgccat    300
gcttcttctg gttacggtca ttacgctgtt tacggtattg actactgggg tcaaggaacc    360
ctggtcaccg tctcctcggc tagcaccaag ggcccatcgg tcttcccct ggcaccctcc    420 tccaagagca cctctggggg cacagcggcc ctgggctgcc tggtcaagga ctacttcccc    480
gaaccggtga cggtgtcgtg gaactcaggc gccctgacca gcggcgtgca ccttcccg    540 gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
```

```
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggaggagat gaccaagaac caggtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct cctctacag caagctcacc    1260 gtggacaaga gcaggtggca gcaggggaac gtcttctcat gctccgtgat gcatgaggct   1320
ctgcacaacc actacacgca gaagagcctc tccctgtctc cgggtaaa                1368
```

<210> SEQ ID NO 20
<211> LENGTH: 653
<212> TYPE: DNA
<213> ORGANISM: Artificial Sequence
<220> FEATURE:
<223> OTHER INFORMATION: Synthetic construct

<400> SEQUENCE: 20

```
gatatccaga tgacccagtc cccgagctcc ctgtccgcct ctgtgggcga tagggtcacc     60
atcacctgcc gtgccagtca gtccgtgtcc agcgctgtag cctggtatca acagaaacca    120
ggaaaagctc cgaagcttct gatttactcg gcatccagcc tctactctac tctggagtcc    180
cttctcgctt ctctggtagc cgttccggga cggatttcac tctgaccatc agcagtctgc    240
agccggaaga cttcgcaact tattactgtc agcaatactc tcatgctggt catctgttca    300
cgttcggaca gggtaccaag gtggagatca aacgtacggt ggctgcacca tctgtcttca    360
tcttcccgcc atctgatgag cagttgaaat ctggaactgc ctctgttgtg tgcctgctga    420
ataacttcta tcccagagag gccaaagtac agtggaaggt ggataacgcc ctccaatcgg    480
gtaactccca ggagagtgtc acagagcagg acagcaagga cagcacctac agcctcagca    540
gcaccctgac gctgagcaaa gcagactacg agaaacacaa agtctacgcc tgcgaagtca    600
cccatcaggg cctgagctcg cccgtcacaa agagcttcaa caggggagag tgt           653
```

<210> SEQ ID NO 21
<211> LENGTH: 1344
<212> TYPE: DNA
<213> ORGANISM: Artificial Sequence
<220> FEATURE:
<223> OTHER INFORMATION: Synthetic construct

<400> SEQUENCE: 21

```
gaggttcagc tggtggagtc tggcggtggc ctggtgcagc cagggggctc actccgtttg     60
tcctgtgcag cttctggctt caacctctct tcttcttcta tccactgggt gcgtcaggcc    120
ccgggtaagg gcctggaatg ggttgcatat atttatcctt attatagcta tactattat     180 gccgatagcg tcaagggccg tttcactata agcgcagaca catccaaaaa cacagcctac    240
ctacaaatga acagcttaag agctgaggac actgccgtct attattgtgc tcgcttcggt    300
tctgttgctg gttttgacta ctggggtcaa ggaaccctgg tcaccgtctc ctcggctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc    600
```

```
tgcaacgtga atcacaagcc cagcaacacc aaggtggaca agaaagttga gcccaaatct    660
tgtgacaaaa ctcacacatg cccaccgtgc ccagcacctg aactcctggg gggaccgtca    720
gtcttcctct ccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga ggagatgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 22
<211> LENGTH: 461
<212> TYPE: PRT
<213> ORGANISM: Artificial Sequence
<220> FEATURE:
<223> OTHER INFORMATION: Synthetic construct

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser His Ala Gly His
                85                  90                  95

Leu Phe Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Gly Ser Asp Ile Lys
    210                 215                 220
```

```
Leu Gln Gln Ser Gly Ala Glu Leu Ala Arg Pro Gly Ala Ser Val Lys
225                 230                 235                 240

Met Ser Cys Lys Thr Ser Gly Tyr Thr Phe Thr Arg Tyr Thr Met His
            245                 250                 255

Trp Val Lys Gln Arg Pro Gly Gln Gly Leu Glu Trp Ile Gly Tyr Ile
        260                 265                 270

Asn Pro Ser Arg Gly Tyr Thr Asn Tyr Asn Gln Lys Phe Lys Asp Lys
    275                 280                 285

Ala Thr Leu Thr Thr Asp Lys Ser Ser Thr Ala Tyr Met Gln Leu
290                 295                 300

Ser Ser Leu Thr Ser Glu Asp Ser Ala Val Tyr Tyr Cys Ala Arg Tyr
305                 310                 315                 320

Tyr Asp Asp His Tyr Cys Leu Asp Tyr Trp Gly Gln Gly Thr Thr Leu
            325                 330                 335

Thr Val Ser Ser Gly Gly Gly Gly Ser Gly Gly Gly Ser Gly Gly
        340                 345                 350

Gly Gly Ser Asp Ile Gln Leu Thr Gln Ser Pro Ala Ile Met Ser Ala
    355                 360                 365

Ser Pro Gly Glu Lys Val Thr Met Thr Cys Arg Ala Ser Ser Ser Val
370                 375                 380

Ser Tyr Met Asn Trp Tyr Gln Gln Lys Ser Gly Thr Ser Pro Lys Arg
385                 390                 395                 400

Trp Ile Tyr Asp Thr Ser Lys Val Ala Ser Gly Val Pro Tyr Arg Phe
            405                 410                 415

Ser Gly Ser Gly Ser Gly Thr Ser Tyr Ser Leu Thr Ile Ser Ser Met
        420                 425                 430

Glu Ala Glu Asp Ala Ala Thr Tyr Tyr Cys Gln Gln Trp Ser Ser Asn
    435                 440                 445

Pro Leu Thr Phe Gly Ala Gly Thr Lys Leu Glu Leu Lys
450                 455                 460

<210> SEQ ID NO 23
<211> LENGTH: 226
<212> TYPE: PRT
<213> ORGANISM: Artificial Sequence
<220> FEATURE:
<223> OTHER INFORMATION: Synthetic construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Tyr Ser Tyr Thr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Phe Gly Ser Val Ala Gly Phe Asp Tyr Trp Gly Gln Gly Thr
        100                 105                 110

Leu Val Thr Val Ser Ser Ala Ser Thr Lys Gly Pro Ser Val Phe Pro
    115                 120                 125
```

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr
225

<210> SEQ ID NO 24
<211> LENGTH: 471
<212> TYPE: PRT
<213> ORGANISM: Artificial Sequence
<220> FEATURE:
<223> OTHER INFORMATION: Synthetic construct

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Tyr Ser Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Ser Val Ala Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Gly Gly Gly Gly Ser Asp Ile Lys Leu Gln Gln Ser Gly Ala
225                 230                 235                 240

Glu Leu Ala Arg Pro Gly Ala Ser Val Lys Met Ser Cys Lys Thr Ser
                245                 250                 255

```
Gly Tyr Thr Phe Thr Arg Tyr Thr Met His Trp Val Lys Gln Arg Pro
                260                 265                 270

Gly Gln Gly Leu Glu Trp Ile Gly Tyr Ile Asn Pro Ser Arg Gly Tyr
            275                 280                 285

Thr Asn Tyr Asn Gln Lys Phe Lys Asp Lys Ala Thr Leu Thr Thr Asp
290                 295                 300

Lys Ser Ser Ser Thr Ala Tyr Met Gln Leu Ser Ser Leu Thr Ser Glu
305                 310                 315                 320

Asp Ser Ala Val Tyr Tyr Cys Ala Arg Tyr Tyr Asp Asp His Tyr Cys
                325                 330                 335

Leu Asp Tyr Trp Gly Gln Gly Thr Thr Leu Thr Val Ser Ser Gly Gly
            340                 345                 350

Gly Gly Ser Gly Gly Gly Gly Ser Gly Gly Gly Gly Ser Asp Ile Gln
            355                 360                 365

Leu Thr Gln Ser Pro Ala Ile Met Ser Ala Ser Pro Gly Glu Lys Val
370                 375                 380

Thr Met Thr Cys Arg Ala Ser Ser Ser Val Ser Tyr Met Asn Trp Tyr
385                 390                 395                 400

Gln Gln Lys Ser Gly Thr Ser Pro Lys Arg Trp Ile Tyr Asp Thr Ser
                405                 410                 415

Lys Val Ala Ser Gly Val Pro Tyr Arg Phe Ser Gly Ser Gly Ser Gly
            420                 425                 430

Thr Ser Tyr Ser Leu Thr Ile Ser Ser Met Glu Ala Glu Asp Ala Ala
            435                 440                 445

Thr Tyr Tyr Cys Gln Gln Trp Ser Ser Asn Pro Leu Thr Phe Gly Ala
450                 455                 460

Gly Thr Lys Leu Glu Leu Lys
465                 470

<210> SEQ ID NO 25
<211> LENGTH: 216
<212> TYPE: PRT
<213> ORGANISM: Artificial Sequence
<220> FEATURE:
<223> OTHER INFORMATION: Synthetic construct

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser His Ala Gly His
                85                  90                  95

Leu Phe Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140
```

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 26
<211> LENGTH: 724
<212> TYPE: PRT
<213> ORGANISM: Artificial Sequence
<220> FEATURE:
<223> OTHER INFORMATION: Synthetic construct

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser His Ala Gly His
                85                  90                  95

Leu Phe Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Ser Ser Gly Ser Gly Ser
    210                 215                 220

Gly Ser Thr Gly Thr Ser Ser Gly Thr Gly Ser Ala Gly Thr
225                 230                 235                 240

Thr Gly Thr Ser Ala Ser Thr Ser Gly Ser Gly Ser Gly Glu Val Gln
                245                 250                 255

Leu Val Glu Ser Gly Gly Gly Leu Val Gln Pro Gly Gly Ser Leu Arg
            260                 265                 270

Leu Ser Cys Ala Ala Ser Gly Phe Asn Leu Ser Ser Ser Ile His
        275                 280                 285

Trp Val Arg Gln Ala Pro Gly Lys Gly Leu Glu Trp Val Ala Tyr Ile
290                 295                 300

Tyr Pro Tyr Tyr Ser Tyr Thr Tyr Tyr Ala Asp Ser Val Lys Gly Arg
305                 310                 315                 320

Phe Thr Ile Ser Ala Asp Thr Ser Lys Asn Thr Ala Tyr Leu Gln Met
            325                 330                 335

Asn Ser Leu Arg Ala Glu Asp Thr Ala Val Tyr Tyr Cys Ala Arg Phe
                340                 345                 350

Gly Ser Val Ala Gly Phe Asp Tyr Trp Gly Gln Gly Thr Leu Val Thr
            355                 360                 365

Val Ser Ser Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
    435                 440                 445

Thr Gln Thr Tyr Ile Cys Asn Val Asn His Lys Pro Ser Asn Thr Lys
    450                 455                 460

Val Asp Lys Lys Val Glu Pro Lys Ser Cys Asp Lys Thr His Thr Gly
465                 470                 475                 480

Gly Gly Gly Ser Asp Ile Lys Leu Gln Gln Ser Gly Ala Glu Leu Ala
            485                 490                 495

Arg Pro Gly Ala Ser Val Lys Met Ser Cys Lys Thr Ser Gly Tyr Thr
            500                 505                 510

Phe Thr Arg Tyr Thr Met His Trp Val Lys Gln Arg Pro Gly Gln Gly
    515                 520                 525

Leu Glu Trp Ile Gly Tyr Ile Asn Pro Ser Arg Gly Tyr Thr Asn Tyr
530                 535                 540

Asn Gln Lys Phe Lys Asp Lys Ala Thr Leu Thr Thr Asp Lys Ser Ser
545                 550                 555                 560

Ser Thr Ala Tyr Met Gln Leu Ser Ser Leu Thr Ser Glu Asp Ser Ala
                565                 570                 575

Val Tyr Tyr Cys Ala Arg Tyr Tyr Asp Asp His Tyr Cys Leu Asp Tyr
            580                 585                 590

Trp Gly Gln Gly Thr Thr Leu Thr Val Ser Ser Gly Gly Gly Gly Ser
    595                 600                 605

Gly Gly Gly Gly Ser Gly Gly Gly Gly Ser Asp Ile Gln Leu Thr Gln
610                 615                 620

Ser Pro Ala Ile Met Ser Ala Ser Pro Gly Glu Lys Val Thr Met Thr
625                 630                 635                 640

Cys Arg Ala Ser Ser Ser Val Ser Tyr Met Asn Trp Tyr Gln Gln Lys
                645                 650                 655

Ser Gly Thr Ser Pro Lys Arg Trp Ile Tyr Asp Thr Ser Lys Val Ala
            660                 665                 670

Ser Gly Val Pro Tyr Arg Phe Ser Gly Ser Gly Ser Gly Thr Ser Tyr
            675                 680                 685

Ser Leu Thr Ile Ser Ser Met Glu Ala Glu Asp Ala Ala Thr Tyr Tyr
    690                 695                 700

Cys Gln Gln Trp Ser Ser Asn Pro Leu Thr Phe Gly Ala Gly Thr Lys

```
                705                 710                 715                 720
Leu Glu Leu Lys

<210> SEQ ID NO 27
<211> LENGTH: 724
<212> TYPE: PRT
<213> ORGANISM: Artificial Sequence
<220> FEATURE:
<223> OTHER INFORMATION: Synthetic construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Tyr Ser Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Ser Val Ala Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Gly Gly Ser Gly Ser Gly Ser Gly Ser Thr Gly Thr Ser
225                 230                 235                 240

Ser Ser Gly Thr Gly Thr Ser Ala Gly Thr Thr Gly Thr Ser Ala Ser
                245                 250                 255

Thr Ser Gly Ser Gly Ser Gly Asp Ile Gln Met Thr Gln Ser Pro Ser
            260                 265                 270

Ser Leu Ser Ala Ser Val Gly Asp Arg Val Thr Ile Thr Cys Arg Ala
        275                 280                 285

Ser Gln Ser Val Ser Ser Ala Val Ala Trp Tyr Gln Gln Lys Pro Gly
    290                 295                 300

Lys Ala Pro Lys Leu Leu Ile Tyr Ser Ala Ser Ser Leu Tyr Ser Gly
305                 310                 315                 320

Val Pro Ser Arg Phe Ser Gly Ser Arg Ser Gly Thr Asp Phe Thr Leu
                325                 330                 335

Thr Ile Ser Ser Leu Gln Pro Glu Asp Phe Ala Thr Tyr Tyr Cys Gln
            340                 345                 350
```

-continued

Gln Tyr Ser His Ala Gly His Leu Phe Thr Phe Gly Gln Gly Thr Lys
            355                 360                 365

Val Glu Ile Lys Arg Thr Val Ala Ala Pro Ser Val Phe Ile Phe Pro
370                 375                 380

Pro Ser Asp Glu Gln Leu Lys Ser Gly Thr Ala Ser Val Val Cys Leu
385                 390                 395                 400

Leu Asn Asn Phe Tyr Pro Arg Glu Ala Lys Val Gln Trp Lys Val Asp
                405                 410                 415

Asn Ala Leu Gln Ser Gly Asn Ser Gln Glu Ser Val Thr Glu Gln Asp
            420                 425                 430

Ser Lys Asp Ser Thr Tyr Ser Leu Ser Ser Thr Leu Thr Leu Ser Lys
        435                 440                 445

Ala Asp Tyr Glu Lys His Lys Val Tyr Ala Cys Glu Val Thr His Gln
450                 455                 460

Gly Leu Ser Ser Pro Val Thr Lys Ser Phe Asn Arg Gly Glu Cys Gly
465                 470                 475                 480

Gly Gly Gly Ser Asp Ile Lys Leu Gln Gln Ser Gly Ala Glu Leu Ala
                485                 490                 495

Arg Pro Gly Ala Ser Val Lys Met Ser Cys Lys Thr Ser Gly Tyr Thr
            500                 505                 510

Phe Thr Arg Tyr Thr Met His Trp Val Lys Gln Arg Pro Gly Gln Gly
        515                 520                 525

Leu Glu Trp Ile Gly Tyr Ile Asn Pro Ser Arg Gly Tyr Thr Asn Tyr
    530                 535                 540

Asn Gln Lys Phe Lys Asp Lys Ala Thr Leu Thr Thr Asp Lys Ser Ser
545                 550                 555                 560

Ser Thr Ala Tyr Met Gln Leu Ser Ser Leu Thr Ser Glu Asp Ser Ala
                565                 570                 575

Val Tyr Tyr Cys Ala Arg Tyr Tyr Asp Asp His Tyr Cys Leu Asp Tyr
            580                 585                 590

Trp Gly Gln Gly Thr Thr Leu Thr Val Ser Ser Gly Gly Gly Gly Ser
        595                 600                 605

Gly Gly Gly Gly Ser Gly Gly Gly Gly Ser Asp Ile Gln Leu Thr Gln
    610                 615                 620

Ser Pro Ala Ile Met Ser Ala Ser Pro Gly Glu Lys Val Thr Met Thr
625                 630                 635                 640

Cys Arg Ala Ser Ser Ser Val Ser Tyr Met Asn Trp Tyr Gln Gln Lys
                645                 650                 655

Ser Gly Thr Ser Pro Lys Arg Trp Ile Tyr Asp Thr Ser Lys Val Ala
            660                 665                 670

Ser Gly Val Pro Tyr Arg Phe Ser Gly Ser Gly Ser Gly Thr Ser Tyr
        675                 680                 685

Ser Leu Thr Ile Ser Ser Met Glu Ala Glu Asp Ala Ala Thr Tyr Tyr
    690                 695                 700

Cys Gln Gln Trp Ser Ser Asn Pro Leu Thr Phe Gly Ala Gly Thr Lys
705                 710                 715                 720

Leu Glu Leu Lys

<210> SEQ ID NO 28
<211> LENGTH: 106
<212> TYPE: PRT
<213> ORGANISM: Artificial Sequence
<220> FEATURE:
<223> OTHER INFORMATION: Synthetic construct

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ser Ser Tyr Val
            20                  25                  30

Ala Trp Tyr Gln Gln Lys Pro Gly Lys Ala Pro Lys Leu Leu Ile Tyr
        35                  40                  45

Ser Ala Ser Tyr Leu Tyr Ser Gly Val Pro Ser Arg Phe Ser Gly Ser
    50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Gly Val Trp Ser Leu Ile Thr
                85                  90                  95

Phe Gly Gln Gly Thr Lys Val Glu Ile Lys
            100                 105

<210> SEQ ID NO 29
<211> LENGTH: 126
<212> TYPE: PRT
<213> ORGANISM: Artificial Sequence
<220> FEATURE:
<223> OTHER INFORMATION: Synthetic construct

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Tyr
            20                  25                  30

Gly Ser Met His Trp Val Arg Gln Ala Pro Gly Lys Gly Leu Glu Trp
        35                  40                  45

Val Ala Ser Ile Ser Pro Tyr Tyr Gly Ser Thr Tyr Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg His Ala Ser Ser Gly Tyr Gly His Tyr Ala Val Tyr Gly
            100                 105                 110

Ile Asp Tyr Trp Gly Gln Gly Thr Leu Val Thr Val Ser Ser
        115                 120                 125

<210> SEQ ID NO 30
<211> LENGTH: 109
<212> TYPE: PRT
<213> ORGANISM: Artificial Sequence
<220> FEATURE:
<223> OTHER INFORMATION: Synthetic contruct

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser His Ala Gly His
                85                  90                  95

Leu Phe Thr Phe Gly Gln Gly Thr Lys Val Glu Ile Lys
            100                 105

<210> SEQ ID NO 31
<211> LENGTH: 118
<212> TYPE: PRT
<213> ORGANISM: Artificial Sequence
<220> FEATURE:
<223> OTHER INFORMATION: Synthetic construct

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
            20                  25                  30

Ser Ile His Trp Val Arg Gln Ala Pro Gly Lys Gly Leu Glu Trp Val
        35                  40                  45

Ala Tyr Ile Tyr Pro Tyr Tyr Ser Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Ser Val Ala Gly Phe Asp Tyr Trp Gly Gln Gly Thr
            100                 105                 110

Leu Val Thr Val Ser Ser
        115

<210> SEQ ID NO 32
<211> LENGTH: 9
<212> TYPE: PRT
<213> ORGANISM: Artificial Sequence
<220> FEATURE:
<223> OTHER INFORMATION: Synthetic construct

<400> SEQUENCE: 32

Gly Ser Met Ile Tyr Tyr Tyr Gly Ser
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic construct

<400> SEQUENCE: 33

Ser Ile Ser Pro Tyr Tyr Gly Ser Thr Tyr
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic construct

<400> SEQUENCE: 34

```
Gly Phe Asn Leu Ser Ser Ser Ser Ile
1               5
```

<210> SEQ ID NO 35
<211> LENGTH: 10
<212> TYPE: PRT
<213> ORGANISM: Artificial Sequence
<220> FEATURE:
<223> OTHER INFORMATION: Synthetic construct

<400> SEQUENCE: 35

```
Tyr Ile Tyr Pro Tyr Tyr Ser Tyr Thr Tyr
1               5                   10
```

<210> SEQ ID NO 36
<211> LENGTH: 15
<212> TYPE: DNA
<213> ORGANISM: Artificial Sequence
<220> FEATURE:
<223> OTHER INFORMATION: Synthetic construct

<400> SEQUENCE: 36
cagggttctt cttac                                                    15

<210> SEQ ID NO 37
<211> LENGTH: 9
<212> TYPE: DNA
<213> ORGANISM: Artificial Sequence
<220> FEATURE:
<223> OTHER INFORMATION: Synthetic construct

<400> SEQUENCE: 37 tctgcatcc                                                            9

<210> SEQ ID NO 38
<211> LENGTH: 27
<212> TYPE: DNA
<213> ORGANISM: Artificial Sequence
<220> FEATURE:
<223> OTHER INFORMATION: Synthetic construct

<400> SEQUENCE: 38
cagcaaggtg tttggtctct gatcacg                                       27

<210> SEQ ID NO 39
<211> LENGTH: 27
<212> TYPE: DNA
<213> ORGANISM: Artificial Sequence
<220> FEATURE:
<223> OTHER INFORMATION: Synthetic construct

<400> SEQUENCE: 39
ggcttcaaca tctactacta cggttct                                       27

<210> SEQ ID NO 40
<211> LENGTH: 24
<212> TYPE: DNA
<213> ORGANISM: Artificial Sequence
<220> FEATURE:
<223> OTHER INFORMATION: Synthetic construct

<400> SEQUENCE: 40
atttctcctt actacggctc tact                                          24

<210> SEQ ID NO 41

```
<211> LENGTH: 54
<212> TYPE: DNA
<213> ORGANISM: Artificial Sequence
<220> FEATURE:
<223> OTHER INFORMATION: Synthetic construct

<400> SEQUENCE: 41
gctcgccatg cttcttctgg ttacggtcat tacgctgttt acggtattga ctac         54

<210> SEQ ID NO 42
<211> LENGTH: 30
<212> TYPE: DNA
<213> ORGANISM: Artificial Sequence
<220> FEATURE:
<223> OTHER INFORMATION: Synthetic construct

<400> SEQUENCE: 42
ggcttcaaca tctactacta cggttctatg                                    30

<210> SEQ ID NO 43
<211> LENGTH: 30
<212> TYPE: DNA
<213> ORGANISM: Artificial Sequence
<220> FEATURE:
<223> OTHER INFORMATION: Synthetic construct

<400> SEQUENCE: 43
tctatttctc cttactacgg ctctacttac                                    30

<210> SEQ ID NO 44
<211> LENGTH: 18
<212> TYPE: DNA
<213> ORGANISM: Artificial Sequence
<220> FEATURE:
<223> OTHER INFORMATION: Synthetic construct

<400> SEQUENCE: 44
cagtccgtgt ccagcgct                                                 18

<210> SEQ ID NO 45
<211> LENGTH: 9
<212> TYPE: DNA
<213> ORGANISM: Artificial Sequence
<220> FEATURE:
<223> OTHER INFORMATION: Synthetic construct

<400> SEQUENCE: 45 tcggcatcc                                                            9

<210> SEQ ID NO 46
<211> LENGTH: 33
<212> TYPE: DNA
<213> ORGANISM: Artificial Sequence
<220> FEATURE:
<223> OTHER INFORMATION: Synthetic construct

<400> SEQUENCE: 46
cagcaatact ctcatgctgg tcatctgttc acg                                33

<210> SEQ ID NO 47
<211> LENGTH: 24
<212> TYPE: DNA
<213> ORGANISM: Artificial Sequence
<220> FEATURE:
<223> OTHER INFORMATION: Synthetic construct

<400> SEQUENCE: 47
```

```
ggcttcaacc tctcttcttc ttct                                          24

<210> SEQ ID NO 48
<211> LENGTH: 24
<212> TYPE: DNA
<213> ORGANISM: Artificial Sequence
<220> FEATURE:
<223> OTHER INFORMATION: Synthetic construct

<400> SEQUENCE: 48
atttatcctt attatagcta tact                                          24

<210> SEQ ID NO 49
<211> LENGTH: 33
<212> TYPE: DNA
<213> ORGANISM: Artificial Sequence
<220> FEATURE:
<223> OTHER INFORMATION: Synthetic construct

<400> SEQUENCE: 49
gctcgcttcg gttctgttgc tggttttgac tac                                33

<210> SEQ ID NO 50
<211> LENGTH: 27
<212> TYPE: DNA
<213> ORGANISM: Artificial Sequence
<220> FEATURE:
<223> OTHER INFORMATION: Synthetic construct

<400> SEQUENCE: 50
ggcttcaacc tctcttcttc ttctatc                                       27

<210> SEQ ID NO 51
<211> LENGTH: 30
<212> TYPE: DNA
<213> ORGANISM: Artificial Sequence
<220> FEATURE:
<223> OTHER INFORMATION: Synthetic construct

<400> SEQUENCE: 51
tatatttatc cttattatag ctatacttat                                    30

<210> SEQ ID NO 52
<211> LENGTH: 323
<212> TYPE: DNA
<213> ORGANISM: Artificial Sequence
<220> FEATURE:
<223> OTHER INFORMATION: Synthetic construct

<400> SEQUENCE: 52
gatatccaga tgacccagtc cccgagctcc ctgtccgcct ctgtgggcga tagggtcacc    60
atcacctgcc gtgccagtca gggttcttct tacgtagcct ggtatcaaca gaaaccagga   120
aaagctccga agcttctgat ttactctgca tcctacctct actctactct ggagtccctt   180
ctcgcttctc tggtagccgt tccgggacgg atttcactct gaccatcagc agtctgcagc   240
cggaagactt cgcaacttat tactgtcagc aaggtgtttg gtctctgatc acgttcggac   300
agggtaccaa ggtggagatc aaa                                          323

<210> SEQ ID NO 53
<211> LENGTH: 354
<212> TYPE: DNA
<213> ORGANISM: Artificial Sequence
<220> FEATURE:
```

```
<223> OTHER INFORMATION: Synthetic construct

<400> SEQUENCE: 53
gaggttcagc tggtggagtc tggcggtggc ctggtgcagc caggggctc actccgtttg      60 tcctgtgcag cttctggctt caacctctct tcttcttcta tccactgggt gcgtcaggcc    120
ccgggtaagg gcctggaatg ggttgcatat atttatcctt attatagcta tacttattat    180
gccgatagcg tcaagggccg tttcactata agcgcagaca catccaaaaa cacagcctac    240
ctacaaatga acagcttaag agctgaggac actgccgtct attattgtgc tcgcttcggt    300
tctgttgctg gttttgacta ctggggtcaa ggaaccctgg tcaccgtctc ctcg          354

<210> SEQ ID NO 54
<211> LENGTH: 332
<212> TYPE: DNA
<213> ORGANISM: Artificial Sequence
<220> FEATURE:
<223> OTHER INFORMATION: Synthetic construct

<400> SEQUENCE: 54
gatatccaga tgacccagtc cccgagctcc ctgtccgcct ctgtgggcga tagggtcacc     60
atcacctgcc gtgccagtca gtccgtgtcc agcgctgtag cctggtatca acagaaacca   120
ggaaaagctc cgaagcttct gatttactcg gcatccagcc tctactctac tctggagtcc   180
cttctcgctt ctctggtagc cgttccggga cggatttcac tctgaccatc agcagtctgc   240
agccggaaga cttcgcaact tattactgtc agcaatactc tcatgctggt catctgttca   300
cgttcggaca gggtaccaag gtggagatca aa                                  332

<210> SEQ ID NO 55
<211> LENGTH: 354
<212> TYPE: DNA
<213> ORGANISM: Artificial Sequence
<220> FEATURE:
<223> OTHER INFORMATION: Synthetic construct

<400> SEQUENCE: 55
gaggttcagc tggtggagtc tggcggtggc ctggtgcagc caggggctc actccgtttg      60 tcctgtgcag cttctggctt caacctctct tcttcttcta tccactgggt gcgtcaggcc    120
ccgggtaagg gcctggaatg ggttgcatat atttatcctt attatagcta tacttattat    180
gccgatagcg tcaagggccg tttcactata agcgcagaca catccaaaaa cacagcctac    240
ctacaaatga acagcttaag agctgaggac actgccgtct attattgtgc tcgcttcggt    300
tctgttgctg gttttgacta ctggggtcaa ggaaccctgg tcaccgtctc ctcg          354
```

CD133-BINDING AGENTS AND USES THEREOF

CROSS-REFERENCE TO RELATED APPLICATIONS

This application is a national phase entry of PCT/CA2017/051245 filed Oct. 19, 2017 (which designates the U.S.), which claims the benefit of priority to U.S. Provisional Application No. 62/410,162 filed Oct. 19, 2016, and U.S. Provisional Application No. 62/472,209 filed Mar. 16, 2017, the contents of both of which are incorporated herein by reference in their entirety.

Incorporation of Sequence Listing

A computer readable form of the Sequence Listing "25301-P51681US02_SequenceListing.txt" (65,536 bytes), submitted via EFS-WEB and created on Apr. 17, 2019, is herein incorporated by reference.

FIELD

This disclosure relates generally to CD133-binding agents, and to methods and uses of these binding agents.

BACKGROUND

CD133 has been identified as a marker in melanoma, brain tumors and various carcinomas, including breast, colon, gastric, prostate, liver, pancreatic, lung cancer and head and neck squamous cell carcinoma (Boman et al., 2008; Ferrandina et al., 2009). CD133 expression is often associated with poor survival, drug resistance and metastasis. A correlation between CD133 overexpression, histopathological factors and poor patient outcome has been reported in hepatocellular carcinoma (Zhong et al., 2015). CD133 is a membrane-bound pentaspan glycoprotein, the exact physiologic role of which remains unclear. It is thought to be involved in primitive cell differentiation and epidermal-mesenchymal interaction (Bauer et al., 2008; Ulasov et al., 2011; Evangelista et al., 2006), and to be associated with the WNT signaling pathway and associated cell proliferation (Rappa et al., 2008; Mak et al., 2012a; Takenobu et al., 2011). Downregulation of CD133 in a metastatic melanoma cell line has been shown to result in reduced metastatic capacity of xenografts (Rappa et al., 2008).

Glioblastoma (GBM) is a uniformly fatal primary brain tumor, characterized by a diverse cellular phenotype and genetic heterogeneity. Despite the use of aggressive cellular multi-modal treatment including surgical resection, radiotherapy and chemotherapy, the outcome of patients with GBM has failed to improve significantly. Numerous studies have implicated CD133+ brain tumor initiating cells (BTICs) as drivers of chemo- and radio-resistance in GBM. It has also recently been demonstrated that a CD133-driven gene signature is predictive of poor overall survival (Venugopal et al, 2015) and targeting CD133+ treatment refractory cells may be an effective strategy to block GBM recurrence. Medulloblastoma cells that are CD133+ have also been associated with increased multipotency and enriched brain cancer stem cell activity (Singh et al, 2004).

Anti-CD133 antibody-based drugs have been proposed for treatment of cancer (reviewed in Schmohl and Vallera, 2016). Significant but temporary regression of recurrent glioblastoma after anti-IL13alpha chimeric antigen receptor T-cell therapy has been reported in a human patient (Brown et al., 2016). A need remains for novel agents that bind CD133 with high affinity and specificity.

SUMMARY

The present inventors have described novel antibody variable regions RW01 and RW03 capable of specifically binding both cell surface-expressed as well as denatured human CD133, and demonstrated specific CD133-binding by binding agents (e.g. antibodies, Fabs, scFvs, Fab-based bispecific antibodies/bispecific T cell engagers (BiTEs) and/or scFab-based bispecific antibodies/BiTEs) comprising these CD133-binding variable regions. It was shown that antibodies with the presently disclosed variable regions specifically bind cell surface-expressed/native human CD133 with a dissociation constant ($K_D$) in the subnanomolar/nanomolar range. It was shown that such CD133-binding antibodies can be used to specifically detect CD133 expressed on the surface of cells, such as cancer cells (e.g. pancreatic cancer cells, colorectal cancer cells); specifically bind and detect denatured CD133, e.g. in cell lysates; specifically bind, detect and subcellularly localize cellular CD133 via immunofluorescence analysis; and significantly reduce levels of CD133 protein in CD133-positive (CD133+) cancer cells. It was further shown that Fab comprising antibody variable region RW01 and Fab comprising antibody variable region RW03 do not compete with IgG RW03 and IgG RW01, respectively, for binding to CD133.

The present inventors have also shown that CD133 specific CAR-T cells specifically induce CD133-positive glioblastoma (GBM) cell death and induce GBM tumor regression in vivo. The inventors have also shown that CD133-specific BiTEs recruit T cells to CD133+ human GBM cells and cause cell death. In addition, tumors formed in mouse brain intracranially treated with CD133-specific BiTEs were less aggressive and invasive.

Accordingly, the present disclosure provides a CD133-binding agent which specifically binds cell surface-expressed/native CD133 and which specifically binds denatured CD133.

In one embodiment, the CD133-binding agent specifically binds a CD133 epitope bound by an antibody comprising: (a) a light chain having the amino acid sequence of SEQ ID NO: 2, and a heavy chain having the amino acid sequence of SEQ ID NO: 3; and/or (b) a light chain having the amino acid sequence of SEQ ID NO: 4 and a heavy chain having the amino acid sequence of SEQ ID NO: 5.

In another embodiment, the CD133-binding agent specifically binds a CD133 epitope of cell surface-expressed CD133 which is bound by an antibody comprising a light chain having the amino acid sequence of SEQ ID NO: 2 and a heavy chain having the amino acid sequence of SEQ ID NO: 3, and/or which is bound by an antibody comprising a light chain having the amino acid sequence of SEQ ID NO: 4 and a heavy chain having the amino acid sequence of SEQ ID NO: 5.

In a further embodiment, the CD133-binding agent specifically binds a CD133 epitope of denatured CD133 which is bound by an antibody comprising a light chain having the amino acid sequence of SEQ ID NO: 2 and a heavy chain having the amino acid sequence of SEQ ID NO: 3, and/or which is bound by an antibody comprising a light chain having the amino acid sequence of SEQ ID NO: 4 and a heavy chain having the amino acid sequence of SEQ ID NO: 5.

In one embodiment, the CD133-binding agent comprises an antibody light chain variable domain and an antibody heavy chain variable domain which form an antigen binding site that specifically binds human CD133.

In another embodiment, the antibody light chain variable domain comprises a light chain complementarity-determining region (CDR)1 comprising the amino acid sequence of SEQ ID NO: 6, a light chain CDR2 comprising the amino acid sequence of SEQ ID NO: 7, and a light chain CDR3 comprising the amino acid sequence of SEQ ID NO: 8; and the antibody heavy chain variable domain comprises a heavy chain CDR1 comprising the amino acid sequence of SEQ ID NO: 9, a heavy chain CDR2 comprising the amino acid sequence of SEQ ID NO: 10, and a heavy chain CDR3 comprising the amino acid sequence of SEQ ID NO: 11, wherein the light chain variable domain and the heavy chain variable domain form the antigen binding site that binds human CD133. Optionally, the heavy chain variable domain further comprises a Met residue at position 39, a Ser residue at position 55 and a Tyr residue at position 66.

In a further embodiment, the antibody light chain variable domain comprises a light chain complementarity-determining region (CDR)1 consisting of the amino acid sequence of SEQ ID NO: 6, a light chain CDR2 consisting of the amino acid sequence of SEQ ID NO: 7, and a light chain CDR3 consisting of the amino acid sequence of SEQ ID NO: 8; and the antibody heavy chain variable domain comprises a heavy chain CDR1 consisting of the amino acid sequence of SEQ ID NO: 9, a heavy chain CDR2 consisting of the amino acid sequence of SEQ ID NO: 10, and a heavy chain CDR3 consisting of the amino acid sequence of SEQ ID NO: 11, wherein the light chain variable domain and the heavy chain variable domain form the antigen binding site that binds human CD133. Optionally, the heavy chain variable domain further comprises a Met residue at position 39, a Ser residue at position 55 and a Tyr residue at position 66.

In another embodiment, the antibody light chain comprises the amino acid sequence of SEQ ID NO: 2 or an amino acid sequence having at least 70% sequence identity to the framework regions of SEQ ID NO: 2.

In another embodiment, the antibody light chain consists of the amino acid sequence of SEQ ID NO: 2.

In another embodiment, the heavy chain comprises the amino acid sequence of SEQ ID NO: 3 or an amino acid sequence having at least 70% sequence identity to the framework regions of SEQ ID NO: 3.

In another embodiment, the antibody heavy chain consists of the amino acid sequence of SEQ ID NO: 3.

In another embodiment, the light chain comprises (i) the amino acid sequence of SEQ ID NO: 2 or an amino acid sequence having at least 70% sequence identity to the framework regions of SEQ ID NO: 2, and (ii) the heavy chain comprises the amino acid sequence of SEQ ID NO: 3 or an amino acid sequence having at least 70% sequence identity to the framework regions of SEQ ID NO: 3.

In another embodiment, the light chain consists of the amino acid sequence of SEQ ID NO: 2, and the heavy chain consists of the amino acid sequence of SEQ ID NO: 3.

In another embodiment, the antibody light chain variable domain comprises a light chain complementarity-determining region (CDR)1 comprising the amino acid sequence of SEQ ID NO: 12, a light chain CDR2 comprising the amino acid sequence of SEQ ID NO: 13, and a light chain CDR3 comprising the amino acid sequence of SEQ ID NO: 14; and the antibody heavy chain variable domain comprises a heavy chain CDR1 comprising the amino acid sequence of SEQ ID NO: 15, a heavy chain CDR2 comprising the amino acid sequence of SEQ ID NO: 16, and a heavy chain CDR3 comprising the amino acid sequence of SEQ ID NO: 17, wherein the light chain variable domain and the heavy chain variable domain form the antigen binding site that binds human CD133. Optionally, the heavy chain variable domain further comprises a Ile residue at position 39, a Tyr residue at position 55 and a Tyr residue at position 66.

In one embodiment, the antibody light chain variable domain comprises a light chain complementarity-determining region (CDR)1 consisting of the amino acid sequence of SEQ ID NO: 12, a light chain CDR2 consisting of the amino acid sequence of SEQ ID NO: 13, and a light chain CDR3 consisting of the amino acid sequence of SEQ ID NO: 14; and the antibody heavy chain variable domain comprises a heavy chain CDR1 consisting of the amino acid sequence of SEQ ID NO: 15, a heavy chain CDR2 consisting of the amino acid sequence of SEQ ID NO: 16, and a heavy chain CDR3 consisting of the amino acid sequence of SEQ ID NO: 17, wherein the light chain variable domain and the heavy chain variable domain form the antigen binding site that binds human CD133. Optionally, the heavy chain variable domain further comprises a Ile residue at position 39, a Tyr residue at position 55 and a Tyr residue at position 66.

In another embodiment, the antibody light chain comprises the amino acid sequence of SEQ ID NO: 4 or an amino acid sequence having at least 70% sequence identity to the framework regions of SEQ ID NO: 4.

In another embodiment, the antibody light chain consists of the amino acid sequence of SEQ ID NO: 4.

In another embodiment, the antibody heavy chain comprises the amino acid sequence of SEQ ID NO: 5 or an amino acid sequence having at least 70% sequence identity to the framework regions of SEQ ID NO: 5.

In another embodiment, the antibody heavy chain consists of the amino acid sequence of SEQ ID NO: 5.

In another embodiment, the light chain comprises the amino acid sequence of SEQ ID NO: 4 or an amino acid sequence having at least 70% sequence identity to the framework regions of SEQ ID NO: 4, and the heavy chain comprises the amino acid sequence of SEQ ID NO: 5 or an amino acid sequence having at least 70% sequence identity to the framework regions of SEQ ID NO: 5.

In another embodiment, the light chain consists of the amino acid sequence of SEQ ID NO: 4, and the heavy chain consists of the amino acid sequence of SEQ ID NO: 5.

In another embodiment, the CD133-binding agent is selected from the group consisting of an antibody, an antibody fragment, a single-chain Fv (scFv), a bispecific antibody, a phage-Fab wherein the Fab binds CD133 and a phage-scFv wherein the scFv binds CD133.

In another embodiment, the CD133-binding agent comprises an antibody that binds human CD133.

In another embodiment, the CD133-binding agent comprises an antibody fragment that binds human CD133.

In another embodiment, the CD133-binding agent comprises a single-chain Fv (scFv) that binds human CD133.

In another embodiment, the CD133-binding agent comprises a bispecific antibody that binds human CD133.

In another embodiment, the CD133-binding agent comprises a phage-Fab, wherein the Fab binds human CD133.

In another embodiment, the CD133-binding agent comprises a phage-scFv that binds human CD133, wherein the scFv binds human CD133.

In still another embodiment, the antibody fragment is a fragment antigen-binding (Fab).

In another embodiment, the CD133-binding agent is (a) a bispecific antibody comprising a CD133-binding single-chain Fab and a non-CD133-binding scFv, (b) a bispecific antibody comprising a CD133-binding Fab and a non-CD133-binding scFv, or (c) a CD133-binding and CD3-binding bispecific antibody.

In yet another embodiment, the CD133-binding agent is (a) a bispecific antibody comprising a CD133-binding single-chain Fab and a CD3-binding scFv or (b) a bispecific antibody comprising a CD133-binding Fab and a CD3-binding scFv.

In another embodiment, the CD133-binding agent is a chimeric antigen receptor (CAR) comprising (i) a CD133-binding antibody variable region and (ii) a CAR signaling domain comprising one or more immune cell receptor signaling domains.

In one embodiment, the CD133-binding agent comprises human antibody constant regions.

In another embodiment, the CD133-binding agent is an IgG molecule.

In a further embodiment, the IgG molecule is an IgG1 molecule.

In another embodiment, the CD133-binding agent is labelled with a detection agent.

The disclosure also provides an immunoconjugate comprising (1) the binding agent described above attached to (2) an effector agent. Optionally, the effector agent is an antineoplastic agent or a toxin.

The disclosure also provides a pharmaceutical composition comprising the CD133-binding agent or the immunoconjugate described above and a carrier.

The disclosure also provides a use of the CD133-binding agent, immunoconjugate or the pharmaceutical composition described above for targeting CD133-expressing cells.

The disclosure also provides a use of the CD133-binding agent, immunoconjugate or the pharmaceutical composition described above for binding CD133-expressing cells.

The disclosure further provides a use of the CD133-binding agent, immunoconjugate or the pharmaceutical composition described above for detecting CD133-expressing cells and/or quantitating levels of cellular CD133 expression.

The disclosure additionally provides a use of the CD133-binding agent or the pharmaceutical composition described herein for reducing levels of CD133 protein in CD133-expressing cells.

In one embodiment, the use of the CD133-binding agent is for detecting and/or quantitating levels of cell-surface expressed CD133 in cells. In another embodiment, the use of the CD133-binding agent is for detecting and/or quantitating total levels of CD133 in cells.

Optionally, detecting CD133-expressing cells and/or quantitating levels of cellular CD133 expression is done by Western blotting, enzyme linked immunosorbent assay (ELISA), immunofluorescence, immunohistochemistry or flow cytometry.

In another embodiment, the cells are cancer cells, optionally CD133-expressing cancer cells or cancer cells detectably expressing CD133.

In yet another embodiment, the cancer cells are melanoma cancer cells, pancreatic cancer cells, brain cancer cells or colorectal cancer cells. In another embodiment, the cancer cells are glioblastoma cells. In another embodiment, the cancer cells are medulloblastoma cells.

The disclosure additionally provides use of a CD133-binding agent, immunoconjugate or the pharmaceutical composition described herein for treating or preventing a cancer.

In one embodiment, the cancer is a CD133-expressing cancer or a cancer detectably expressing CD133. In another embodiment, the cancer is metastatic melanoma, brain, prostate, pancreatic or colon cancer.

In another embodiment, the brain cancer is a glioblastoma, optionally a CD133-expressing glioblastoma or a glioblastoma detectably expressing CD133. In another embodiment, the brain cancer is a medulloblastoma, optionally a CD133-expressing medulloblastoma or a medulloblastoma detectably expressing CD133.

The disclosure also provides a use of a CD133-binding agent comprising (a) a CD133-binding single-chain Fab and a non-CD133-binding scFv, (b) a bispecific antibody comprising a CD133-binding Fab and a non-CD133-binding scFv, or (c) a CD133-binding and CD3-binding bispecific antibody, for treating glioblastoma, optionally CD133-expressing glioblastoma or glioblastoma detectably expressing CD133.

The disclosure also provides a use of a CD133-binding agent comprising (a) a CD133-binding single-chain Fab and a CD3-binding scFv or (b) a bispecific antibody comprising a CD133-binding Fab and a CD3-binding scFv for treating glioblastoma, optionally CD133-expressing glioblastoma or glioblastoma detectably expressing CD133.

The disclosure also provides a use of a CD133-binding agent comprising (a) a CD133-binding single-chain Fab and a non-CD133-binding scFv, (b) a bispecific antibody comprising a CD133-binding Fab and a non-CD133-binding scFv, or (c) a CD133-binding and CD3-binding bispecific antibody, for treating medulloblastoma, optionally CD133-expressing medulloblastoma or medulloblastoma detectably expressing CD133.

The disclosure also provides a use of a CD133-binding agent comprising (a) a CD133-binding single-chain Fab and a CD3-binding scFv or (b) a bispecific antibody comprising a CD133-binding Fab and a CD3-binding scFv for treating medulloblastoma, optionally CD133-expressing medulloblastoma or medulloblastoma detectably expressing CD133.

In one embodiment, the bispecific antibody comprises an amino acid sequence comprising:
    (a) SEQ ID NO: 22 and SEQ ID NO: 23,
    (b) SEQ ID NO: 24 and SEQ ID NO: 25,
    (c) SEQ ID NO: 26,
    (d) SEQ ID NO: 27, or functional variants thereof.

The disclosure also provides a use of a T-cell expressing a chimeric antigen receptor (CAR) described herein for treating glioblastoma, optionally CD133-expressing glioblastoma or glioblastoma detectably expressing CD133.

The disclosure further provides a use of a T-cell expressing a chimeric antigen receptor (CAR) described herein for treating medulloblastoma, optionally CD133-expressing medulloblastoma or medulloblastoma detectably expressing CD133.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DRAWINGS

Embodiments are described below in relation to the drawings in which:

FIG. 1A is a table depicting the results of a cell-based ELISA for CD133-binding of phage-Fab clones and phage-scFv clones selected from Library F or Library G, respectively, for binding to cell-surface CD133 using the Cellect-seq method. Following cell selections, round four output phage for each library was plated for single colonies. These colonies were grown up in an overnight culture and tested for binding to cells by cell-based ELISA. The plates were read and OD450 nm was detected and recorded. The assay measured binding of clones to CD133-overexpressing HEK293-CD133 cells (under "CD133" column headers) vs parental HEK293 cells (under "HEK293" column headers).

FIG. 1B is a histogram depicting a cell-based ELISA for CD133-binding of the three clones (phage-Fab RW03, phage-Fab C12 and phage-Fab F5) which were selected from Library F for binding to cell-surface CD133 using the Cellectseq method, and which were found, after DNA sequencing, to represent the three unique antibody variable regions present in 77 clones found to preferentially bind to HEK293-CD133 cells vs HEK293 cells by at least 1.5-fold.

FIG. 2 is a series of fluorescence photomicrographs depicting that phage-Fab clone RW03 specifically binds to CD133 overexpressing cells. The three clones with unique sequences obtained from the Library F cell-based ELISA were used as probes in an immunofluorescence assay. Phage-Fab clones C12 and F5 are shown to bind to HEK293 cells non-specifically whereas the RW03 clone binds to HEK293-CD133 cells specifically with little background binding to HEK293 cells.

FIG. 3A and FIG. 3B are a histogram and a set of fluorescence photomicrographs, respectively, depicting that purified Fab RW03 specifically binds to HEK293-CD133 as opposed to HEK293 cells. Expressed and purified Fab RW03 was tested for binding by cell-based ELISA (FIG. 3A) and immunofluorescence (IF) assay (FIG. 3B).

FIG. 4A and FIG. 4B are line graphs depicting binding curves for binding of IgG RW01 and IgG RW03, respectively, to HEK293-CD133 cells, for estimation of binding affinity (EC50). Cells were incubated with stepwise dilutions of either IgG RW01 or IgG RW03 to determine a half-maximal binding curve for the antibodies. Using the SigmaPlot graphing software the EC50 for IgG RW01 was calculated as 2.5 nM (FIG. 4A) and the EC50 for IgG RW03 was calculated as 0.5 nM (FIG. 4B).

Figure 7:
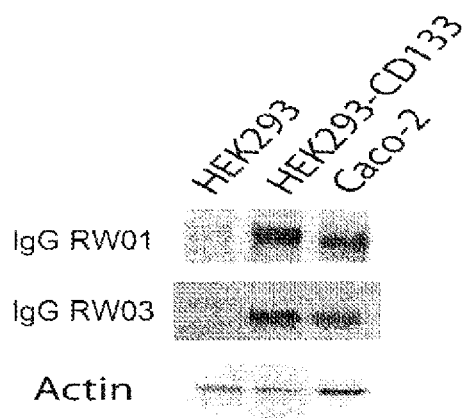

FIG. 7 is a set of photographs of a Western blot analysis depicting that IgG RW01 and IgG RW03 can be used to detect denatured CD133/cellular CD133 in colorectal cancer cells, as shown via Western blot analysis. Whole cell lysates of HEK293, HEK293-CD133 and Caco-2 cells were probed with IgG RW01 and IgG RW03 and binding was detected with an anti-human HRP-conjugated secondary antibody. Beta-actin was used as a loading control.

Figure 8:
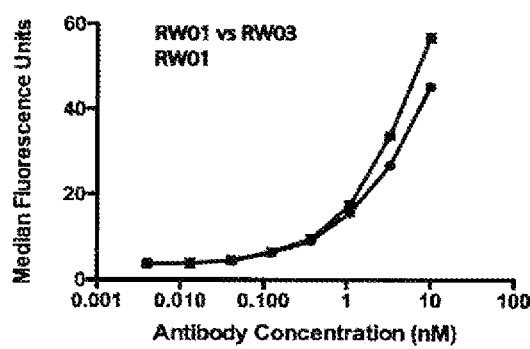
Figure 8:
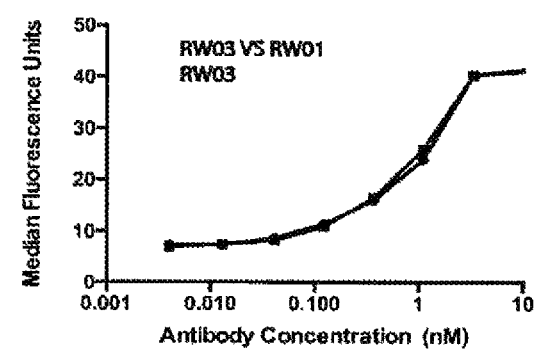

FIG. 8 shows that Fab comprising antibody variable region RW01 and Fab comprising antibody variable region RW03 do not compete with IgG RW03 and IgG RW01, respectively, for binding to CD133. RW01 and RW03 were tested for binding to CD133 in a competitive flow cytometry experiment. In (a) cells were incubated with stepwise dilutions of IgG RW01 (circles) or IgG RW01 in the presence of Fab RW03 (squares). Similarly, in (b) cells were incubated stepwise with dilutions of IgG RW03 (circles) or IgG RW03 in the presence of Fab RW01 (squares).

Figure 9:
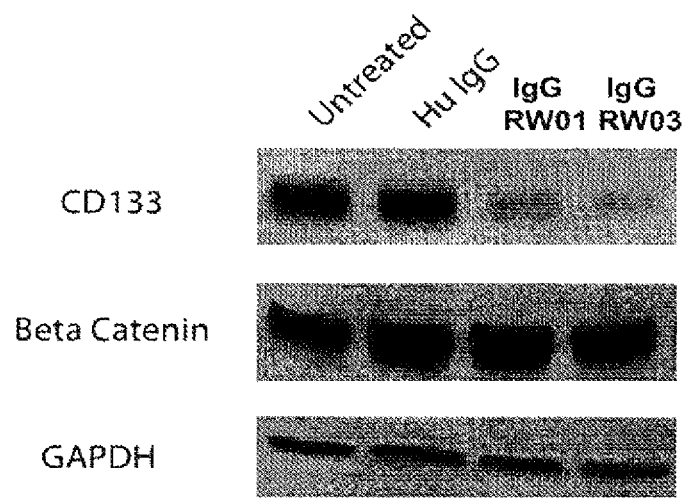

FIG. 9 is a set of photographs of a Western blot analysis depicting that treatment with IgG RW01 or IgG RW03 significantly reduces total cellular levels of CD133 protein in Caco-2 colorectal cancer cells. Caco-2 cells were incubated with the indicated antibody for 24-hours at 37° C., whole cell lysates were prepared and probed with AC133 anti-CD133 antibody. Anti-human IgG (H+L) antibody was used as negative antibody control, and GAPDH was used as a loading control.

Figure 10A:
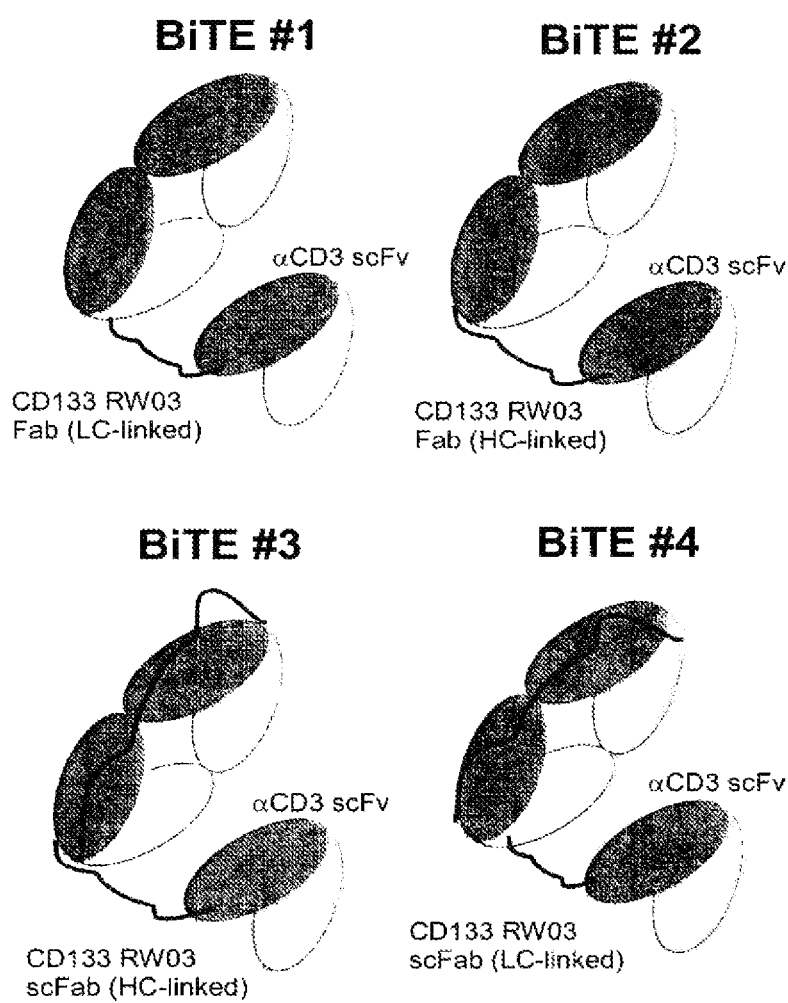

FIG. 10A is a set of schematic diagrams depicting the configurations of BiTE #1, BiTE #2, BiTE #3 and BiTE #4.

Figure 10B:
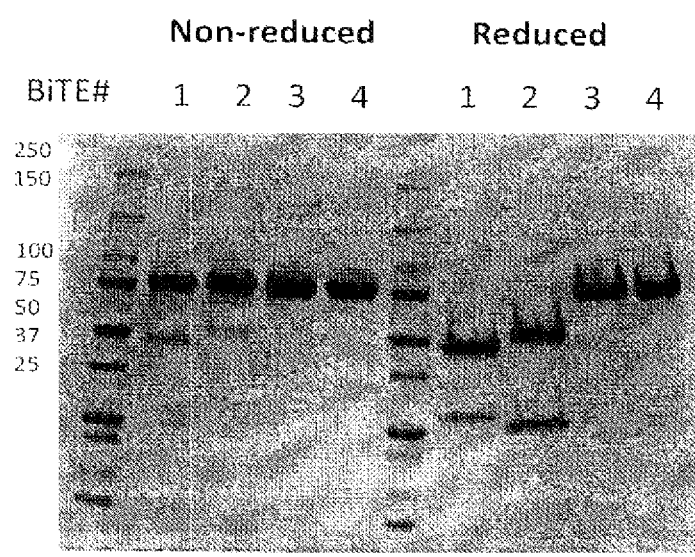

FIG. 10B is a photograph of a Western blot analysis depicting that BiTE #1, BiTE #2, BiTE #3 and BiTE #4 could each be expressed and purified from HEK293 cells by transient transfection protocol.

Figure 11A:
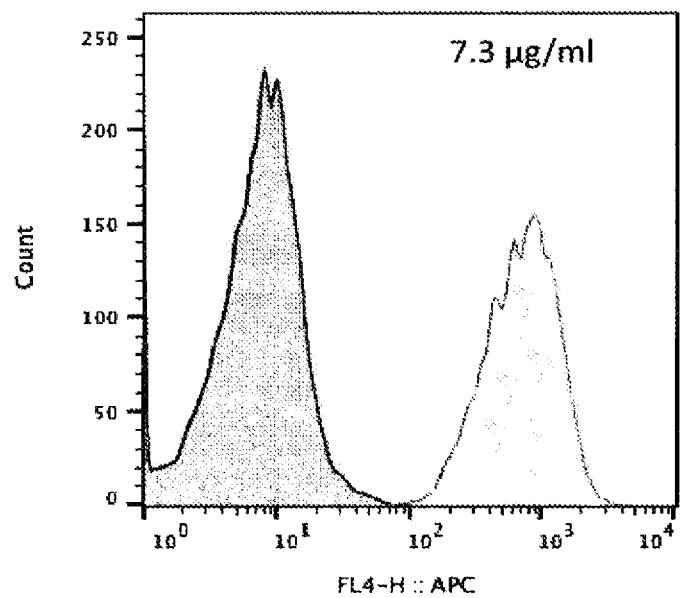
Figure 11A:
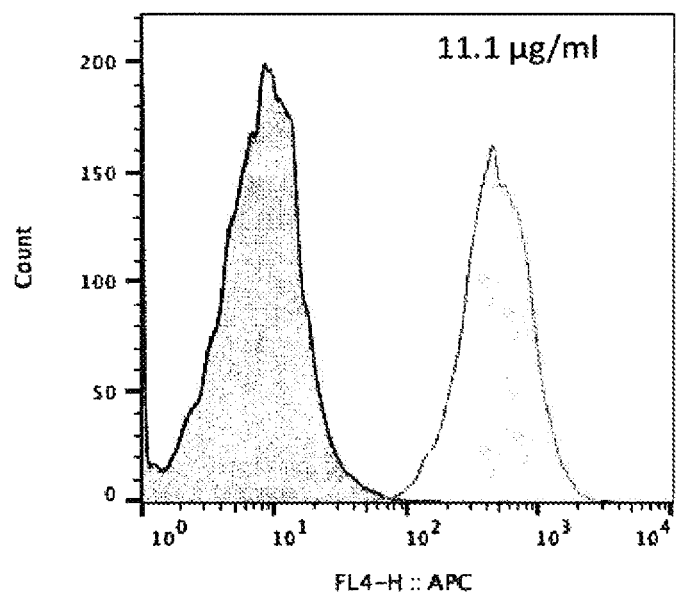
Figure 11B:
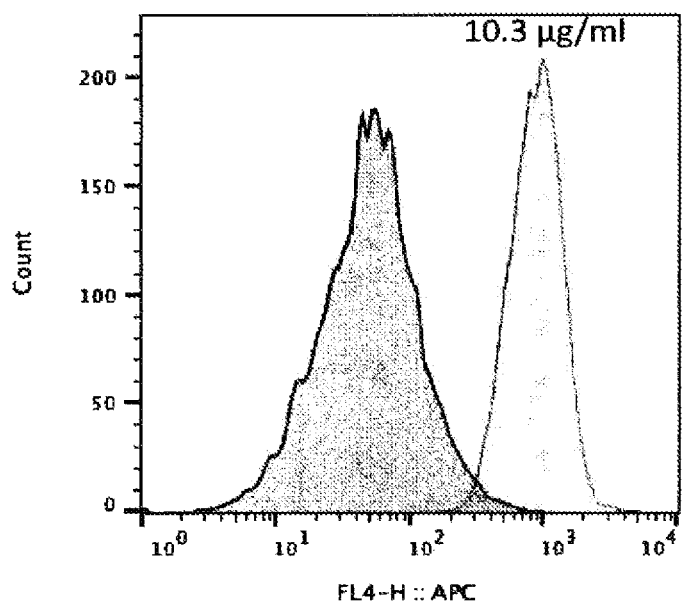
Figure 11B:
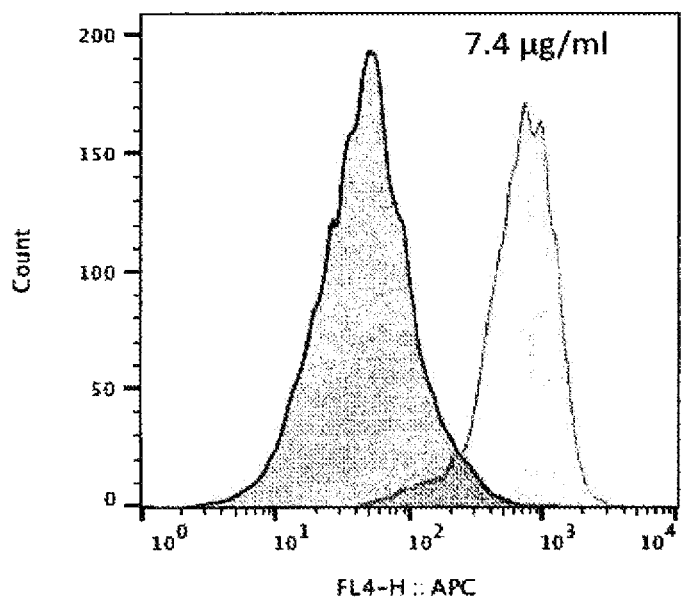

FIG. 11A and FIG. 11B are sets of fluorescence histograms depicting that BiTE #1 (FIG. 10A), BiTE #2 (FIG. 10A), BiTE #3 (FIG. 10B) and BiTE #4 (FIG. 10B) each binds to HEK293-CD133 cells significantly more than to the parental HEK293 cells, even at concentrations as low as 0.073-0.11 microgram/ml, as determined via flow cytometry. The BiTE concentrations employed are indicated for each histogram. In each histogram the rightmost peak represents binding to HEK293-CD133 cells and the leftmost peak represents binding to the parental HEK293 cells.

Figure 12:
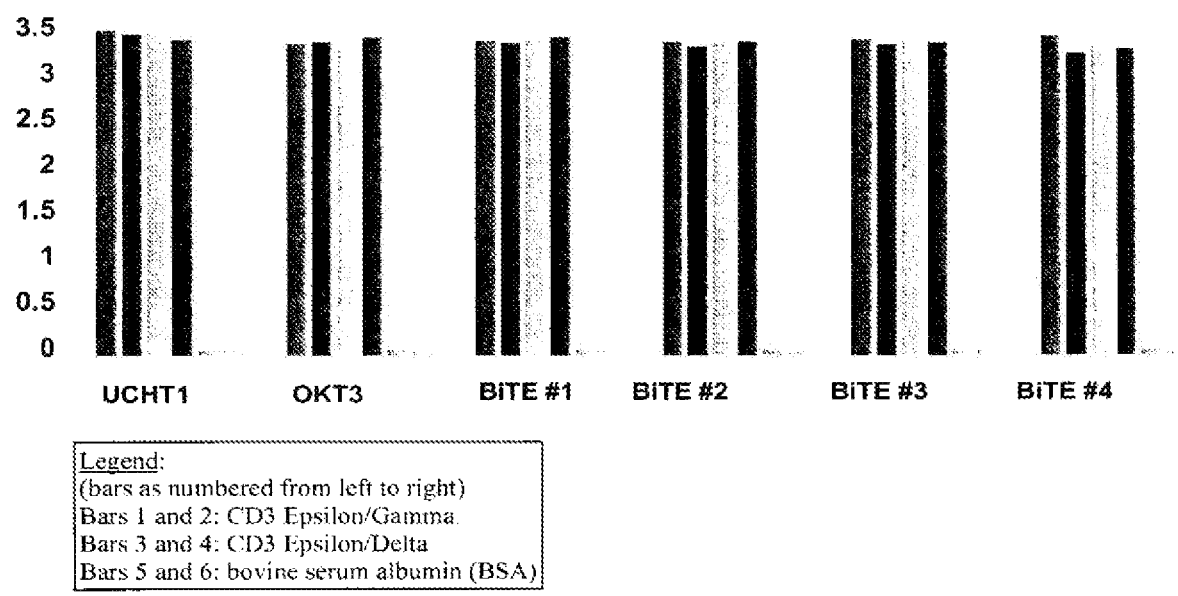

FIG. 12 is a histogram of ELISA results depicting that BiTE #1, BiTE #2, BiTE #3 and BiTE #4 each binds to CD3 in the form of CD3 epsilon/gamma and CD3 epsilon/delta. Anti-CD3 antibodies UCHT1 and OKT3 were used as positive antibody controls and BSA was used as no antibody control.

Figure 13:
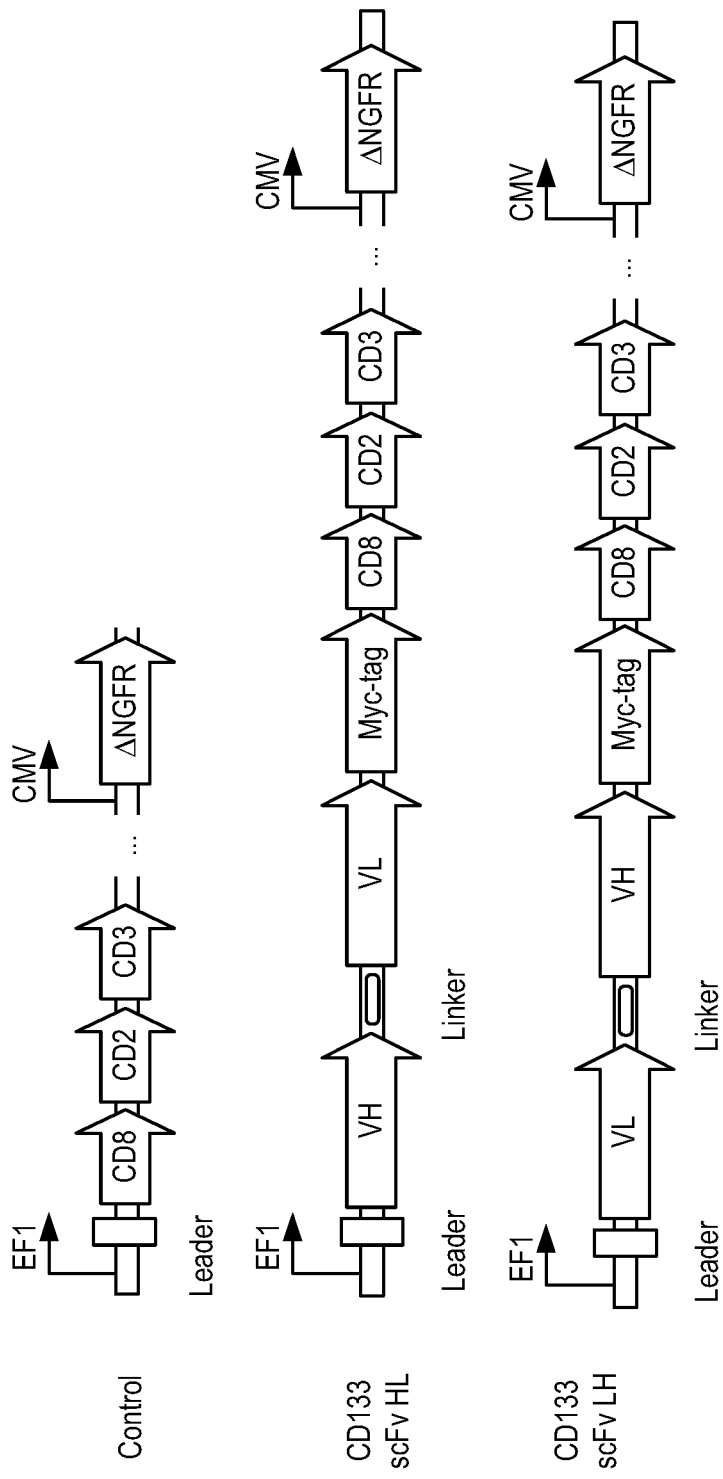

FIG. 13 depicts constructs for the generation of CD133-specific chimeric antigen receptors (CARs).

Figure 14:
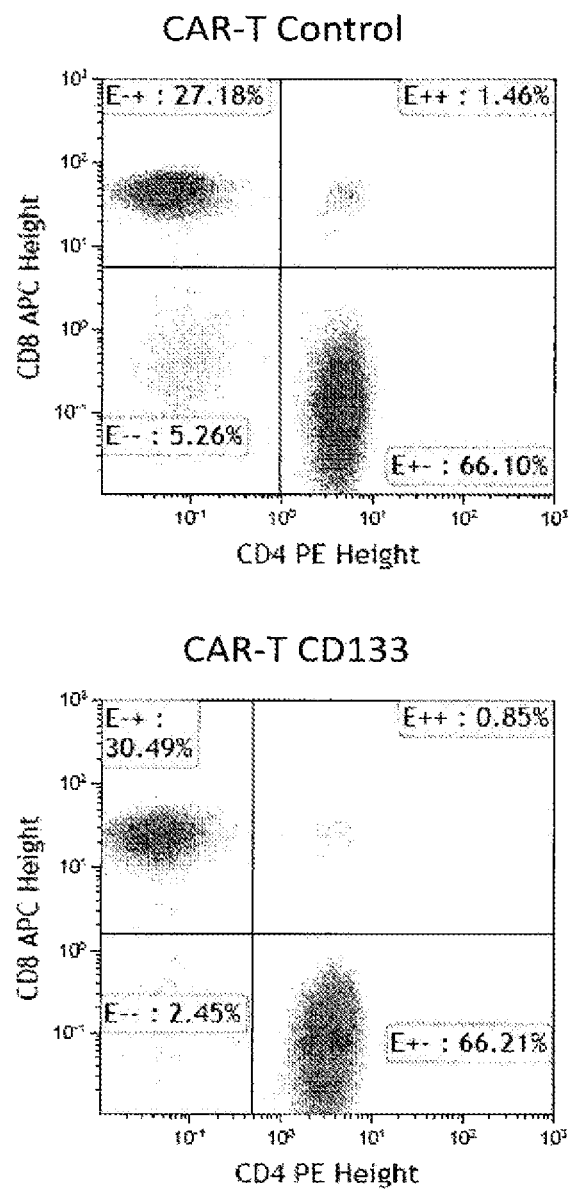

FIG. 14 shows the characterization of CAR-T cells.

Figure 15:
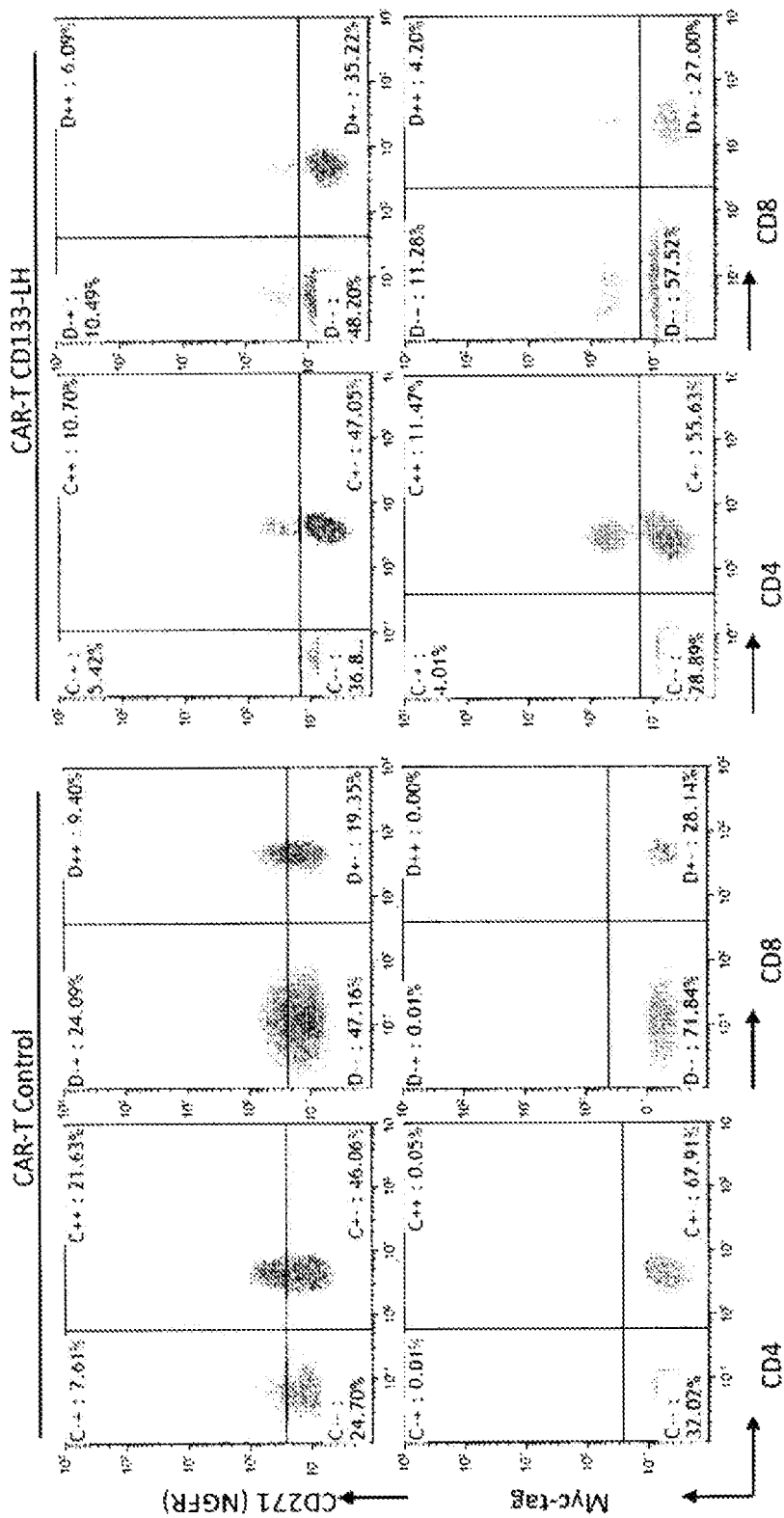

FIG. 15 shows the validation of CD133-specific CAR-T cells.

Figure 16:
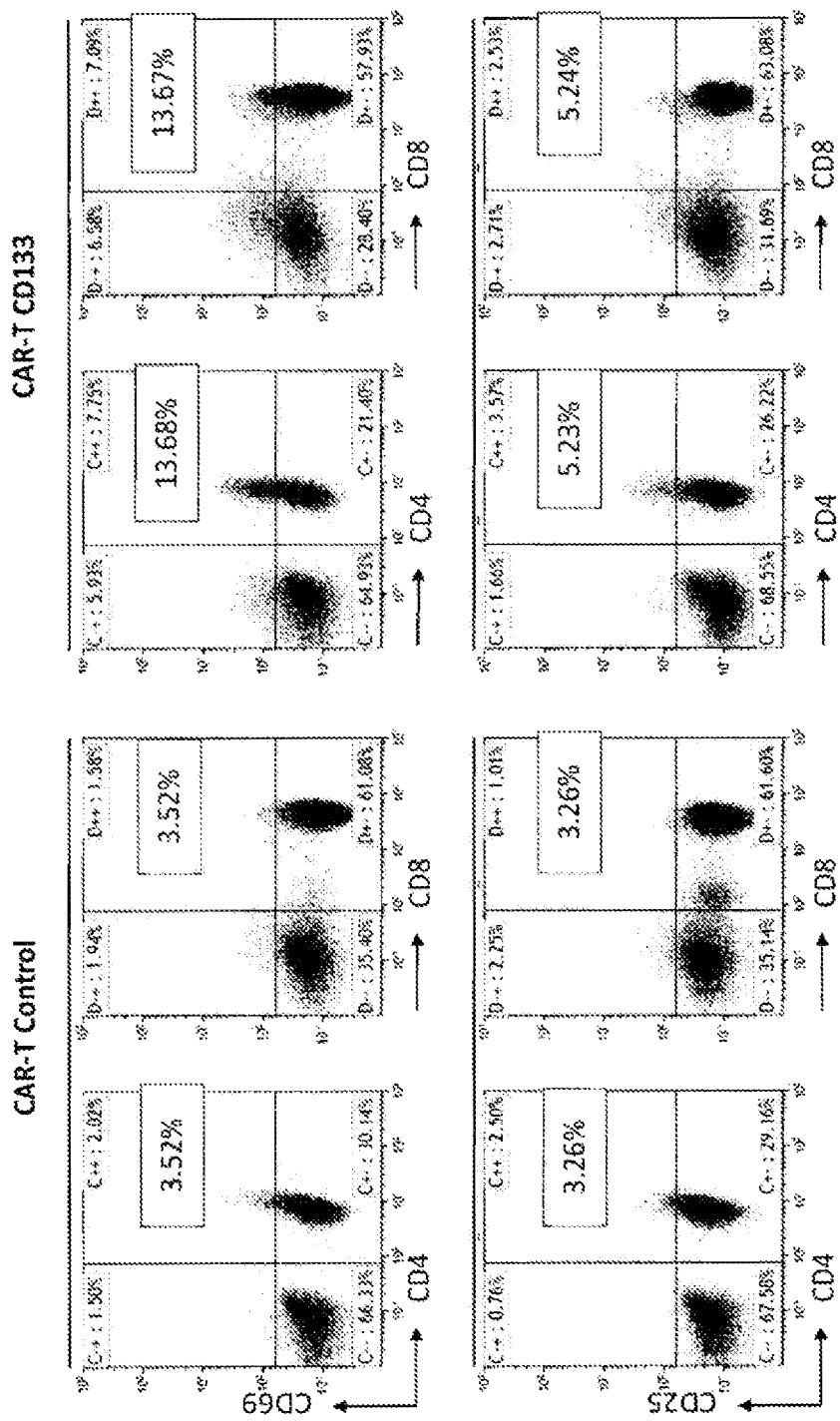

FIG. 16 shows that CD133-specific CAR-T cells are activated in presence of CD133+ human GBM cells.

Figure 17:
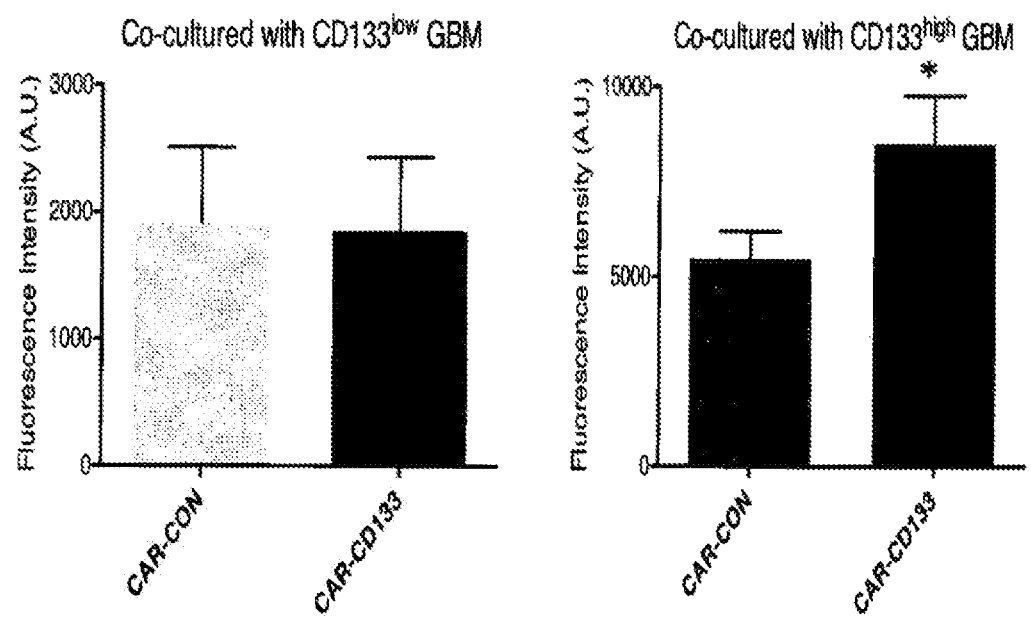

FIG. 17 shows that activated CD133-specific CAR-T cells have enhanced proliferation ability and specifically induce CD133-positive GBM cell death and CD133-positive medulloblastoma cell death. CAR-T cells were co-cultured with $CD133^{high}$ and $CD133^{low}$ GBM cells as well as $CD133^{high}$ medulloblastoma cells. Flow cytometry was based on live-dead staining with IR-dye.

Figure 18:
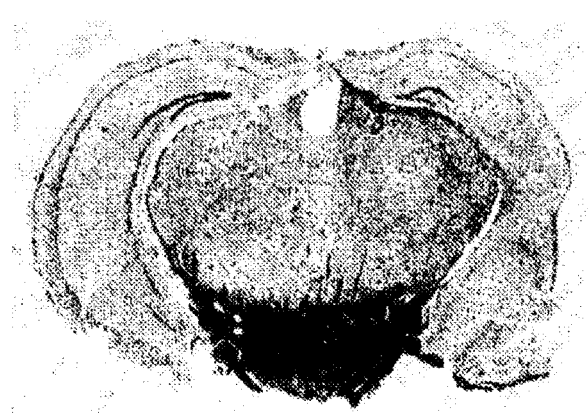
Figure 18:
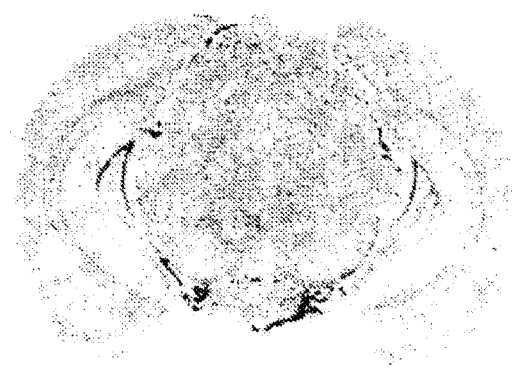
Figure 18:
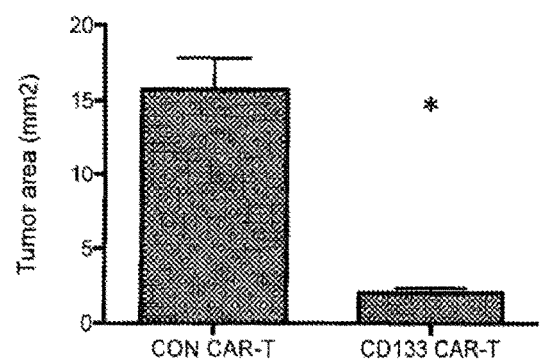

FIG. 18A-C shows that CD133-specific T cells induce GBM tumor regression in vivo. Treatment was delivered intracranially at a dose of 1 million×2 doses (2 week).

Figure 19:
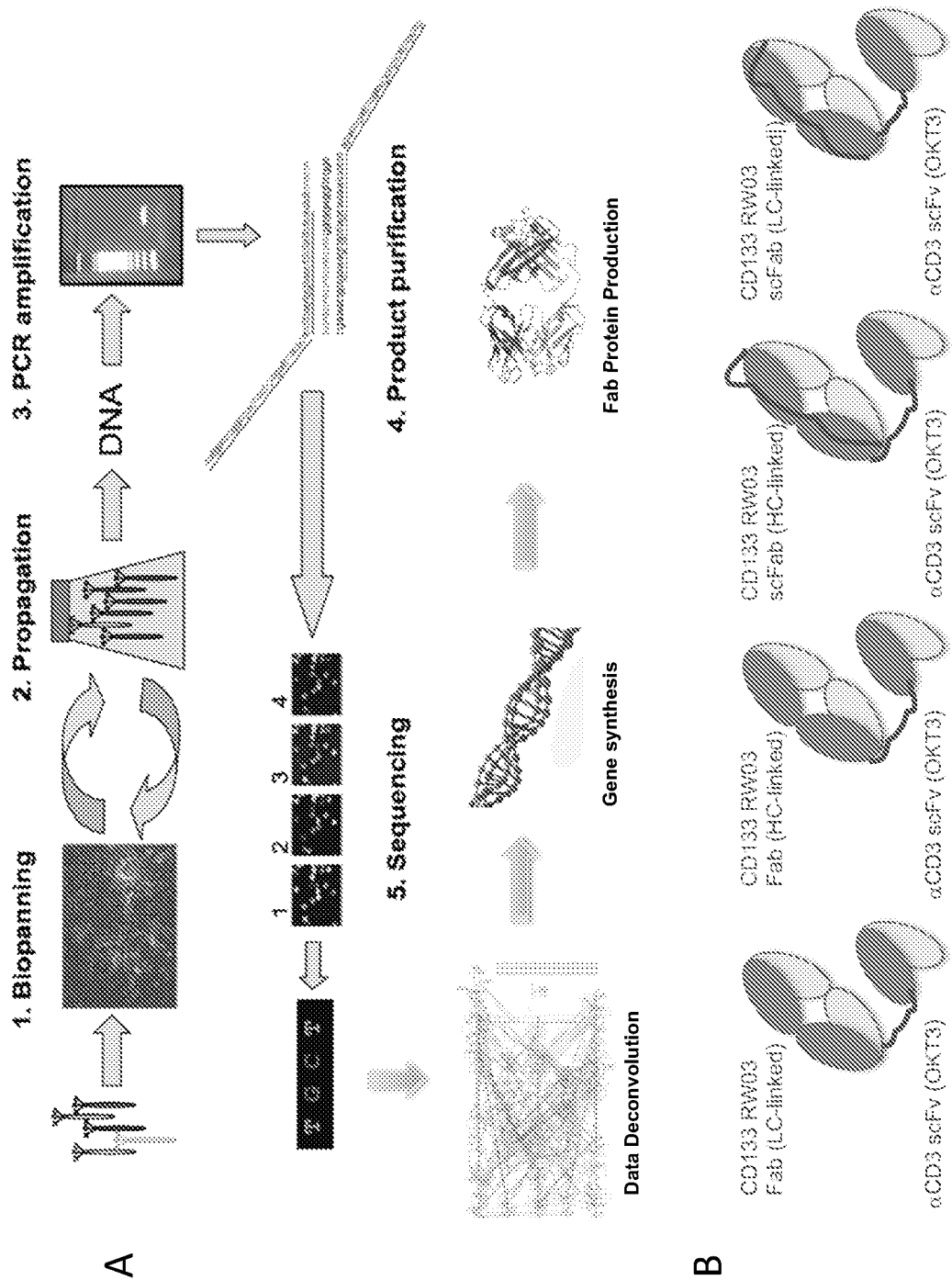

FIGS. 19A and B shows the development of CD133×CD3 BiTEs.

Figure 20A:
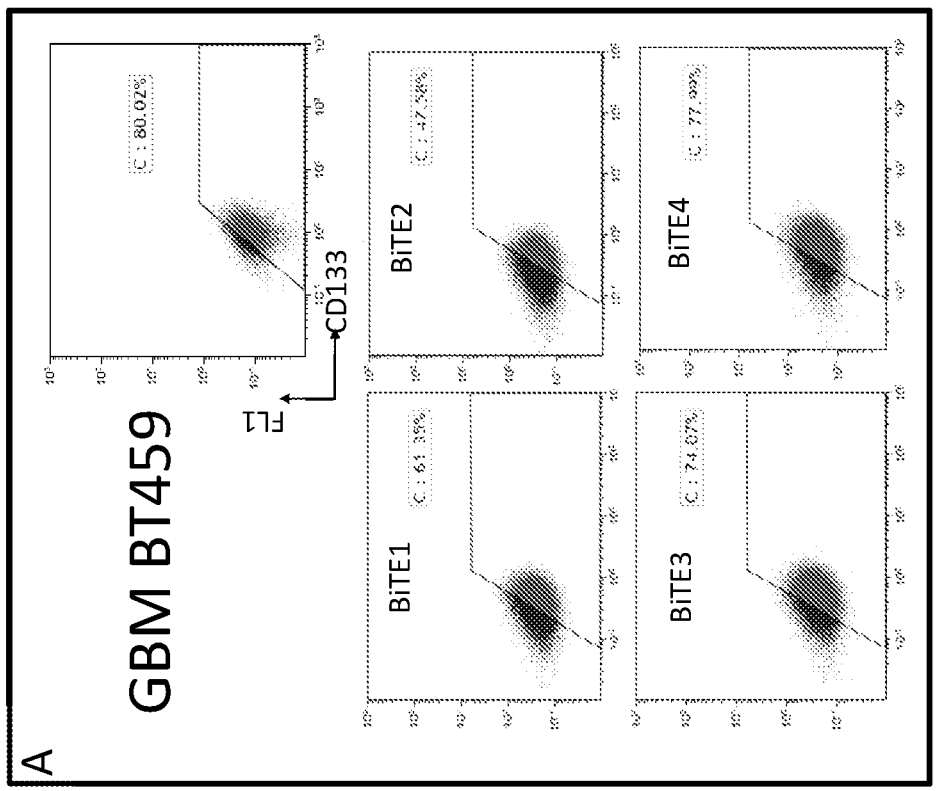

FIGS. 20A and B shows that CD133×CD3 BiTEs bind to CD133+ GBM tumor cells and CD3+T lymphocytes.

Figure 21:
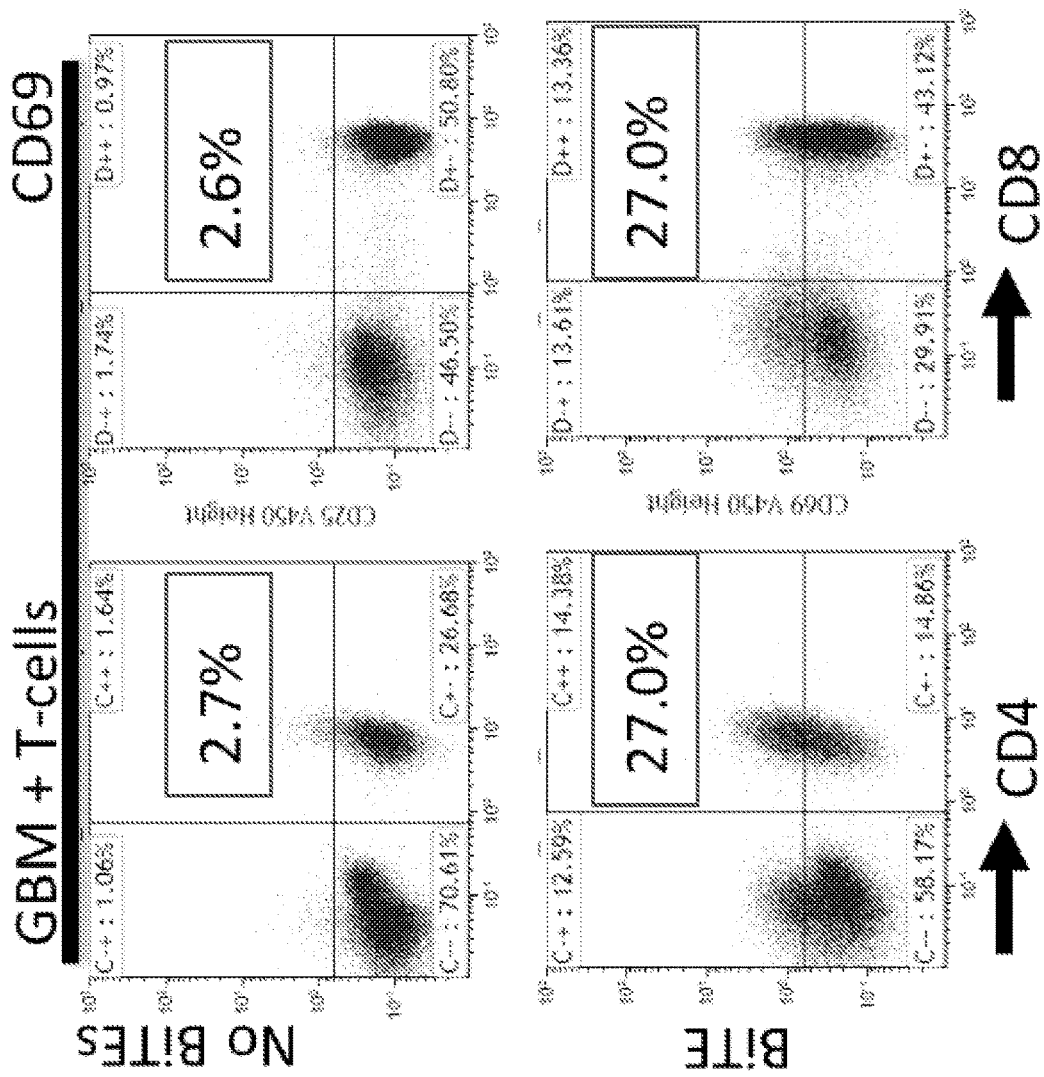

FIG. 21 shows that CD133-specific BiTEs activate T cells.

Figure 22:
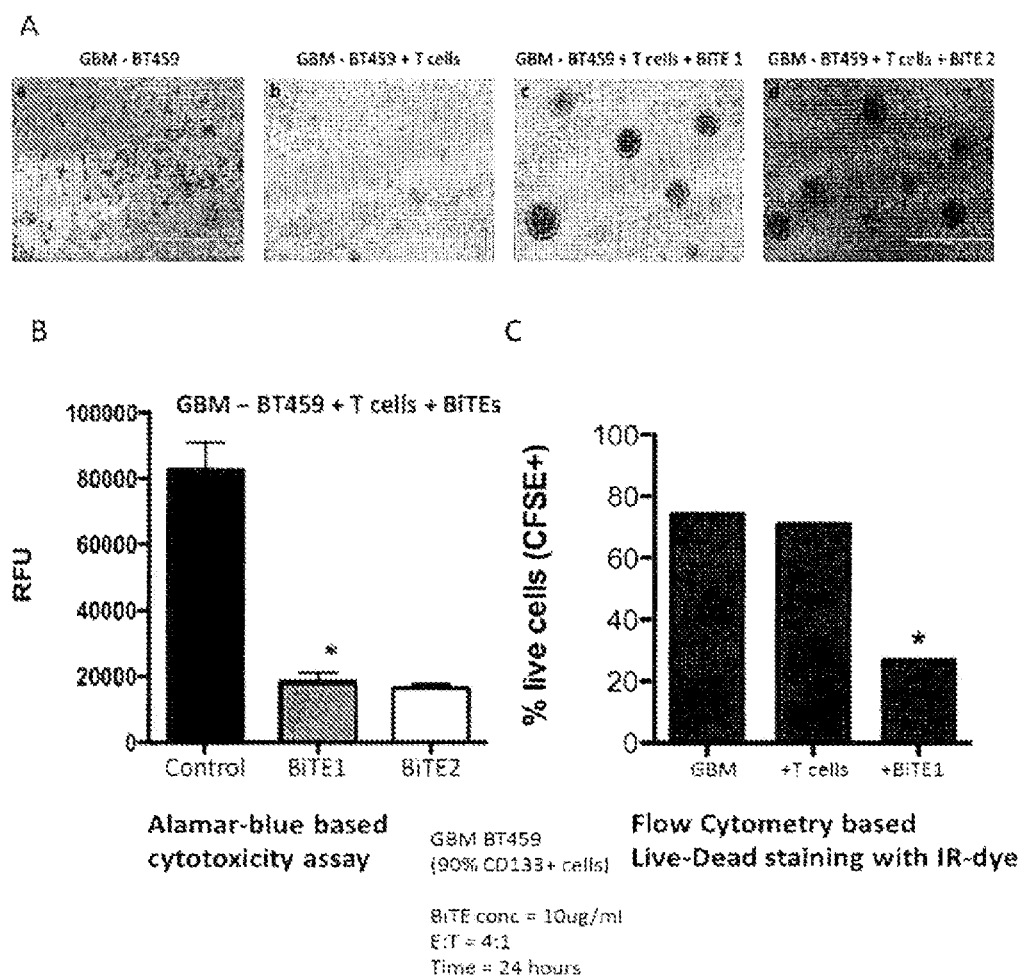

FIG. 22A-C shows that CD133-specific BiTEs recruit T cells to CD133+ human GBM cells and cause cell death.

FIG. 23A-D shows a CD133×CD3 BiTE mediated anti-tumor response.

DESCRIPTION OF VARIOUS EMBODIMENTS

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Compositions of Matter:

The present inventors have provided novel synthetic antibody variable regions which are capable of specifically binding surface expressed/native human CD133 and also denatured human CD133, and which specifically bind human CD133 with a dissociation constant ($K_D$) in the subnanomolar/nanomolar range (see Examples 3 and 6, below).

The inventors have particularly provided CD133-binding phage-scFv clone RW01 wherein the scFv comprises CD133-binding antibody variable region RW01, and CD133-binding phage-Fab clone RW03 wherein the Fab comprises CD133-binding antibody variable region RW03. These clones were selected from phage display libraries for their capacity to specifically bind CD133-expressing cells, as initially confirmed via enzyme-linked immunosorbent assay (ELISA; see Examples 1 and 2, below). The inventors have further particularly provided that CD133-binding antibody variable region RW01 comprises an antibody light chain variable domain corresponding to the Asp1 to Lys106 segment of SEQ ID NO: 2, wherein the amino acid sequences of the light chain CDR1, light chain CDR2 and light chain CDR3 thereof correspond to SEQ ID NO: 6, SEQ ID NO: 7, and SEQ ID NO: 8, respectively (see Example 2, below). The inventors have additionally provided that antibody variable region RW01 comprises an antibody heavy chain variable domain corresponding to the Glu1 to Thr120 segment of SEQ ID NO: 3, wherein the amino acid sequences of the heavy chain CDR1, heavy chain CDR2 and heavy chain CDR3 thereof correspond to SEQ ID NO: 9, SEQ ID NO: 10, and SEQ ID NO: 11, respectively, and wherein the (framework region) residues at positions 39, 55 and 66 are Met, Ser and Tyr residues (see Example 2, below).

The inventors have yet further provided that CD133-binding antibody variable region RW03 comprises an antibody light chain variable domain corresponding to the Asp1 to Lys109 segment of SEQ ID NO: 4, wherein the amino acid sequences of the light chain CDR1, light chain CDR2 and light chain CDR3 thereof correspond to SEQ ID NO: 12, SEQ ID NO: 13, and SEQ ID NO: 14, respectively (see Example 2, below). The inventors have still further provided that antibody variable region RW03 comprises an antibody heavy chain variable domain corresponding to the Glu1 to Ser118 segment of SEQ ID NO: 5; wherein the amino acid sequences of the heavy chain CDR1, heavy chain CDR2 and heavy chain CDR3 thereof correspond to SEQ ID NO: 15, SEQ ID NO: 16, and SEQ ID NO: 17, respectively; and wherein the (framework region) residues at positions 39, 55 and 66 are Ile, Tyr and Tyr residues, respectively; (see Example 2, below).

The inventors have further particularly provided that IgG1 antibodies "IgG RW01" and "IgG RW03", which comprise CD133-binding antibody variable region RW01 and CD133-binding antibody variable region RW03, respectively, can be used to: (i) specifically bind and detect cell surface CD133 in pancreatic cancer cell lines and colorectal cancer cell lines, as shown via flow cytometry analysis (see Example 4, below); (ii) specifically bind, detect and subcellularly localize cellular CD133 in CD133-expressing cells, as shown via immunofluorescence analysis (see Example 5, below); (iii) detect denatured CD133 in whole cell lysate of colorectal cancer cells, as shown via Western blot analysis (see Example 6, below); and (iv) significantly reduce total cellular CD133 protein levels in a colorectal cancer cell line (see Example 8, below). The inventors disclose that antibody IgG RW01 comprises a light chain having the amino acid sequence of SEQ ID NO: 2 and a heavy chain having the amino acid sequence of SEQ ID NO: 3, and antibody IgG RW03 comprises a light chain having the amino acid sequence of SEQ ID NO: 4 and a heavy chain having the amino acid sequence of SEQ ID NO: 5 (Example 2). The inventors have still further disclosed that Fab comprising antibody variable region RW01 and Fab comprising antibody variable region RW03 do not compete with IgG RW03 and IgG RW01, respectively, for binding to CD133 (Example 7, below).

The present inventors have also described a chimeric antigen receptor (CAR) T-cell-based strategy that specifically targets CD133+ GBM cells. CD133-specific CAR-expressing T cells were activated in presence of CD133$^{high}$ GBM cells, and showed increased surface expression of activation markers CD69 and CD25. Both, CD4+ and CD8+ CD133-specific CAR-T cells showed upregulation in surface expression levels of activation markers. The inventors further demonstrated CAR-T cell-induced cytotoxicity against treatment-resistant and evasive CD133+ GBM BTICs (Example 10, below).

The inventors have further particularly disclosed that multiple configurations of a bispecific antibody/bispecific T cell engager (BiTE) comprising a scFv which binds the T cell coreceptor CD3, and further comprising a Fab or single-chain Fab (scFab) incorporating CD133-binding antibody variable region RW03, can specifically bind both CD133-positive cells and CD3 (see Example 9, below). The inventors also showed that a recombinant CD133×CD3 bispecific T-cell engager (BiTE) redirects human polyclonal T cells to CD133+ GBM cells, inducing a potent anti-tumor response (see Example 11, below).

The CD133 molecule is a transmembrane protein having an extracellular N-terminal region, five transmembrane domains with alternating short and long intracellular and extracellular domains, respectively, and an intracellular C-terminal region. As used herein, CD133 may be from any species or source and includes isoforms, analogs, variants or functional derivatives of such a CD133 protein. In one embodiment, CD133 is human CD133. The human CD133 gene or protein may have any of the known published sequences for CD133 which can be obtained from public sources such as GenBank. An example of such a protein sequence includes, but is not limited to the sequence set out as SEQ ID NO: 1. Human CD133 is alternately referred to in the art as Prominin-1.

CD133-Binding Agents

Accordingly, the disclosure provides a CD133-binding agent which specifically binds cell surface-expressed/native CD133 and which specifically binds denatured CD133.

As used herein, a CD133-binding agent which "specifically binds cell surface-expressed/native CD133" is an agent which binds CD133-expressing cells. Cells expressing CD133 can be identified as such, e.g. via flow cytometric analysis, e.g. as described in Example 4. Alternately, a CD133-binding agent which "specifically binds cell surface-expressed/native CD133" is an agent which binds CD133-expressing cells expressing CD133 at undetectable levels, e.g. at levels below the limit of detection of an assay such flow cytometric analysis. As used herein, a CD133-binding agent which "specifically binds denatured CD133" is an agent which binds CD133 in a sample of denatured whole cell protein of CD133-expressing cells as opposed to the other polypeptides in the sample (as determined, e.g. via Western blot analysis, e.g. as described in Example 6). The terms "immunoreacts with CD133", or "is directed against CD133", or is characterized as "anti-CD133" are also used herein for the same purpose.

In one embodiment, the CD133-binding agent specifically binds a CD133 epitope bound by an antibody comprising a light chain having the amino acid sequence of SEQ ID NO: 2 and a heavy chain having the amino acid sequence of SEQ ID NO: 3 (i.e. antibody IgG RW01), and/or specifically binds a CD133 epitope bound by an antibody comprising a light chain having the amino acid sequence of SEQ ID NO: 4 and a heavy chain having the amino acid sequence of SEQ ID NO: 5 (i.e. antibody IgG RW03). In an embodiment, the CD133 epitope is a human CD133 epitope.

As used herein, the term "epitope" refers to the specific site or specific combination of sites/amino acids on an antigen that are bound by antibody IgG RW01 and/or antibody IgG RW03, for example, unmodified or modified (e.g. post-translationally modified, e.g. glycosylated) amino acid residues of human CD133, the minimal polypeptide segment of human CD133 encompassing these amino acid residues, or any combination of polypeptide segments of human CD133 encompassing these amino acid residues. Epitopic determinants usually consist of molecules such as amino acids or sugar side chains and usually have specific three-dimensional structural characteristics, as well as specific charge characteristics.

As used herein, unless otherwise specified, an antibody or a bivalent antibody fragment (e.g. F(ab')$_2$) referred to as comprising "a" specific light chain or "a" specific heavy chain in the singular refers to an antibody or a bivalent antibody fragment in which both light chains or both heavy chains are identical, respectively.

Embodiments of the CD133-binding agent include any type of CD133-binding molecule, macromolecule, substance, compound, material, composition, or complex, without limitation.

In one embodiment, the CD133-binding agent is a polypeptide. In other embodiments, the CD133-binding agent is a non-polypeptidic agent, such as a CD133-binding nucleic acid or a CD133-binding organic compound. The CD133-binding agent may be monomeric or multimeric. The CD133-binding agent may be polymeric or non-polymeric. Alternatively, the CD133-binding agent may be an engineered polypeptide (e.g. a naturally occurring polypeptide engineered to have a modified amino acid sequence; or a chimeric polypeptide engineered to comprise two or more naturally occurring amino acid sequences; or an engineered polypeptide selected from a library of engineered polypeptides having randomized amino acid sequences), or a chemically modified polypeptide.

In one embodiment, the CD133-binding agent comprises a CD133-binding antibody variable region.

As used herein, a CD133-binding antibody variable region is a combination of an antibody heavy chain variable domain and an antibody light chain variable domain, where the antibody heavy chain variable domain and the antibody light chain variable domain form an antigen-binding site that specifically binds CD133.

The CD133-binding agent is optionally an antibody, an antigen-binding fragment of an antibody, or an agent comprising a CD133-binding antibody variable region.

As used herein, and unless otherwise specified, the term "antibody" refers to an immunoglobulin (Ig) molecule. The basic antibody structural unit is known to comprise a tetramer. Each tetramer is composed of two identical pairs of polypeptide chains, each pair having one light ("L") (about 25 kDa) and one heavy ("H") chain (about 50-70 kDa). The amino-terminal portion of each chain includes a variable region of about 100 to 110 or more amino acids primarily responsible for antigen recognition, and described in more detail below. The carboxy-terminal portion of each chain defines a constant region primarily responsible for effector function. The term "antigen-binding site" or "binding portion" refers to the part of the binding protein that participates in antigen binding. In an antibody, the antigen binding site is formed by amino acid residues of the N-terminal variable ("V") regions of the heavy and light chains. Three highly divergent stretches within the V regions of the heavy and light chains, referred to as "hypervariable regions", are interposed between more conserved flanking stretches known as "framework regions", or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs". All CDRs and framework regions (FRs) disclosed herein, amino acid sequences of CDRs and FRs disclosed herein, and CDR-encoding or FR-encoding nucleic acid sequences disclosed herein, are intended to be defined in accordance with IMGT numbering (Lefranc et al., 2003). Another system alternately employed in the art for such definitions is that of Kabat numbering (Kabat et al., 1991).

The CD133-binding agent may be an antibody, such as a human antibody, containing engineered variable regions (e.g. containing variable regions selected from a phage display library displaying engineered antibody variable regions, e.g. a phage-Fab library or a phage-scFv library, e.g. as described in Example 1), or a chimeric antibody comprising human constant regions and an antibody variable region of a non-human mammal. The CD133-binding agent may be a humanized antibody, e.g. an antibody comprising human constant regions, human variable region framework regions, and CD133-binding CDRs generated in a non-human mammal. The non-human mammal may be a rodent, such as a mouse, rat, rabbit, guinea pig or hamster. Alternately, the non-human mammal may be an ungulate, such as a camelid or a bovid. The CD133-binding agent may be an antibody comprising heavy chain constant regions belonging to any type of class, or subclass. The CD133-binding agent may comprise any type of light chain.

In one embodiment, the CD133-binding agent is a human antibody, such as an IgG1 antibody, wherein the heavy chain constant regions are gamma1 heavy chain constant regions. In other embodiments, the CD133-binding agent is a human antibody, such as an IgA1, IgA2, IgD, IgG2, IgG3, IgG4, IgE or IgM antibody, wherein the heavy chain constant regions are alpha1, alpha2, delta, gamma2, gamma3, gamma4, epsilon or mu heavy chain constant regions, respectively.

In yet a further embodiment, the CD133-binding agent is an antibody wherein the light chains comprise human kappa light chain constant domains, or wherein the light chains are human kappa light chains. Alternately, the CD133-binding agent is an antibody wherein the light chains comprise human lambda light chain constant domains, or wherein the light chains are human lambda light chains.

In still a further embodiment the CD133-binding agent is an antibody comprising human gamma1 heavy chain constant regions and human kappa light chains.

Embodiments of CD133-binding agents of the present disclosure further include, but are not limited to, fragment antigen-binding (Fab), single-chain Fv (scFv), single-chain Fab (scFab), Fab', Fv, chemically linked F(ab')$_2$, dsFv, dsFv', sc(Fv)$_2$, ds-scFv, (dsFv)2, scFv-Fc, scFv-based chimeric antigen receptors (CARs), Fab-based CARs, scFab-based CARs, single-chain immunoglobulin (e.g. sclgG), single-domain antibody (sdAb, nanobody), scFv-Fc, minibody (scFv-CH3), diabody, tribody, tetrabody, multimeric antibody (e.g. scFv dimer, bivalent diabody), multispecific antibody (e.g. bispecific antibody, trispecific antibody, di-scFv, tri-scFv, bispecific Fab$_2$, trispecific Fab$_2$, trispecific triabody, trispecific Fab$_3$), multimeric/multispecific antibody (e.g. scFv dimer, bispecific diabody, dsFv-dsFv'), heavy-chain antibody, Fab$_3$, divalent VHH, pentavalent VHH (pentabody), (scFv-SA)$_4$ and, [sc(Fv)2]$_2$.

In another embodiment, the CD133-binding agent is a phage displaying a polypeptide comprising a CD133-binding antibody variable region, such as a phage-Fab or phage-scFv (see Examples 1 and 2, below).

Embodiments of CD133-binding agents of the present disclosure still further include CD133-binding nucleic acid aptamers (e.g. RNA aptamers or DNA aptamers; see, e.g. Lipi et al., 2016), peptide aptamers (see, e.g. Parashar, 2016), and chemically synthesized agents (e.g. synthetic antibody mimics; see, e.g. McEnaney et al., 2014).

In another embodiment, the CD133-binding agent is a peptide analog. Peptide analogs are commonly used in the pharmaceutical industry as non-peptide drugs with properties analogous to those of the template peptide. These types of non-peptide compound are termed "peptide mimetics" or "peptidomimetics" (see, e.g. Fauchere, 1986); Veber and Freidinger, 1985; and Evans et al., 1987). Such compounds are often developed with the aid of computerized molecular modeling. Peptide mimetics that are structurally similar to biologically useful peptides may be used to produce an equivalent biological effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH2NH—, —CH$_2$S—, —CH2-CH2-, —CH═CH— (cis and trans), —COCH2-, CH(OH)CH2- and —CH2SO—, by methods well known in the art. Systematic substitution of one or more amino acids of a consensus sequence with a D-amino acid of the same type (e.g. D-lysine in place of L-lysine) may be used to generate more stable peptides. In addition, constrained peptides comprising a consensus sequence or a substantially identical consensus sequence variation may be generated by methods known in the art (see, e.g. Rizo and Gierasch, 1992), for example, by adding internal cysteine residues capable of forming intramolecular disulfide bridges which cyclize the peptide.

In an embodiment, the CD133-binding agent comprises antibody variable region RW01, which comprises (a) an antibody light chain variable domain (SEQ ID NO: 28) corresponding to the Asp1 to Lys106 segment of SEQ ID NO: 2, wherein the amino acid sequences of the light chain CDR1, light chain CDR2 and light chain CD3 thereof correspond to SEQ ID NO: 6, SEQ ID NO: 7, and SEQ ID NO: 8, respectively (see Example 2, below) and (b) an antibody heavy chain variable domain (SEQ ID NO: 29) corresponding to the Glu1 to Thr120 segment of SEQ ID NO: 3, wherein the amino acid sequences of the heavy chain CDR1, heavy chain CDR2 and heavy chain CDR3 thereof correspond to SEQ ID NO: 9, SEQ ID NO: 10, and SEQ ID NO: 11, respectively, and wherein the (framework region) residues at positions 39, 55 and 66 are Met, Ser and Tyr residues (see Example 2, below).

In a further embodiment, the CD133-binding agent comprises antibody variable region RW03, which comprises (a) an antibody light chain variable domain (SEQ ID NO: 30) corresponding to the Asp1 to Lys109 segment of SEQ ID NO: 4, wherein the amino acid sequences of the light chain CDR1, light chain CDR2 and light chain CD3 thereof correspond to SEQ ID NO: 12, SEQ ID NO: 13, and SEQ ID NO: 14, respectively (see Example 2, below) and (b) an antibody heavy chain variable domain (SEQ ID NO: 31) corresponding to the Glu1 to Ser118 segment of SEQ ID NO: 5; wherein the amino acid sequences of the heavy chain CDR1, heavy chain CDR2 and heavy chain CDR3 thereof correspond to SEQ ID NO: 15, SEQ ID NO: 16, and SEQ ID NO: 17, respectively; and wherein the (framework region) residues at positions 39, 55 and 66 are Ile, Tyr and Tyr residues, respectively (see Example 2, below).

Also particularly disclosed herein is a CD133-binding agent IgG RW01 comprising a light chain amino acid sequence as shown in SEQ ID NO: 2 and a heavy chain amino acid sequence as shown in SEQ ID NO: 3 (see Example 2, below).

Yet further particularly disclosed herein is a CD133-binding agent IgG RW03 comprising a light chain amino acid sequence as shown in SEQ ID NO: 4 and a heavy chain amino acid sequence as shown in SEQ ID NO: 5 (see Example 2, below).

Accordingly, the disclosure also provides a CD133-binding agent comprising:

(i) an antibody light chain variable domain comprising a light chain CDR1 comprising the amino acid sequence of SEQ ID NO: 6, a light chain CDR2 comprising the amino acid sequence of SEQ ID NO: 7, and/or a light chain CDR3 comprising the amino acid sequence of SEQ ID NO: 8; and/or (ii) an antibody heavy chain variable domain comprising a Met residue at position 39 and a heavy chain CDR1 comprising the amino acid sequence of SEQ ID NO: 9; a Ser residue at position 55, a Tyr residue at position 66 and a heavy chain CDR2 comprising the amino acid sequence of SEQ ID NO: 10; and/or a heavy chain CDR3 comprising the amino acid sequence of SEQ ID NO: 11, wherein the antibody light chain variable domain and the antibody heavy chain variable domain form an antigen binding site that binds human CD133.

In one embodiment, the antibody light chain variable domain comprises a light chain CDR1, a light chain CDR2, and a light chain CDR3 comprising the amino acid sequences of SEQ ID NO: 6, SEQ ID NO: 7 and SEQ ID NO: 8, respectively; and the antibody heavy chain variable domain comprises a heavy chain CDR1, a heavy chain CDR2, and a heavy chain CDR3 comprising the amino acid sequences of SEQ ID NO: 9, SEQ ID NO: 10 and SEQ ID NO: 11, respectively; and the antibody heavy chain variable domain comprises Met, Ser and Tyr residues at positions 39, 55 and 66, respectively.

In another embodiment, the antibody light chain variable domain comprises a light chain CDR1, a light chain CDR2, and a light chain CDR3 consisting of the amino acid sequences of SEQ ID NO: 6, SEQ ID NO: 7 and SEQ ID NO: 8, respectively; and the antibody heavy chain variable domain comprises an amino acid sequence (SEQ ID NO: 32) composed of a heavy chain CDR1 consisting of the amino acid sequence of SEQ ID NO: 9, and a Met residue flanking the heavy chain CDR1 at position 39; an amino acid sequence (SEQ ID NO: 33) composed of a heavy chain CDR2 consisting of the amino acid sequence of SEQ ID NO: 10, a Ser residue flanking the heavy chain CDR2 at position 55, and a Tyr residue flanking the heavy chain CDR2 at position 66; and a heavy chain CDR3 consisting of the amino acid sequence of SEQ ID NO: 11.

In a further embodiment, the light chain comprises the amino acid sequence of SEQ ID NO: 2 or an amino acid sequence having at least 70% sequence identity to the framework regions of SEQ ID NO: 2; and/or the heavy chain comprises the amino acid sequence of SEQ ID NO: 3 or an amino acid sequence having at least 70% sequence identity to the framework regions of SEQ ID NO: 3.

In still a further embodiment, the light chain consists of the amino acid sequence of SEQ ID NO: 2, and/or the heavy chain consists of the amino acid sequence of SEQ ID NO: 3.

Accordingly, the disclosure also provides a CD133-binding agent comprising:

(i) an antibody light chain variable domain comprising a light chain CDR1 comprising the amino acid sequence of SEQ ID NO: 12, a light chain CDR2 comprising the amino acid sequence of SEQ ID NO: 13, and/or a light chain CDR3 comprising the amino acid sequence of SEQ ID NO: 14; and/or (ii) an antibody heavy chain variable domain comprising a Ile residue at position 39 and a heavy chain CDR1 comprising the amino acid sequence of SEQ ID NO: 15; Tyr residues at positions 55 and 66 and a heavy chain CDR2 comprising the amino acid sequence of SEQ ID NO: 16; and/or a heavy chain CDR3 comprising the amino acid sequence of SEQ ID NO: 17, wherein the antibody light chain variable domain and the antibody heavy chain variable domain form an antigen binding site that binds human CD133.

In one embodiment, the antibody light chain variable domain comprises a light chain CDR1, a light chain CDR2, and a light chain CDR3 comprising the amino acid sequences of SEQ ID NO: 12, SEQ ID NO: 13 and SEQ ID NO: 14, respectively; and the antibody heavy chain variable domain comprises a heavy chain CDR1, a heavy chain CDR2, and a heavy chain CDR3 comprising the amino acid sequences of SEQ ID NO: 15, SEQ ID NO: 16 and SEQ ID NO: 17, respectively; and the antibody heavy chain variable domain comprises Ile, Tyr and Tyr residues at positions 39, 55 and 66, respectively.

In another embodiment, the antibody light chain variable domain comprises a light chain CDR1, a light chain CDR2, and a light chain CDR3 consisting of the amino acid sequences of SEQ ID NO: 12, SEQ ID NO: 13 and SEQ ID NO: 14, respectively; and the antibody heavy chain variable domain comprises an amino acid sequence (SEQ ID NO: 34) composed of a heavy chain CDR1 consisting of the amino acid sequence of SEQ ID NO: 15 and a Ile residue flanking the heavy chain CDR1 at position 39; an amino acid sequence (SEQ ID NO: 35) composed of a heavy chain CDR2 consisting of the amino acid sequence of SEQ ID NO: 16, a Tyr residue flanking the heavy chain CDR2 at position 55, and a Tyr residue flanking the heavy chain CDR2 at position 66; and a heavy chain CDR3 consisting of the amino acid sequence of SEQ ID NO: 17.

In a further embodiment, the antibody light chain comprises the amino acid sequence of SEQ ID NO: 4 or an amino acid sequence having at least 70% sequence identity to the framework regions of SEQ ID NO: 4; and/or the antibody heavy chain comprises the amino acid sequence of SEQ ID NO: 5 or an amino acid sequence having at least 70% sequence identity to the framework regions of SEQ ID NO: 5.

In a still further embodiment, the light chain consists of the amino acid sequence of SEQ ID NO: 4, and the heavy chain consists of the amino acid sequence of SEQ ID NO: 5.

Any of the CD133-binding agents of the present disclosure may be obtained and suitably prepared for use using well-known techniques.

Polypeptidic CD133-binding agents of the disclosure can be synthesized by recombinant techniques which are well known and routinely practiced in the art. A polypeptidic CD133-binding agent of the disclosure may be produced in recombinant sources, such as recombinant cell lines or transgenic animals. Techniques can be adapted for the production of single-chain antibodies, such as a scFv, specific to CD133 (see, e.g. U.S. Pat. No. 4,946,778).

Alternatively, a polypeptidic CD133-binding agent of the disclosure, such as a CD133-binding antibody of the disclosure may be obtained by immunizing an animal with CD133, or with a polypeptide comprising a suitable CD133 epitope, so as to generate the antibody in the animal's serum.

A CD133-binding IgG antibody of the disclosure can be purified from a biological sample, such as serum, via techniques such as affinity chromatography using protein A or protein G (see, e.g. Wilkinson, 2000). Additionally or alternatively, CD133, or a polypeptide comprising an epitope thereof, which is specifically bound by the CD133-binding agent may be immobilized on a column to purify the CD133-binding agent from a sample by immunoaffinity chromatography.

A CD133-binding antibody fragment of the disclosure may be obtained from an antibody using conventional techniques. For example, F(ab')2 fragments can be generated by treating an antibody with pepsin. The resulting F(ab')2 fragment can be treated to reduce disulfide bridges to produce Fab' fragments.

Methods of producing polypeptidic CD133-binding agents of the disclosure are described in further detail below.

As set forth above, in an embodiment, the CD133-binding agent may be a bispecific antibody.

As used herein, bispecific antibodies are binding agents comprising two different antibody variable regions which confer binding specificities for at least two different antigens or two different epitopes of the same antigen.

The presently disclosed bispecific antibodies specifically bind CD133 and another antigen or specifically bind different epitopes of CD133. Optionally, the bispecific antibody binds CD133 and a cell-surface protein, receptor or receptor subunit.

In one embodiment, the bispecific antibody comprises a CD133-binding single-chain Fab and a non-CD133-binding scFv. Alternately, the bispecific antibody comprises a CD133-binding Fab and a non-CD133-binding scFv.

In another embodiment, the CD133-binding agent is a bispecific antibody that targets, binds and/or engages immune cells such as T cells, macrophages or NK cells. According to this embodiment, the CD133-binding agent is a bispecific antibody where one of the binding specificities is for CD133 and the other binding specificity is for an antigen expressed on the surface of T cells, macrophages or NK cells. For example, the bispecific antibody may bind CD133 and an immune cell receptor, such a receptor of a T cell, which when bound activates or inhibits activity of the immune cell.

Various techniques for making and isolating bispecific antibodies directly from recombinant cell culture have been described. For example, bispecific antibodies have been produced using leucine zippers (see, e.g. Kostelny et al., 1992), using "diabody" technology (see, e.g. Hollinger et al., 1993), and using single-chain Fv (scFv) dimers (see, e.g. Gruber et al., 1994).

A bispecific antibody that engages T cells may be referred to as a bispecific T-cell engager (BiTE). In one embodiment of the present disclosure, the bispecific antibody/BiTE specifically binds both CD133 and the T cell co-receptor CD3 (also referred to herein as CD133-binding/CD3-binding bispecific antibody). Accordingly, provided herein is a bispecific antibody/BiTE which comprises a CD133-binding antibody variable region of the disclosure and a CD3-binding antibody variable region. Such bispecific antibodies/BiTEs allow targeting of a T cell to a cell, such as a cancer cell, expressing surface CD133. Various configurations of the bispecific antibodies/BiTEs are contemplated herein. For example, in one embodiment, the bispecific antibody/BiTE comprises an anti-CD133 Fab and an anti-CD3 scFv. Optionally, either the light chain or the heavy chain of the anti-CD133 Fab is linked to the heavy-chain of the anti-CD3 scFv. In another embodiment, the bispecific antibody/BiTE comprises an anti-CD133 single chain Fab (scFab) and an anti-CD3 ScFv. Optionally, either the light chain or the heavy chain of the anti-CD133 Fab or anti-CD133 scFab is linked to the heavy-chain of the anti-CD3 scFv. In one embodiment, the anti-CD3 scFv binds CD3 epsilon/gamma. In one embodiment, the BiTE/bispecific antibody binds CD3 epsilon/delta. See, for example FIG. 10A. Examples of configurations and amino acid sequences of various embodiments of the BiTE are provided in Table 6. Accordingly, the present disclosure also provides a BiTE comprising one or more amino acid sequences selected from (a) SEQ ID NO: 22 and SEQ ID NO: 23, (b) SEQ ID NO: 24 and SEQ ID NO: 25, (c) SEQ ID NO: 26, and (d) SEQ ID NO: 27, or functional variants thereof. In one embodiment, the BiTE comprises an amino acid sequence having at least 50%, or at least 60%, or at least 70%, or at least 80%, or at least 90%, or at least 95% sequence identity to any one of SEQ ID Nos: 22-27.

In a further embodiment, the bispecific antibody binds CD133 and the NK cell surface receptor CD16.

In another embodiment of the present disclosure, the CD133-binding agent is a bispecific antibody comprising antibody variable region RW01 and antibody variable region RW03.

As described above, the CD133-binding agent may have any number of valencies and/or specificities. For example, a trispecific and/or trivalent CD133-binding agent can be prepared (see, e.g. Tutt et al., 1991).

As further described above, embodiments of the CD133-binding agents also include CD133-binding chimeric antigen receptors (CARs).

Accordingly, provided herein is a chimeric antigen receptor comprising (i) a CD133-binding agent of the disclosure and (ii) a CAR signaling domain comprising one or more immune cell receptor signaling domains. Chimeric antigen receptors are engineered receptors wherein a polypeptide comprising a CD133-binding variable region of the present disclosure, for example a CD133-binding scFv, is fused, for example via a hinge domain and transmembrane domain, to a CAR signaling domain comprising one or more intracellular signaling domains of one or more immune cell receptors. The CAR can be a monomeric polypeptide (e.g. anti-CD133 scFv-based) or a multimeric polypeptide (e.g. anti-CD133 Fab-based). Expression of such a CAR in an immune effector cell allows targeting of the immune cell to a cell expressing surface CD133, where binding of the CAR to the cell surface expressed CD133 activates effector functions of the immune effector cell.

In one embodiment, the CAR signaling domain comprises a signaling domain of the T cell co-receptor CD3 (e.g. CD3zeta or CD3gamma). In another embodiment, the CAR comprises a signaling domain of the T cell co-receptor CD3 fused to a signaling domain of one or more T cell costimulatory molecules (e.g. CD28, 4-1BB, CD137, OX40, ICOS and/or CD27). In yet another embodiment, the CAR signaling domain comprises CD3zeta, and portions of CD8 and CD28. In another embodiment, the CAR signaling domain comprises a human CD8 leader sequence and a CD8a transmembrane domain. In one embodiment the CAR comprises a CD28 signaling domain, and a terminal CD3zeta signaling domain. In a further embodiment, the CAR signaling domain comprises a CD3zeta signaling domain, a 4-1BB signaling domain, and a CD28 signaling domain. Different configurations of a scFv comprised in the CAR are contemplated including VL-linker-VH and VH-linker-VL. The construction of suitable CARs and their use for targeting antigen expressing cells, commonly referred to in the art as "CAR T cell therapy", is well known in the art (see, e.g. Maus and June, 2016; Abate-Daga and Davila, 2016; Resetca et al., 2016; and Wang and Riviere, 2016).

In an additional embodiment, the CD133-binding agent is a phage-Fab or phage-scFv, where the Fab or scFv specifically binds CD133. The disclosure also provides a T cell expressing a CAR as described herein.

It can be desirable to modify a binding agent disclosed herein with respect to effector function, so as to enhance its effectiveness in binding/targeting CD133-expressing cells and/or reducing levels of CD133 in CD133-expressing cells. For example, where the binding agent comprises an antibody Fc region, such as an antibody, cysteine residue(s) can be introduced into the COOH terminal of the Fc region, thereby allowing interchain disulfide bond formation between antibody monomers in this region. The homodimeric antibody thus generated can have improved internalization capability and/or increased complement-mediated cell killing and antibody-dependent cellular cytotoxicity (ADCC) (see, e.g. Caron et al., 1992; and Shopes, 1992).

Alternatively, an antibody can be engineered that has dual Fc regions and can thereby have enhanced complement lysis and ADCC capabilities (see, e.g. Stevenson et al., 1989). Functional variants of the CD133-binding agents described herein are also encompassed by the present disclosure. The term "functional variant" as used herein includes modifications or chemical equivalents of the amino acid and nucleic acid sequences disclosed herein that perform substantially the same function as the polypeptides or nucleic acid molecules disclosed herein in substantially the same way. For example, functional variants of polypeptides disclosed herein include, without limitation, conservative amino acid substitutions.

A "conservative amino acid substitution" as used herein, is one in which one amino acid residue is replaced with another amino acid residue are substitutions that change an amino acid to a different amino acid with similar biochemical properties (e.g. charge, hydrophobicity and size). Variants of polypeptides also include additions and deletions to the polypeptide sequences disclosed herein. In addition, variant nucleotide sequences include analogs and derivatives thereof. A variant of the binding agents disclosed herein include agents that bind to the same antigen or epitope as the binding agents.

In one embodiment, the present disclosure includes functional variants to the amino acid sequences disclosed herein. In particular, the disclosure provides functional variants of the amino acid sequences of the light chain and heavy chain of IgG RW01 (SEQ ID NO: 2 and SEQ ID NO: 3, respectively), functional variants of the amino acid sequences of the CDRs of antibody variable region RW01 (SEQ ID NO: 6, SEQ ID NO: 7, SEQ ID NO: 8, SEQ ID NO: 9, SEQ ID NO: 10 and SEQ ID NO: 11), and functional variants of the amino acid sequences corresponding to SEQ ID NO: 32 and SEQ ID NO: 33 of the heavy chain of antibody variable region RW01. The disclosure further particularly provides functional variants of the amino acid sequences of the light chain and heavy chain of IgG RW03 (SEQ ID NO: 4 and SEQ ID NO: 5, respectively), functional variants of the amino acid sequences of the CDRs of antibody variable region RW03 (SEQ ID NO: 12, SEQ ID NO: 13, SEQ ID NO: 14, SEQ ID NO: 15, SEQ ID NO: 16 and SEQ ID NO: 17), and functional variants of the amino acid sequences corresponding to SEQ ID NO: 34 and SEQ ID NO: 35 of the heavy chain of antibody variable region RW03.

In another embodiment, the present disclosure includes functional variants to the nucleic acid sequences that encode the amino acid sequences disclosed herein. Particularly provided are functional variants of the nucleotide sequences encoding the light chain and heavy chain of IgG RW01 (SEQ ID NO: 18 and SEQ ID NO: 19, respectively), functional variants of the nucleotide sequences encoding the light chain and heavy chain variable domains of antibody variable region RW01 (SEQ ID NO: 52 and SEQ ID NO: 53, respectively), functional variants of the nucleotide sequences encoding the amino acid sequences of the CDRs of antibody variable region RW01 (SEQ ID NO: 36, SEQ ID NO: 37, SEQ ID NO: 38, SEQ ID NO: 39, SEQ ID NO: 40 and SEQ ID NO: 41), and functional variants of the nucleotide sequences encoding the amino acid sequences corresponding to SEQ ID NO: 32 and SEQ ID NO: 33 of the heavy chain of antibody variable region RW01 (SEQ ID NO: 42 and SEQ ID NO: 43, respectively).

The disclosure further particularly provides functional variants of the nucleotide sequences encoding the light chain and heavy chain of IgG RW03 (SEQ ID NO: 20 and SEQ ID NO: 21, respectively), functional variants of the nucleotide sequences encoding the light chain and heavy chain variable domains of antibody variable region RW03 (SEQ ID NO: 54 and SEQ ID NO: 55, respectively), functional variants of the nucleotide sequences encoding the amino acid sequences of the CDRs of antibody variable region RW03 (SEQ ID NO: 44, SEQ ID NO: 45, SEQ ID NO: 46, SEQ ID NO: 47, SEQ ID NO: 48 and SEQ ID NO: 49), and functional variants of the nucleotide sequences encoding the amino acid sequences corresponding to SEQ ID NO: 34 and SEQ ID NO: 35 of the heavy chain of antibody variable region RW03 (SEQ ID NO: 50 and SEQ ID NO: 51, respectively).

In addition, the functional variants include nucleotide sequences that hybridize to the nucleic acids encoding the amino acid sequences of the present disclosure, or the complement thereof, under at least moderately stringent hybridization conditions. Such functional variants include nucleotide sequences that hybridize to SEQ ID NO: 18, SEQ ID NO: 19, SEQ ID NO: 20, SEQ ID NO: 21, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54 or SEQ ID NO: 55, or the complement thereof, under at least moderately stringent hybridization conditions.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41 (%(G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

In one embodiment, the variant amino acid sequences of the amino acid sequences disclosed herein comprise sequences having at least 50%, or at least 60%, or at least 70%, or at least 80%, or at least 90%, or at least 95% sequence identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 28, SEQ ID NO: 29, SEQ ID NO: 30, SEQ ID NO: 31, SEQ ID NO: 32, SEQ ID NO: 33, SEQ ID NO: 34 or SEQ ID NO: 35.

In another embodiment, the variant amino acid sequences of the amino acid sequences disclosed herein comprise sequences having at least 50%, or at least 60%, or at least 70%, or at least 80%, or at least 90%, or at least 95% sequence identity to the framework regions of SEQ ID NOS: 2, 3, 4 or 5. In another embodiment, the variant nucleotide sequences encoding the amino acid sequences disclosed herein comprise sequences having at least 50%, or at least 60%, or at least 70%, or at least 80%, or at least 90%, or at least 95% sequence identity to SEQ ID NO: 18, SEQ ID NO: 19, SEQ ID NO: 20, SEQ ID NO: 21, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54 or SEQ ID NO: 55.

In another embodiment, the variant nucleotide sequences encoding amino acid sequences comprising heavy and light chain variable domains disclosed herein comprise sequences having at least 50%, or at least 60%, or at least 70%, or at least 80%, or at least 90%, or at least 95% sequence identity to the nucleotide sequences encoding such amino acid sequences, including SEQ ID NO: 18, SEQ ID NO: 19, SEQ ID NO: 20, SEQ ID NO: 21, SEQ ID NO: 52, SEQ ID NO: 53, SEQ ID NO: 54 and SEQ ID NO: 55.

The term "sequence identity" as used herein refers to the percentage of sequence identity between two amino acid sequences or two nucleic acid sequences. To determine the percent identity of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, modified as in Karlin and Altschul, 1993. Such an algorithm is incorporated into the NBLAST and XBLAST programs of Altschul et al., 1990. BLAST nucleotide searches can be performed with the NBLAST nucleotide program parameters set, e.g. for score=100, wordlength=12 to obtain nucleotide sequences homologous to a nucleic acid molecules of the present disclosure. BLAST protein searches can be performed with the XBLAST program parameters set, e.g. to score=50, wordlength=3 to obtain amino acid sequences homologous to a protein molecule of the present invention. To obtain gapped alignments for comparison purposes, Gapped BLAST can be utilized as described in Altschul et al., 1997. Alternatively, PSI-BLAST can be used to perform an iterated search which detects distant relationships between molecules. When utilizing BLAST, Gapped BLAST, and PSI-Blast programs, the default parameters of the respective programs (e.g. of XBLAST and NBLAST) can be used (see, e.g. the NCBI website). Another non-limiting example of a mathematical algorithm utilized for the comparison of sequences is the algorithm of Myers and Miller, 1988. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

Nucleic Acids and Vectors

Also provided are nucleic acids encoding the antibody variable regions described herein and nucleic acids encoding polypeptides comprising these antibody variable regions. As used herein, the term "nucleic acids" includes isolated nucleic acids.

In particular the present disclosure provides nucleic acids encoding the CDR regions of antibody variable region RW01 as set out in SEQ ID NOs: 36-41, and functional variants thereof; and nucleic acids encoding the amino acid sequences of the heavy chain variable domain of RW01 as set out in SEQ ID NOs: 42 and 43, and functional variants thereof. Also provided are nucleic acids encoding the CDR regions of RW03 as set out in SEQ ID NOs: 44-49, and functional variants thereof; and nucleic acids encoding the amino acid sequences of the heavy chain variable domain of RW03 as set out in SEQ ID NOs: 50 and 51, and functional variants thereof.

Further provided is a nucleic acid (SEQ ID NO: 52) encoding the light chain variable domain of antibody variable region RW01, and functional variants thereof. In one embodiment, the nucleic acid encodes (a) the amino acid sequence of SEQ ID NO: 28 or (b) an amino acid sequence having at least 70% sequence identity to the framework regions of SEQ ID NO: 28. Also provided is a nucleic acid (SEQ ID NO: 53) encoding the heavy chain of IgG RW01. In one embodiment, the nucleic acid encodes (a) the amino acid sequence of SEQ ID NO: 29 or (b) an amino acid sequence having at least 70% sequence identity to the framework regions of SEQ ID NO: 29.

Further provided is a nucleic acid (SEQ ID NO: 54) encoding the light chain variable domain of antibody variable region RW03, and functional variants thereof. In one embodiment, the nucleic acid encodes (a) the amino acid sequence of SEQ ID NO: 30 or an amino acid sequence having at least 70% sequence identity to the framework regions of SEQ ID NO: 30. Also provided is a nucleic acid (SEQ ID NO: 55) encoding the heavy chain variable domain of antibody variable region RW03. In one embodiment, the nucleic acid encodes (a) the amino acid sequence of SEQ ID NO: 31 or an amino acid sequence having at least 70% sequence identity to the framework regions of SEQ ID NO: 31.

The disclosure also provides nucleic acids encoding the light chain and heavy chain of IgG RW01 and IgG RW03 as set out in SEQ ID Nos: 18, 19, 20 and 21, and functional variants thereof.

The disclosure also provides nucleic acids encoding the variable domains of the light chain and heavy chain of antibody variable region RW01 and antibody variable region RW03 as set out in SEQ ID Nos: 52, 53, 54 and 55, and functional variants thereof.

Polypeptidic binding agents disclosed herein can be expressed by a vector containing a nucleic acid encoding the polypeptide of interest using methods which are well known and routinely practiced in the art. Accordingly, the present disclosure also provides a vector expressing any of the nucleic acids described herein.

The polypeptidic binding agents can be prepared by constructing a nucleic acid encoding a polypeptidic binding agent, inserting the construct into an expression vector, and then expressing it in appropriate host cells. Vectors useful for expressing the polypeptidic binding agents disclosed herein are well known in the art. In one embodiment, the vector includes suitable translation initiation and termination signals in operable reading phase with a functional promoter and can comprise one or more phenotypic selectable markers and an origin of replication to ensure maintenance of the vector and, if desirable, to provide amplification within the host. In addition to vectors, the nucleic acids of the present disclosure can be delivered to a cell or a subject via any other method known in the art including, but not limited to, liposomes, naked DNA, adjuvant-assisted DNA, gene gun, catheters, etc.

Monoclonal Polypeptides/Monoclonal Antibodies

As described above, the CD133-binding agent can be a polypeptide comprising a CD133-binding antibody variable region, such as an antibody specifically comprising antibody variable region RW01 or antibody variable region RW03. Accordingly, the disclosure further provides a monoclonal polypeptidic CD133-binding agent of the disclosure, such as a monoclonal CD133-binding antibody of the disclosure.

As used herein, a "monoclonal" polypeptidic CD133-binding agent of the disclosure refers to a population of identical polypeptidic CD133-binding agent molecules. For example, in the case of a monoclonal polypeptidic CD133-binding agent of the disclosure comprising a CD133-binding antibody variable region, such as a monoclonal CD133-binding antibody of the disclosure, the CDRs are identical in all the molecules of the population. Various procedures known within the art may be used for the production of monoclonal polypeptides, such as monoclonal antibodies of the disclosure (see, for example, Greenfield, 2013). Monoclonal antibodies are commonly alternatively referred to using the abbreviations "mAb" or "MAb".

Monoclonal antibodies can be made by recombinant DNA methods, such as those described in U.S. Pat. No. 4,816,567. DNA encoding the monoclonal antibodies and antigen-binding fragments thereof can be readily isolated and sequenced using conventional procedures (e.g. by using oligonucleotide probes that are capable of binding specifically to genes encoding the heavy and light chains of murine antibodies). The hybridoma cells serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

Monoclonal antibodies may also be generated, e.g. by immunizing an animal with CD133, such as, for example, murine, rat or human CD133 or an immunogenic fragment, derivative or variant thereof. Alternatively, the animal is immunized with cells transfected with a vector containing a nucleic acid molecule encoding CD133 that is expressed and associated with the surface of the transfected cells. Alternatively, the antibodies are obtained by screening a library that contains antibody or antigen binding domain sequences for binding to CD133. This library is prepared, e.g. in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to CD133.

Monoclonal antibodies may be prepared, for example, using hybridoma methods (see, for example, Kohler and Milstein, 1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Affinity

Non-covalent interactions occur between an immunoglobulin molecule and an antigen for which the immunoglobulin is specific. The strength, or affinity of immunological binding interactions can be expressed in terms of the dissociation constant ($K_D$) of the interaction, wherein a smaller $K_D$ represents a greater affinity. Immunological binding properties of specific polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation (see, e.g. Malmqvist, 1993). The ratio of $K_{off}/K_{on}$ enables the cancellation of all parameters not related to affinity, and is equal to the dissociation constant $K_D$ (see, e.g. Davies et al., 1990).

A bivalent CD133-binding agent disclosed herein, such as a CD133-binding agent comprising two CD133-binding antibody variable regions (e.g. an antibody or F(ab')$_2$), is considered to specifically bind CD133 when the dissociation constant ($K_D$) of the binding is ≤1 micromolar. A monovalent CD133-binding agent disclosed herein (i.e. which has single CD133-binding site, such as a single CD133-binding antibody variable region, e.g. a scFv or a Fab) is said to specifically bind CD133 when the dissociation constant ($K_D$) of the binding of the CD133-binding agent in bivalent form is ≤1 micromolar. Methods for joining monovalent binding agents of the disclosure for generating suitable bivalent forms thereof are well known in the art (e.g. where the monovalent agent comprises a single antibody variable region, production of bivalent antibodies/F(ab')$_2$ comprising two copies of the antibody variable region; or e.g. using suitable linkers, such as polypeptide linkers, nucleic acid linkers or chemically synthesized linkers).

In various embodiments, the CD133-binding agent binds CD133 with a dissociation constant ($K_D$) of ≤1 micromolar, ≤900 nM, ≤800 nM, ≤700 nM, ≤600 nM, ≤500 nM, 400 nM, ≤300 nM, ≤200 nM, ≤100 nM, ≤90 nM, ≤80 nM, ≤70 nM, ≤60 nM, ≤50 nM, ≤40 nM, ≤30 nM, ≤20 nM, ≤10 nM, ≤9 nM, ≤8 nM, ≤7 nM, ≤6 nM, ≤5 nM, ≤4 nM, ≤2 nM, ≤1 nM, ≤50.9 nM, ≤0.8 nM, ≤0.7 nM, ≤0.6 nM, 0.5 nM, ≤0.4 nM to 0.3 nM, ≤0.2 nM, or ≤100 pM to about 1 pM.

In further various embodiments, the CD133-binding agent binds CD133 with a dissociation constant ($K_D$) of ≤1 micromolar to 100 nM, ≤100 nM to 10 nM, ≤10 nM to 1 nM, ≤1 nM to 0.1 nM, or ≤0.1 nM to 10 pM.

In additional various embodiments, the CD133-binding agent binds CD133 with a dissociation constant ($K_D$) of ≤3 nM to 2 nM, ≤2.6 nM to 2.4 nM, ≤2.5 nM, about 2.5 nM, 2 nM to 1 nM, ≤0.6 nM to 0.4 nM, ≤0.5 nM, or about 0.5 nM.

As disclosed herein, the dissociation constant KD for the binding of a bivalent CD133-binding agent, such as a CD133-binding antibody of the disclosure or a monovalent CD133-binding agent in bivalent form, is considered to approximately correspond to the half-maximal concentration ("EC50") of the CD133-binding agent required to saturate binding to a population of CD133-overexpressing cells, such as HEK293-CD133 cells, as determined via flow cytometry (see Example 3, below). This method is useful for determining the affinity of a binding agent for a cell surface molecule which cannot be suitably purified, as is often the case with transmembrane proteins, such as CD133. Alternate methods of determining a dissociation constant (KD) for binding of a CD133-binding agent to cell surface-expressed CD133 include radioligand binding assays, and similar assays known to those skilled in the art. Alternately, where CD133 or a portion thereof bound by a CD133-binding agent of the disclosure is available in purified form, the dissociation constant (KD) can be measured by assays such as surface plasmon resonance (SPR; Biacore™) assay and other suitable assays known in the art.

As described above, the disclosure provides a CD133-binding agent which specifically binds a CD133 epitope bound by antibody IgG RW01 and/or a CD133 epitope bound by antibody IgG RW03.

Any one of various methods known in the art can be used to identify a CD133-binding agent which specifically binds a CD133 epitope bound by antibody IgG RW01 and/or a CD133 epitope bound by antibody IgG RW03. A person skilled in the art will appreciate that binding assays such as a competition binding assay can be used for this purpose. Those skilled in the art will recognize that it is possible to determine, without undue experimentation, if a binding agent specifically binds a CD133 epitope bound by antibody IgG RW01 and/or a CD133 epitope bound by antibody IgG RW03 by ascertaining whether the binding agent prevents antibody IgG RW01 and/or antibody IgG RW03 from binding to human CD133. If the binding agent being tested competes with antibody IgG RW01 and/or antibody IgG RW03, as shown by a decrease in binding to human CD133 by antibody IgG RW01 and/or antibody IgG RW03, then the binding agent binds to the same epitope as antibody IgG RW01 and/or antibody IgG RW03. Methods for the testing the specificity of binding agents include, but are not limited to, enzyme linked immunosorbent assay (ELISA) and other immunologically mediated techniques known within the art.

In one embodiment, the CD133-binding agent which specifically binds a CD133 epitope bound by antibody IgG RW01 and/or a CD133 epitope bound by antibody IgG RW03 is a CD133-binding agent which competes with antibody IgG RW01 and/or antibody IgG RW03 for binding to the surface of CD133-expressing cells. In one embodiment, the CD133 epitope is a human CD133 epitope. For example, a CD133-binding agent which specifically binds a CD133 epitope bound by antibody IgG RW01 and/or a CD133 epitope bound by antibody IgG RW03 will partially or fully inhibit binding of antibody IgG RW01 and/or antibody IgG RW03 to CD133-expressing cells pre-incubated with a saturating concentration of such a binding agent, as determined via flow cytometry analogously to the experiments disclosed in Example 7. Alternately, a CD133-binding agent which specifically binds a CD133 epitope bound by antibody IgG RW01 and/or a CD133 epitope bound by antibody IgG RW03 will partially or fully inhibit binding of antibody IgG RW01 and/or antibody IgG RW03 to denatured CD133, e.g. denatured CD133 electroblotted onto a membrane (e.g. nitrocellulose or PVDF) following electrophoretic separation under reducing conditions of denatured protein of whole cell lysate (see, e.g. Example 6), where the membrane has been pre-incubated with a saturating concentration of such binding agent.

In another embodiment, the CD133-binding agent which specifically binds a CD133 epitope bound by antibody IgG RW01 and/or a CD133 epitope bound by antibody IgG RW03 is a monovalent CD133-binding agent (e.g. a Fab or a scFv) which competes with Fab comprising antibody variable region RW01 and/or Fab comprising antibody variable region RW03 for binding to the surface of CD133-expressing cells. In one embodiment, the CD133 epitope is a human CD133 epitope. For example, a monovalent CD133-binding agent which specifically binds a CD133 epitope bound by antibody IgG RW01 and/or a CD133 epitope bound by antibody IgG RW03 will partially or fully inhibit binding of Fab comprising antibody variable region RW01 and/or Fab comprising antibody variable region RW03 to CD133-expressing cells pre-incubated with a saturating concentration of such a binding agent, as determined via flow cytometry analogously to the experiments disclosed in Example 7. Alternately, the monovalent agent will partially or fully inhibit binding of Fab comprising antibody variable region RW01 and/or Fab comprising antibody variable region RW03 to denatured CD133, e.g. denatured CD133 electroblotted onto a membrane (e.g. nitrocellulose or PVDF) following electrophoretic separation under reducing conditions of denatured protein of whole cell lysate (see, e.g. Example 6), where the membrane has been pre-incubated with a saturating concentration of such binding agent following electroblotting. In one embodiment, the CD133 is human CD133.

Detection Agents

The binding agents described herein are optionally labeled with a detection agent. As used herein, the term "detection agent" refers to any agent that allows the presence of the binding agent to be detected and/or quantified. Examples of detection agents include, but are not limited to, peptide tags, enzymes (for example, HRP or alkaline phosphatase), proteins (for example phycoerythrin or biotin/streptavidin), magnetic particles, chromophores, fluorescent molecules, chemiluminescent molecules, radioactive labels and dyes. The binding agent may be labeled directly or indirectly with the detection agent.

Humanized Antibodies

The nucleotide sequence encoding a non-human, e.g. murine, CD133-binding agent disclosed herein can be modified, for example, by substituting the coding sequence for human heavy and light chain constant domains in place of the homologous non-human, e.g. murine, sequences (see, e.g. U.S. Pat. No. 4,816,567; and Morrison, 1994) or by covalently joining to the immunoglobulin coding sequence all or part of the coding sequence for a non-immunoglobulin polypeptide. Such a non-immunoglobulin polypeptide can be substituted for the constant domains of an antibody disclosed herein, or can be substituted for the variable domains of one antigen-combining site of an antibody disclosed herein to create a chimeric bivalent antibody.

The non-human binding agents comprising Fc regions, e.g. non-human antibodies, described herein may be humanized in order to make them better tolerated for use in humans. For example, amino acid residues in the framework regions may be humanized by replacing them with amino acid residues and the human framework regions as long as the replacement does not impair the ability of the binding agents to bind to CD133 (see, e.g. Vincke et al., 2008).

It will be appreciated that murine antibodies or antibodies from other species can be humanized or primatized using techniques well known in the art (see, e.g. Winter and Harris, 1993; and Wright et al., 1992). An antibody may be engineered by recombinant DNA techniques to substitute the CH1, CH2, CH3, hinge domains, and/or the framework domain with the corresponding human sequence (see, e.g. WO 92102190 and U.S. Pat. Nos. 5,530,101; 5,585,089; 5,693,761; 5,693,792; 5,714,350; and 5,777,085). Also, the use of Ig cDNA for construction of chimeric immunoglobulin genes is known in the art (see, e.g. Liu et al., 1987a; and Liu et al., 1987b). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. Human C region genes are readily available from known clones. The choice of isotype will be guided by the desired effector functions, such as complement fixation, or activity in antibody-dependent cellular cytotoxicity. Either of the human light chain constant regions, kappa or lambda, may be used. The chimeric, humanized antibody may then be expressed by conventional methods.

As described above, the CD133-binding agent may be a human antibody. Fully human antibodies are antibody molecules in which the entire sequence of both the light chain and the heavy chain, including the CDRs, arise from human genes. Such antibodies are termed "human antibodies" or "fully human antibodies" herein. Human monoclonal antibodies can be prepared by using the trioma technique; the human B-cell hybridoma technique (see, e.g. Kozbor, et al., 1983), and the EBV hybridoma technique to produce human monoclonal antibodies (see, e.g. Cole et al., 1985). Human monoclonal antibodies may be utilized and may be produced by using human hybridomas (see, e.g. Cote, et al., 1983) or by transforming human B-cells with Epstein Barr Virus in vitro (see, e.g. Cole et al., 1985).

A CD133-binding polypeptide comprising a CD133-binding antibody variable region, such as a CD133-binding scFv or CD133-binding Fab may be developed, for example, using phage-display methods using antibodies containing only human sequences. Such approaches are well-known in the art (see, e.g. WO92/01047 and U.S. Pat. No. 6,521,404, which are hereby incorporated by reference). In this approach, a combinatorial library of phage carrying random pairs of light and heavy chains are screened using natural or recombinant source of CD133 or fragments thereof. In another approach, an antibody or fragment can be produced by a process wherein at least one step of the process includes immunizing a transgenic, non-human animal with a CD133 protein. In this approach, some of the endogenous heavy and/or kappa light chain loci of this xenogeneic/non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the animal produces B-cells that secrete fully human immunoglobulins.

A variety of techniques are well-known in the art for producing xenogeneic/non-human animals (see, e.g. U.S. Pat. Nos. 6,075,181 and 6,150,584, which are hereby incorporated by reference; Green et al., 1994, which is hereby incorporated by reference in its entirety; U.S. Pat. Nos. 6,162,963, 6,150,584, 6,114,598, 6,075,181, and 5,939,598; Japanese Patent Nos. 3 068 180 B2, 3 068 506 B2, and 3 068 507 B2; European Patent No., EP 0 463 151 B1; and International Patent Application Nos. WO 94/02602, WO 96/34096, WO 98/24893, and WO 00/76310).

Alternatively, a "minilocus" approach may be used, in which an exogenous Ig locus is mimicked through the inclusion of pieces (individual genes) from the Ig locus (see, e.g. U.S. Pat. Nos. 5,545,806, 5,545,807, 5,591,669, 5,612,205, 5,625,825, 5,625,126, 5,633,425, 5,643,763, 5,661,016, 5,721,367, 5,770,429, 5,789,215, 5,789,650, 5,814,318, 5,877,397, 5,874,299, 6,023,010, and 6,255,458; European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884). Thus, one or more VH genes, one or more DH genes, one or more JH genes, a mu constant region, and a second constant region (preferably a gamma constant region) are formed into a construct for insertion into an animal.

Generation of human antibodies from mice in which, through microcell fusion, large pieces of chromosomes, or entire chromosomes, have been introduced, has also been demonstrated (see, e.g. European Patent Application Nos. 773 288 and 843 961).

Immunoconjugates

The present disclosure also includes an immunoconjugate comprising (1) a CD133-binding agent, optionally an antibody or an antibody antigen binding fragment, that has been attached to (2) an effector agent. As used herein, the term "immunoconjugate" encompasses CD133-binding agents of the disclosure which do not comprise an antibody variable region, and further encompasses CD133-binding agents disclosed herein which comprise an antibody variable region.

In one embodiment, the effector agent is a label, which can generate a detectable signal, directly or indirect. Examples of labels include radioactive isotopes (i.e., a radioconjugate).

In another embodiment, the effector agent is a therapeutic agent. Therapeutic agents include, but are not limited to, cancer therapeutic agents/antineoplastic agents. In yet another embodiment, the therapeutic agent is a toxin.

The term "cancer therapeutic agent" or "antineoplastic agent" is used herein to refer to agents that have the functional property of decreasing levels of CD133 in cancer cells, such as pancreatic cancer cells, colorectal cancer cells, breast cancer cells, colon cancer cells, gastric cancer cells, prostate cancer cells, liver cancer cells, lung cancer cells, melanoma cells, brain cancer cells (optionally glioblastoma or medulloblastoma cells) and head and neck squamous cell carcinoma cells.

The toxin may be an enzymatically active toxin of bacterial, fungal, plant, or animal origin, or a fragment thereof. Toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca ameri-*

*cana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

Radioconjugated CD133-binding agents of the disclosure, such as antibodies of the disclosure, may be employed to bind radionuclides to CD133-expressing cells, for example to visualize the cells or as a cytotoxic treatment of the cells. A variety of radionuclides are available for the production of radioconjugated antibodies. Examples include 212Bi, 131I, 131In, 90Y, and 186Re.

Those of ordinary skill in the art will recognize that a large variety of possible moieties can be coupled to the polypeptidic CD133-binding agents of the disclosure, such as those comprising an antibody variable region (e.g. antibodies or antibody fragments comprising a CD133-binding antibody variable region) (see, for example, Cruse and Lewis, 1989, the entire contents of which are incorporated herein by reference). Coupling may be accomplished by any chemical reaction that will bind a moiety and a CD133-binding agent of the disclosure, so long as these retain their respective activities/characteristics for the intended use thereof. This linkage can include many chemical mechanisms, for instance covalent binding, affinity binding, intercalation, coordinate binding and complexation.

For example, conjugates of a polypeptidic CD133-binding agent of the disclosure, such as an antibody and an effector agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987).

Carbon-14-labeled 1-isothiocyanatobenzyl-3-methyldiethylene triaminepentaacetic acid (MX-DTPA) is an exemplary chelating agent for conjugation of radionucleotide to the antibody (see, e.g. WO94/11026).

Pharmaceutical Compositions

The disclosure also provides pharmaceutical compositions comprising a CD133-binding agent or immunoconjugate or radioconjugate described herein as an active ingredient and a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin.

A pharmaceutical composition is formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

In one embodiment, the active ingredient is prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms are dictated by and directly dependent on the unique characteristics of the active ingredient and the particular therapeutic effect to be achieved, and the limitations inherent in the art of preparing such an active ingredient for the treatment of individuals.

The formulation can also contain more than one active ingredient as necessary for the particular indication being treated, optionally those with complementary activities that do not adversely affect each other. Alternatively, or in addition, the pharmaceutical composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Methods and Uses:

The disclosure also provides uses and methods relating to the CD133-binding agents described herein.

Detecting CD133-Expressing Cells

The CD133-binding agents, immunoconjugates and pharmaceutical compositions of the present disclosure are useful for detecting cells that express CD133. Accordingly, the disclosure provides a use of the CD133-binding agents described herein for targeting, binding and/or detecting CD133-expressing cells. Optionally, the cells are cancer cells, including, but not limited to, pancreatic cancer cells, colorectal cancer cells, breast cancer cells, colon cancer cells, gastric cancer cells, prostate cancer cells, liver cancer cells, lung cancer cells, melanoma cells, brain cancer cells and head and neck squamous cell carcinoma cells.

In one embodiment, the CD133-binding agents, immunoconjugates, and pharmaceutical compositions described herein are useful for targeting, binding and/or detecting cell surface expression of CD133-expressing cells.

In another embodiment, the CD133-binding agents, immunoconjugates and pharmaceutical compositions described herein are useful for targeting, binding, detecting and/or localizing intracellular CD133.

In another embodiment, the CD133-binding agents, immunoconjugates and pharmaceutical compositions described herein are useful for targeting, binding and/or detecting CD133 in cell lysates.

In yet another embodiment, the CD133-binding agents, immunoconjugates and pharmaceutical compositions described herein are useful for detecting and/or quantitating levels of expression of CD133 in a sample, optionally in a CD133 expressing cell. In one embodiment, the CD133-binding agents, immunoconjugates and pharmaceutical compositions are used to detect and/or quantitate cellular CD133 levels. In another embodiment, the CD133-binding agents, immunoconjugates and pharmaceutical compositions are useful for detecting and/or quantitating cell surface CD133 levels.

The CD133-binding agents of the disclosure may be used for detecting/quantitating both native/cell-surface expressed as well as denatured CD133. Overexpression of CD133 often correlates with a cancerous phenotype. For example, Western blotting detection of CD133 protein levels in denatured whole cell lysates using CD133-binding agents of the disclosure can be used to characterize/confirm the ability of a treatment to reduce the metastatic capacity of CD133-expressing cancer cells, since reduced total cellular CD133 protein levels has been shown to correlate with reduced metastatic capacity of the cells (see, e.g. Rappa et al. 2008).

In general, the use of binding agents for detection of analytes, such as intracellular, total cellular or surface-expressed CD133 protein, is well known in the art and may be achieved through the application of numerous approaches. These methods are generally based upon the detection of a label or marker, such as radioactive, fluorescent, biological and enzymatic tags. Examples of methods include, but are not limited to, Western blotting, enzyme linked immunosorbent assay (ELISA), immunofluorescence, immunohistochemistry and flow cytometry.

The CD133-binding agents, immunoconjugates and pharmaceutical compositions of the present disclosure are also useful for reducing and/or eliminating the level or amount of CD133 protein in a cell. Optionally, the cell is a CD133-positive cancer cell, including, but not limited to, a pancreatic cancer cell, colorectal cancer cell, breast cancer cell, colon cancer cell, gastric cancer cell, prostate cancer cell, liver cancer cell, pancreatic cancer cell, lung cancer cell, melanoma cell, brain cancer cell (optionally a glioblastoma or medulloblastoma cell) and head and neck squamous cell carcinoma cell. Reduction of total cellular CD133 protein levels in cancer cells can be used to reduce the metastatic capacity thereof (see, e.g. Rappa et al. 2008). The CD133 protein of which the levels are reduced is optionally cell surface-expressed and/or intracellular CD133. The CD133 protein in a CD133-expressing cell is optionally reduced by at least 5, 10, 15, 20, 25, 30, 35, 40, 45, 50, 55, 60, 65, 70, 75, 80, 85, 90, 95, 96, 97, 98 or 99%; or by 100%.

Targeting CD133-Expressing Cells to Immune Cells

Further, the CD133-binding agents, immunoconjugates and pharmaceutical compositions of the present disclosure are useful for engaging, targeting and/or binding cells of the immune system.

For example, in one embodiment described above, the CD133-binding agent is a bispecific antibody where one of the binding specificities is for CD133 and the other binding specificity is for an antigen expressed on an immune cell such as a T cell, macrophage or NK cell. As described above, one example of a bispecific antibody that targets T cells is a bispecific T-cell engager (BiTE).

In another embodiment described above, the CD133-binding agent is a CD133-binding chimeric antigen receptor (CAR) which includes a CD133-binding agent of the disclosure, such as a CD133-binding scFv as its antigen-binding/targeting domain.

The construction of suitable CARs and their use for targeting antigen expressing cells, commonly referred to in the art as "CAR T cell therapy", is well known in the art (see, e.g. Maus and June, 2016; Abate-Daga and Davila, 2016; Resetca et al., 2016; and Wang and Riviere, 2016). Accordingly, the bispecific antibodies and chimeric antigen receptors described herein are useful for targeting immune effector cells to CD133-expressing cells (CD133+ cells).

Also provided are methods for targeting CD133+ cells comprising exposing the CD133+ cells to an immune effector cell expressing a CAR of the disclosure, or to a combination of a bispecific antibody of the disclosure and an immune effector cell specifically bound by the bispecific antibody.

Targeting immune effector cells to CD133+ cells through these methods may be useful for eliminating, and/or shifting the phenotype of, CD133+ cancer cells from a cancerous phenotype towards a less cancerous or non-cancerous phenotype. In addition, targeting immune effector cells to CD133+ cells may be useful for treating diseases where CD133 is expressed or overexpressed such as cancer.

Diagnostic Methods

The CD133-binding agents disclosed herein are useful in the detection/quantitation of CD133 in patient samples or in control samples of healthy individuals and accordingly may be useful diagnostics. For example, the binding agents of the disclosure can be used to detect/quantitate total cellular expression of CD133 and/or cell-surface expressed CD133. As used herein, the term "diagnostics" encompasses screening, stratification, monitoring and the like.

In one embodiment, the CD133-binding agents are used to detect CD133 expressing cells, optionally cancer cells such as pancreatic cancer cells, colorectal cancer cells, breast cancer cells, colon cancer cells, gastric cancer cells, prostate cancer cells, liver cancer cells, lung cancer cells, melanoma cells, brain cancer cells and head and neck squamous cell carcinoma cells.

In another embodiment, the CD133-binding agents are used for detecting/quantitating cell surface expression of CD133. In another embodiment, the CD133-binding agents are used for detecting/quantitating intracellular expression of CD133. In another embodiment, the CD133-binding agents described herein can be used to detect/quantitate expression of CD133 in a sample.

For example, CD133-binding agents of the disclosure, such as the antibodies and antibody fragments of the disclosure, may be used for practicing any one of various assays, e.g. immunofluorescence, flow cytometry or ELISAs, to detect/quantitate CD133 levels in a sample.

In one embodiment, the sample is a patient sample, such as a cancer sample from a cancer patient. Alternately, the sample may be a control sample from a healthy individual. Embodiments of the sample include but are not limited to, a sample of cultured cells, cultured cell supernatant, cell lysate, serum, blood plasma, biological fluid or biological tissue. In other embodiments, the sample is obtained from a cancer. In certain embodiments, the sample is a biopsy sample.

Treatment of Cancer

CD133 has been shown to play an important role in various cancers. For example, CD133 has been identified as a marker for cancer stem cells (CSCs) in brain tumors (Singh et al., 2003) and it has been demonstrated that as few as 100 CD133+ cells from brain tumor fractions are sufficient to generate a tumor in NOD/SCID mice (Singh et al., 2004). Additionally, CD133+ glioma cells have been shown to have increased resistance to radiation in a DNA checkpoint dependent manner as compared with CD133-negative (CD133-) cells (Bao et al., 2006). Pancreatic CSCs have been isolated using anti-CD133 antibodies and it has been demonstrated that these cells are tumorigenic and highly resistant to standard chemotherapy (Hermann et al., 2007). Similarly, it has also been shown that increased CD133 expression in pancreatic cancer cells correlates with a more aggressive nature including increased migration and invasion and heightened tumor aggressiveness (Moriyama et al., 2010). Stem-like cells from prostate cancer tissues have been identified (Collins, 2005) and it has been demonstrated that CD133+ cells isolated from prostate cancer tissues and in an immortalized prostate cancer cell line exhibit stem cell features (Miki et al., 2007; Wei et al., 2007), however other studies have failed to confirm this (Missol-Kolka et al., 2010) and have not reported the stem-cell characteristics that others attribute to pancreatic cancer lines like the DU145 line (Pfeiffer & Schalken, 2010). Another cancer type for which CD133 is used as a CSC marker is colorectal carcinoma. Separate groups have identified CD133 as a marker of CSCs in colon cancer (O'Brien et al., 2006; Ricci-Vitiani et al., 2006). It has been demonstrated that CD133+ cells readily recapitulate tumors in SCID mice (Ricci-Vitiani et al., 2006), and that there is an enrichment of colon cancer initiating cells purified CD133+ cells compared to unfractionated tumor cells (O'Brien et al., 2006). It has been demonstrated that both CD133+ and CD133-negative cells from colon metastases are able to form colon-spheres and recapitulate tumors in NOD/SCID mice (Shmelkov, 2004). Additionally, several groups have concluded that CD133 is associated with worse clinical prognosis, disease progression and metastasis and that CD133 protein can be used as an independent prognostic marker for colorectal cancer patients (Horst et al., 2009). However, other groups have failed to find a relationship between CD133 and disease progression or survival in colon cancer patients but have instead found a relationship between the expression of the protein and tumor stage (Lugli et al., 2010).

It has been demonstrated that downregulation of CD133 in the metastatic melanoma cell line FEMX-I resulted in slower cell growth, decreased cell motility, decreased ability to form spheres in stem-cell growth conditions and a reduced metastatic capacity of tumor xenografts (Rappa et al., 2008). It has been shown that the anti-CD133 antibody AC133 conjugated to monomethyl auristatin F inhibits the growth of hepatocellular and gastric cancer cells in vitro (Smith et al., 2008), it was further demonstrated that secondary antibody conjugated to saporin in the presence of AC133 is toxic to FEMX-I cells but not control human fibroblasts (Rappa et al., 2008). Additionally, AC133 directly conjugated to saporin has been shown to be more effective against FEMX-I cells than FEMX-I cells with CD133 expression knocked down (Rappa et al., 2008). It was observed that in cells in which CD133 is knocked down, genes that became upregulated coded for wnt inhibitors (Mak et al., 2012b).

In addition, numerous studies have implicated CD133+ brain tumor initiating cells (BTICs) as drivers of chemo- and radio-resistance in glioblastoma (GBM). It has also recently been demonstrated that a CD133-driven gene signature is predictive of poor overall survival (Venugopal et al, 2015) and targeting CD133+ treatment refractory cells may be an effective strategy to block GBM recurrence.

Accordingly, these results provide support for targeting CD133 as an effective therapeutic strategy and as an effective diagnostics strategy. In addition, the present inventors have described a CAR T-cell-based strategy whereby CD133+ GBM cells are specifically targeted and killed. The present inventors have also shown that a BiTE antibody that redirects human polyclonal T cells to CD133+ GBM cells induces a potent anti-tumor response.

Accordingly, the CD133-binding agents and pharmaceutical compositions of the present disclosure are useful for treating or preventing a cancer, for example a metastatic melanoma, brain, prostate, pancreatic and/or colon/colorectal cancer. In one embodiment, the cancer is a glioblastoma. In another embodiment, the cancer is a medulloblastoma.

In another embodiment, the cancer is a CD133-positive cancer (also referred to as a CD133-expressing cancer). In one embodiment, a CD133-positive cancer is defined as a cancer with greater than 80%, 85%, 90%, 95% or 99% CD133-positive cells (i.e., CD133-expressing cells). The percentage of cells expressing CD133 may be determined, for example, in a tumor cell culture. Accordingly, in particular embodiments, the cancer is a CD133-positive glioblastoma or a CD133-positive medulloblastoma. In another embodiment, the cancer is a glioblastoma detectably expressing CD133 or a medulloblastoma detectably expressing CD133.

In one embodiment, the CD133-binding agents and pharmaceutical compositions described herein are used in a method for treating or preventing cancer, the method comprising administering an effective amount of a CD133-binding agent or pharmaceutical composition disclosed herein to an animal or cell in need thereof, optionally wherein the cancer is metastatic melanoma, brain, prostate, pancreatic and/or colon cancer. In one embodiment, the cancer is a glioblastoma or a medulloblastoma.

In another embodiment, an effective amount of a CD133-binding agent or pharmaceutical composition disclosed herein is used for treating or preventing a cancer, optionally wherein the cancer is metastatic melanoma, brain, prostate, pancreatic and/or colon cancer. In another embodiment, a CD133-binding agent or pharmaceutical composition disclosed herein is used in the preparation of a medicament for treating or preventing a cancer, optionally wherein the cancer is metastatic melanoma, brain, prostate, pancreatic and/or colon cancer. In one embodiment, the cancer is a glioblastoma or a medulloblastoma.

In yet another embodiment, an effective amount of a CD133-binding agent or pharmaceutical composition disclosed herein is used for in treating or preventing a cancer, optionally wherein the cancer is metastatic melanoma, brain, prostate, pancreatic and/or colon cancer. In one embodiment, the cancer is a glioblastoma or a medulloblastoma.

As described above, the present disclosure provides immunoconjugates comprising (1) a CD133-binding agent and (2) an effector agent, where the effector agent is optionally a toxin or an anti-neoplastic agent.

Accordingly, the present disclosure provides a method of using an immunoconjugate disclosed herein for treating or preventing a cancer, the method comprising administering an effective amount of an immunoconjugate disclosed herein to an animal or cell in need thereof, optionally wherein the cancer is metastatic melanoma, brain, prostate, pancreatic and/or colon cancer. In one embodiment, the cancer is a glioblastoma or a medulloblastoma.

In one embodiment, an effective amount of an immunoconjugate disclosed herein is used for treating or preventing a cancer, optionally wherein the cancer is metastatic melanoma, brain, prostate, pancreatic and/or colon cancer. In another embodiment, an immunoconjugate disclosed herein is used in the preparation of a medicament for treating or preventing a cancer, optionally wherein the cancer is metastatic melanoma, brain, prostate, pancreatic and/or colon cancer. In one embodiment, the cancer is a glioblastoma or a medulloblastoma.

The present disclosure also provides CARs that target CD133 expressing cells, and T-cells expressing the CARs. Accordingly, in another embodiment, the present disclosure provides a method of using a T cell expressing a CAR disclosed herein for treating or preventing a cancer, the method comprising administering an effective amount of a T cell expressing a CAR disclosed herein to an animal or cell in need thereof, optionally wherein the cancer is metastatic melanoma, brain, prostate, pancreatic and/or colon cancer. In one embodiment, the cancer is a glioblastoma or a medulloblastoma.

In one embodiment, an effective amount of a T cell expressing a CAR disclosed herein is used for treating or preventing a cancer, optionally wherein the cancer is metastatic melanoma, brain, prostate, pancreatic and/or colon cancer. In another embodiment, a T cell expressing a CAR disclosed herein disclosed herein is used in the preparation of a medicament for treating or preventing a cancer, optionally wherein the cancer is metastatic melanoma, brain, prostate, pancreatic and/or colon cancer. In one embodiment, the cancer is a glioblastoma or a medulloblastoma.

As used herein, the terms "subject" and "animal" include all members of the animal kingdom, in one embodiment the subject is a mammal. In a further embodiment the subject is a human being. In one embodiment, the subject is a patient having a disease, such as a cancer, associated with CD133-expressing cells.

The term "a cell" includes a single cell as well as a plurality or population of cells.

An effective amount of a CD133-binding agent, immunoconjugate or pharmaceutical composition of the disclosure relates generally to the amount needed to achieve a therapeutic objective. As noted above, this may be a binding interaction between the CD133-binding agent and CD133 that, in certain cases, interferes with the functioning of CD133.

The amount required to be administered will furthermore depend on the binding affinity of the CD133-binding agent for CD133, and will also depend on the rate at which an administered CD133-binding agent is depleted from the free volume of the subject to which it is administered. Common ranges for therapeutically effective dosing of a CD133-binding agent, immunoconjugate or pharmaceutical composition of the disclosure may be, by way of non-limiting example, from about 0.1 mg kg body weight to about 50 mg/kg body weight. Common dosing frequencies may range, for example, from twice daily to once a week.

Efficaciousness of treatment is determined in association with any known method for diagnosing or treating the particular cancer. Alleviation of one or more symptoms of the cancer indicates that the antibody confers a clinical benefit.

As used herein, "treating a cancer" includes, but is not limited to, reversing, alleviating or inhibiting the progression of the cancer or symptoms or conditions associated with the cancer. "Preventing a cancer" includes preventing incidence or recurrence of the cancer. "Treating a cancer" also includes extending survival in a subject. Survival is optionally extended by at least 1, 2, 3, 6 or 12 months, or at least 2, 3, 4, 5 or 10 years over the survival that would be expected without treatment with a CD133-binding agent, immunoconjugate or pharmaceutical composition as described herein. "Treating a cancer" also includes reducing tumor mass and/or reducing tumor burden (for example, brain tumor mass and/or brain tumor burden). Optionally, tumor mass or tumor burden is reduced by at least 5, 10, 25, 50, 75 or 100% following treatment with a CD133-binding agent, immunoconjugate or pharmaceutical composition as described herein. In other embodiments, "treating a cancer" includes reducing the aggressiveness, grade and/or invasiveness of a tumor. The tumor is optionally a newly formed tumor or a tumor already present at the time of treatment.

In one embodiment, the active ingredient may be used in combination with at least one additional therapeutic agent. Accordingly, the application provides a method of preventing or treating a cancer using the CD133-binding agents, immunoconjugates or pharmaceutical compositions disclosed herein in combination with at least one additional therapeutic agent. An additional therapeutic agent may be administered prior to, overlapping with, concurrently, and/or after administration of the active ingredients. When administered concurrently, the CD133-binding agents, immunoconjugates or pharmaceutical compositions and an additional therapeutic agent may be administered in a single formulation or in separate formulations, and if administered separately, then optionally, by different modes of administration. The combination of one or more CD133-binding agents, immunoconjugates or pharmaceutical compositions and one or more other therapeutic agents may synergistically act to combat the cancer.

Embodiments of the additional therapeutic agent include additional CD133-binding agents, additional CD133-binding immunoconjugates, additional CD133-binding pharmaceutical compositions, cytokines, growth factor inhibitors, immunosuppressants, anti-inflammatory agents, metabolic inhibitors, enzyme inhibitors, anti-neoplastic agents, cytotoxic agents and/or cytostatic agents. Such combination therapies may advantageously utilize lower dosages of an administered active ingredient, thus avoiding possible toxicities or complications associated with monotherapy.

Screening Assays

The disclosure also provides methods (also referred to herein as "screening assays") for identifying modulators, i.e., test agents (e.g. peptides, peptidomimetics, small molecules or other drugs) that modulate or otherwise interfere with the binding of a protein disclosed herein with the CD133.

The test agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection (see, e.g. Lam, 1997).

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1: Cell Selections and Sequencing

In order to attempt to discover novel antibodies capable of specifically binding CD133, two phage-display libraries, Library F and Library G, were screened for cell surface CD133 binders using the "Cellectseq" method (the Cellectseq method, Library F and Library G have been previously described, e.g. in U.S. patent application Ser. No. 13/629,520). Briefly, Library F is a Fab library with diversity in light chain complementarity-determining region (CDR) 3 and in all three heavy chain CDRs, and Library G is scFv library with diversity in all six CDRs. The cells used for the selections were HEK293 cells engineered to overexpress CD133 (GenBank™ Accession 043490) for the positive selection and the parental HEK293 cells were used for the negative selection. After four rounds of positive and negative selection, serial dilutions were made of the round four output phage (10E-1 to 10E-3) for each library and used to infect XLI-blue cells. The infected cells were plated for isolating single colonies to be used in a clonal cell-based ELISA for isolating CD133-specific binders. Clones that bound to the HEK293-CD133 cells and generated an ELISA signal that was at least 1.5 fold higher than background binding to HEK293 cells were classified as CD133-specific binders. Sequencing was performed by amplifying the antibody variable (VL and VH) domains from clone DNA with M13-tagged sequencing primers, and the amplified sequences were sequenced via Illumina sequencing. The full-length amino acid sequence of human CD133 expressed in HEK293-CD133 cells is indicated in Table 1. The amino acid sequence coordinates of the three extracellular domains of CD133 are as follows: Gly20-Gly108, Ala179-Tyr433 and Gly508-Asn792. The amino acid sequence coordinates of the segment spanning all three extracellular domains is Gly20-Asn792. The signal sequence corresponding to Met1-Ser19 of the full-length sequence is absent from the mature, cell-surface expressed CD133 protein.

TABLE 1

Amino acid sequence of human CD133 (GenBank™ Accession 043490).

*MALVLGSLLLLGLCGNSFSGGQPSSTDAPKAWNYELPATNYETQDSHKAG*

PIGILFELVHIFLYVVQPRDFPEDTLRKFLQKAYESKIDYDKPETVILGL

KIVYYEAGIILCCVLGLLFIILMPLVGYFFCMCRCCNKCGGEMHQRQKEN

GPFLRKCFAISLLVICIIISIGIFYGFV<u>ANHQVRTRIKRSRKLADSNFKD</u>

<u>LRILLNETPEQIKYILAQYNTTKDKAFTDLNSINSVLGGGILDRLRPNII</u>

<u>PVLDEIKSMATAIKETKEALENMNSTLKSLHQQSTQLSSSLTSVKISLRS</u>

<u>SLNDPLCLVHPSSETCNSIRLSLSQLNSNPELRQLPPVDAELDNVNNVLR</u>

<u>TDLDGLVQQGYQSLNDIPDRVQRQTTTVVAGIKRVLNSIGSDIDNVTQRL</u>

<u>PIQDILSAFSVYVNNTESYIHRNLPTLEEYDSYWWLGGLVICSLLTLIVI</u>

FYYLGLLCGVCGYDRHATPTTRGCVSNTGGVFLMVGVGLSFLFCWILMII

VVLTFVF<u>GANVEKLICEPYISKELFRVLDTPYLLNEDWEYYLSGKLFNKS</u>

<u>KMKLTFEQVYSDCKKNRGTYGTLHLQNSFNISEHLNINEHTGSISSELES</u>

<u>LKVNLNIFLLGAAGRKNLQDFAACGIDRMNYDSYLAQTGKSPAGVNLLSF</u>

<u>AYDLEAKANSLPPGNLRNSLKRDAQTIKTIHQQRVLPIEQSLSTLYQSVK</u>

<u>ILQRTGNGLLERVIRILASLDFAQNFITNNTSSVIIEETKKYGRTIIGYF</u>

<u>EHYLQWIEFSISEKVASCKPVATALDTAVDVFLCSYIIDPLNLFWFGIGK</u>

ATVFLLPALIFAVKLAKYYRRMDSEDVYDDVETIPMKNMENGNNGYHKDH

VYGIHNPVMTSPSQH
(SEQ ID NO: 1)

The 3 extracellular domains of CD133 are underlined.

TABLE 1-continued

Amino acid sequence of human CD133 (GenBank™ Accession 043490).

Italics indicate signal sequence absent from mature, surface-expressed polypeptide.

Example 2: Discovery and Characterization of Novel Antibody Variable Regions RW01 and RW03 Capable of Specifically Binding Human CD133

Cell Selections and Sequencing Data:
Cell-based selections for CD133-binding phage-Fab or phage-scFv were performed using the Cellectseq method as described in Example 1. Out of 94 phage-Fab clones selected from the Library F output and subjected to ELISA for determining their CD133-binding specificity, 77 clones were found to bind to HEK293-CD133 cells at levels at least 1.5-fold higher than to control HEK293 cells (FIG. 1A). In contrast, none of the clones selected from the Library G output exhibited this CD133-binding specificity. The 94 clones selected from Library F were sequenced by amplifying DNA encoding the Fab variable regions (VL and VH regions) using M13-tagged sequencing primers. The Library F and Library G round three and four positive and negative outputs were sequenced via Illumina sequencing to identify binders enriched in the positive selection output pools. The sequencing results indicated that 91 of the 94 clones were composed of clones each having one of 3 unique antibody variable regions, as represented by clones "phage-Fab RW03", "phage-Fab C12" and "phage-Fab F5". Specifically, out of the 94 clones, 89 clones shared the same variable region sequences, 2 clones had unique variable region sequences, and no sequence was obtained for 3 clones.

Figure 1B:
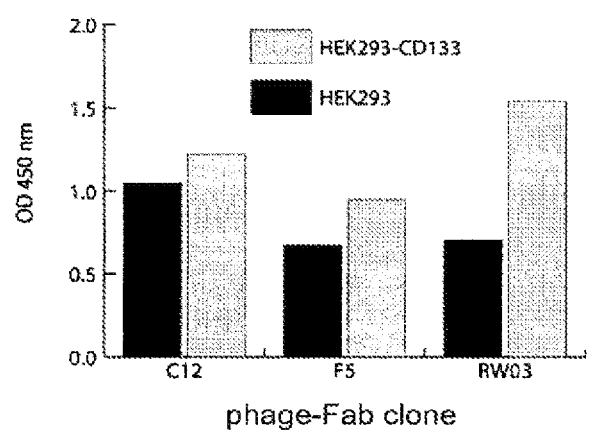
Figure 2:
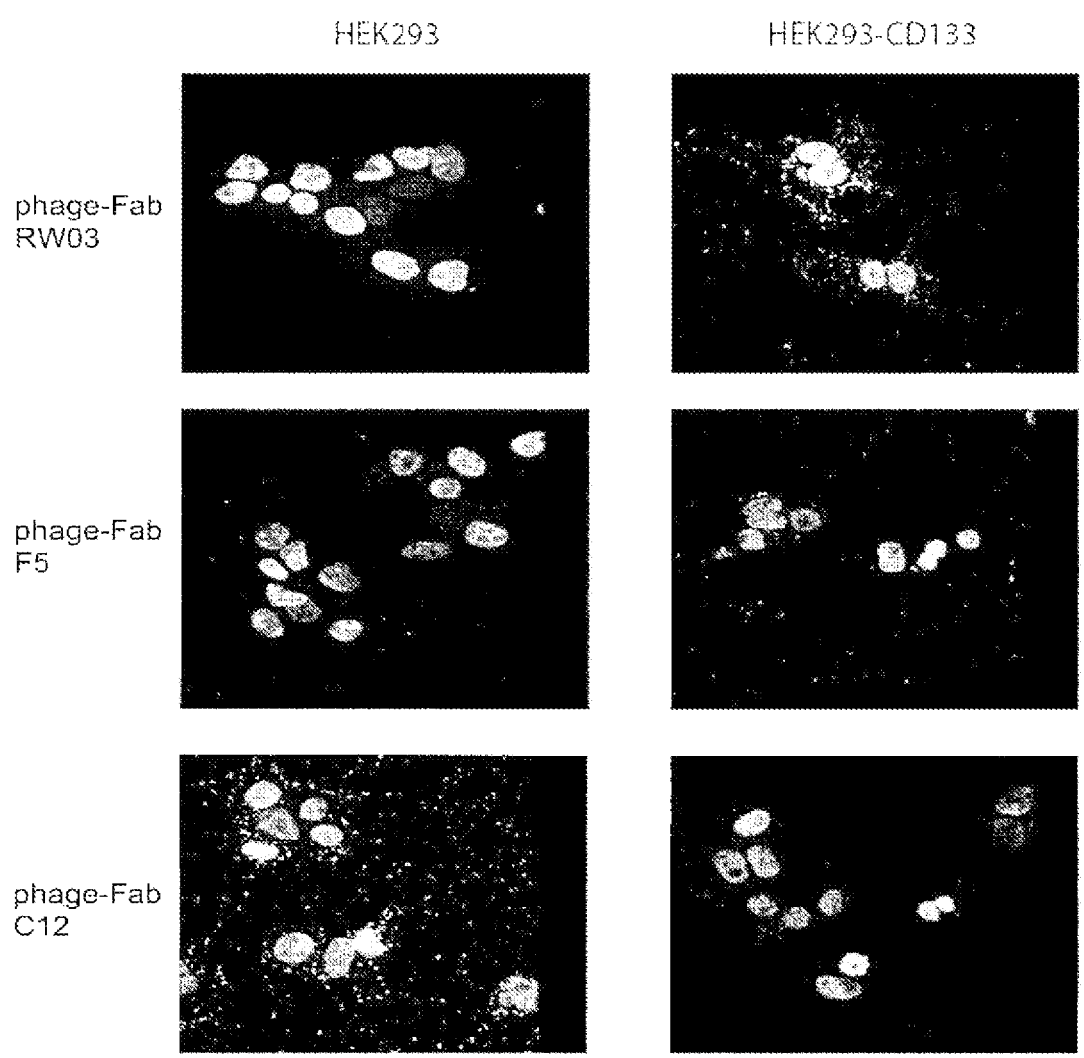
Figure 3A:
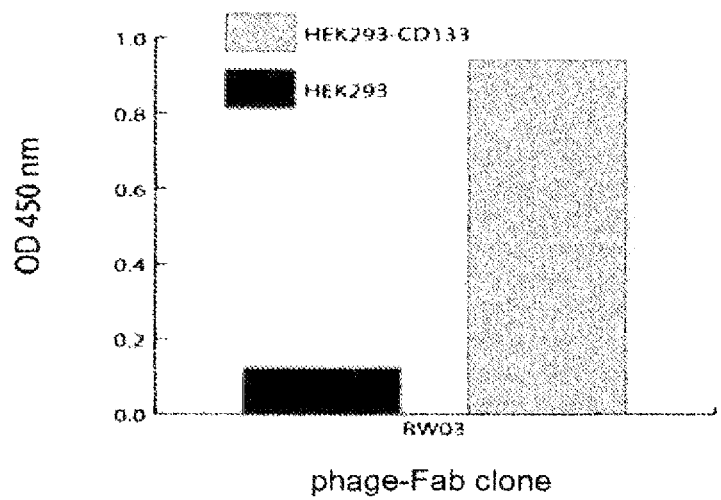
Figure 3B:
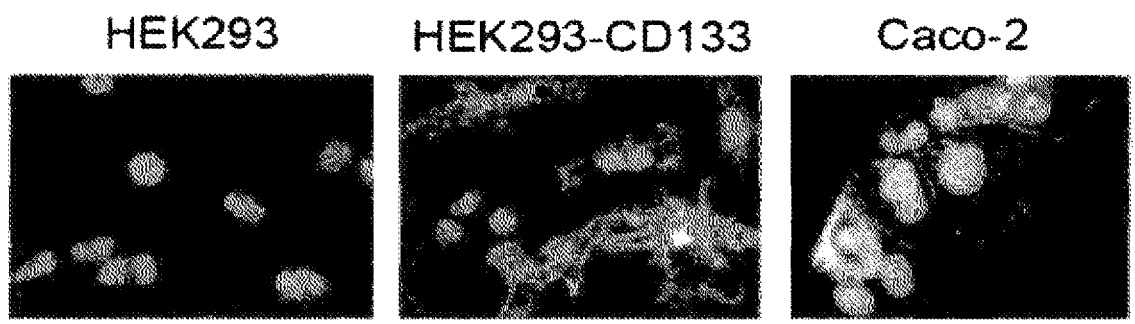

FIG. 1B shows representative cell-based ELISA results for binding to HEK293-CD133 and HEK293 cells by phage-Fab RW03 comprising "antibody variable region RW03", phage-Fab C12 and phage-Fab F5. Only phage-Fab RW03 showed preferential binding to HEK293-CD133 cells vs HEK293 cells by a factor of at least 1.5. The Fab-encoding DNA sequences of phage-Fab RW03, phage-Fab C12 and phage-Fab F5 were each cloned into an IPTG-inducible vector for protein expression and the expressed Fabs ("Fab RW03", "Fab C12" and "Fab F5", respectively) were purified for testing via immunofluorescence (IF) assay, the results of which are shown in FIG. 2. The IF assay showed that Fab RW03 demonstrated highly specific binding to the HEK293-CD133 cells, with very little background binding to HEK293 cells, whereas Fab C12 and Fab F5 were found to bind non-specifically to both HEK293-CD133 cells and HEK293 cells. The specific binding of Fab RW03 to HEK293-CD133 cells was also confirmed by cell-based ELISA (FIG. 3A). Furthermore, Fab RW03 also was found to bind to Caco-2 cells, which is a colorectal cancer cell line known to express CD133 (FIG. 3B). These results were consistent with the Illumina sequencing results in which the variable region DNA sequences of phage-Fab clone C12 and phage-Fab clone F5 appeared in both the positive as well as the negative selection output pools whereas those of phage-Fab RW03 appear only in the positive selection pool (data not shown). Additionally, the phage-Fab RW03 DNA sequence was the most abundant sequence in both the round 3 and 4 output pools, which is also consistent with the results of the cell-based ELISA in which the DNA sequences of 94% of the phage-Fab binders were those of phage-Fab RW03.

In addition to determining the DNA sequences encoding CD133-binding phage-Fabs from Library F, the Illumina sequencing data from Library G selection output pools was also analyzed to identify enriched binders (data not shown). DNA encoding the variable regions of 12 selected phage-scFv clones was rescued via PCR amplification and used to generate expression vectors for expression of 12 IgGs having variable regions corresponding to those of the 12 selected phage-scFv clones. Of these 12 IgGs, "IlgG RW01" containing "antibody variable region RW01" derived from phage-scFv clone RW01 was validated for specifically binding to CD133+ cells by flow cytometry analysis. Similarly, "IlgG RW03" having "antibody variable region RW03" corresponding to that of Fab RW03 was produced and IgG RW01 and IgG RW03 were further tested in parallel.

The amino acid sequences of light chain (hK) and heavy chain of IgG RW01 and IgG RW03, and of the heavy and light chain variable domains of antibody variable regions RW01 and RW03 are shown in Table 2, and the amino acid sequences of complementarity-determining regions (CDRs) and heavy chain variable domain residues at positions 39, 55 and 66 of antibody variable region RW01 comprised in IgG RW01 and of antibody variable region RW03 comprised in IgG RW03 are indicated in Table 3. The nucleotide sequences encoding the CDRs and heavy chain variable domain residues at positions 39, 55 and 66 of antibody variable region RW01 comprised in IgG RW01 and of antibody variable region RW03 comprised in IgG RW03 are indicated in Table 4. The amino acid sequence of the light chain variable domain of IgG RW01 corresponds to that of the Asp1 to Lys106 segment of SEQ ID NO: 2; the amino acid sequence of the heavy chain variable domain of IgG RW01 corresponds to that of the Glu1 to Thr120 segment of SEQ ID NO: 3; the amino acid sequence of the light chain variable domain of IgG RW03 corresponds to that of the Asp1 to Lys109 segment of SEQ ID NO: 4; and the amino acid sequence of the heavy chain variable domain of IgG RW03 corresponds to that of the Glu1 to Ser118 segment of SEQ ID NO: 5.

TABLE 2

Amino acid sequences of light chain (hK) and heavy chain of IgG RW01 and IgG RW03, and of heavy and light chain variable domains of antibody variable regions RW01 and RW03.

Light chain variable domain of antibody variable region RW01:

DIQMTQSPSSLSASVGDRVTITCRAS<u>QGSSY</u>VAWYQQKPGKAPKLLIY<u>SA</u>
<u>SYLY</u>SGVPSRFSGSRSGTDFTLTISSLQPEDFATYYC<u>QQGVWSLIT</u>FGQG
TKVEIK
(SEQ ID NO: 28)

Heavy chain variable domain of antibody variable region RW01:

EVQLVESGGGLVQPGGSLRLSCAAS<u>GFNTYYYGS</u><sup>M</sup>HWVRQAPGK
GLEWVA<sup>S</sup><u>ISPYYGST</u><sup>Y</sup>YADSVKGRFTISADTSKNTAYLQMNSL
RAEDTAVYYC<u>ARHASSGYGHYAVYGID</u>YWGQGTLVTVSS
(SEQ ID NO: 29)

IgG RW01 - Light chain (hK) amino acid sequence:

DIQMTQSPSSLSASVGDRVTITCRAS<u>QGSSY</u>VAWYQQKPGKAPKLLIY<u>SA</u>
<u>SYLY</u>SGVPSRFSGSRSGTDFTLTISSLQPEDFATYYC<u>QQGVWSLIT</u>FGQG
TKVEIK*RTVAAPSVFIFPPSDEQLKSGTASVVCLLNNFYPREAKVQWKVD*
*NALQSGNSQESVTEQDSKDSTYSLSSTLTLSKADYEKHKVYACEVTHQGL*
*SSPVTKSFNRGEC*
(SEQ ID NO: 2)

TABLE 2-continued

Amino acid sequences of light chain (hK) and heavy chain of IgG RW01 and IgG RW03, and of heavy and light chain variable domains of antibody variable regions RW01 and RW03.

IgG RW01 - Heavy chain (hG1) amino acid sequence:

EVQLVESGGGLVQPGGSLRLSCAAS<u>GFNIYYYGS</u><sup>M</sup>HWVRQAPG
KGLEWVA<sup>S</sup><u>ISPYYGST</u><sup>Y</sup>YADSVKGRFTISADTSKNTAYLQMNSL
RAEDTAVYYC<u>ARHASSGYGHYAVYGID</u>YWGQGTLVTVSS*ASTKGPSVFPL*
*APSSKSTSGGTAALGCLVKDYFPEPVTVSWNSGALTSGVHTFPAVLQSSG*
*LYSLSSVVTVPSSSLGTQTYICNVNHKPSNTKVDKKVEPKSCDKTHTCPP*
*CPAPELLGGPSVFLEPPKPKDTLMISRTPEVTCVVVDVSREDPEVKFNWY*
*VDGVEVHNAKTKPREEQYNSTYRVVSVLTVLHQDWLNGKEYKCKVSNKAL*
*PAPIEKTISKAKGQPREPQVYTLPPSREEMTKNQVSLTCLVKGFYPSDIA*
*VEWESNGQPENNYKTTPPVLDSDGSFFLYSKLTVDKSRWQQGNVFSCSVM*
*HEALHNHYTQKSLSLSPGK*
(SEQ ID NO: 3)

Light chain variable domain of antibody variable region RW03:

DIQMTQSPSSLSASVGDRVTITCRAS<u>QSVSS</u>AVAWYQQKPGKAPKLLIY<u>S</u>
<u>ASSLY</u>SGVPSRFSGSRSGTDFTLTISSLQPEDFATYYC<u>QQYSHAGHLFT</u>F
GQGTKVEIK
(SEQ ID NO: 30)

Heavy chain variable domain of antibody variable region RW03:

EVQLVESGGGLVQPGGSLRLSCAAS<u>GFNLSSSS</u><sup>I</sup>HWVRQAPG
KGLEWVA<sup>Y</sup><u>IYPYYSYT</u><sup>Y</sup>YADSVKGRFTISADTSKNTAYLQMNS
LRAEDTAVYYC<u>ARFGSVAGFD</u>YWGQGTLVTVSS
(SEQ ID NO: 31)

IgG RW03 - Light chain (hK) amino acid sequence:

DIQMTQSPSSLSASVGDRVTITCRAS<u>QSVSS</u>AVAWYQQKPGKAPKLLIY<u>S</u>
<u>ASSLY</u>SGVPSRFSGSRSGTDFTLTISSLQPEDFATYYC<u>QQYSHAGHLFT</u>F
GQGTKVEIK*RTVAAPSVFIFPPSDEQLKSGTASVVCLLNNFYPREAKVQW*
*KVDNALQSGNSQESVTEQDSKDSTYSLSSTLTLSKADYEKHKVYACEVTH*
*QGLSSPVTKSFNRGEC*
(SEQ ID NO: 4)

IgG RW03 - Heavy chain (hG1) amino acid sequence:

EVQLVESGGGLVQPGGSLRLSCAAS<u>GFNLSSSS</u><sup>I</sup>HWVRQAPG
KGLEWVA<sup>Y</sup><u>IYPYYSYT</u><sup>Y</sup>YADSVKGRFTISADTSKNTAYLQMN
SLRAEDTAVYYC<u>ARFGSVAGFD</u>YWGQGTLVTVSS*ASTKGPSVFPLAPSSK*
*STSGGTAALGCLVKDYFPEPVTVSWNSGALTSGVHTFPAVLQSSGLYSLS*
*SVVTVPSSSLGTQTYICNVNHKPSNTKVDKKVEPKSCDKTHTCPPCPAPE*
*LLGGPSVFLFPPKPKDTLMISRTPEVTCVVVDVSREDPEVKFNWYVDGVE*
*VHNAKTKPREEQYNSTYRVVSVLTVLHQDWLNGKEYKCKVSNKALPAPIE*
*KTISKAKGQPREPQVYTLPPSREEMTKNQVSLTCLVKGFYPSDIAVEWES*
*NGQPENNYKTTPPVLDSDGSFFLYSKLTVDKSRWQQGNVFSCSVMHEALH*
*NHYTQKSLSLSPGK*
(SEQ ID NO: 5)

Underline identifies CDR sequence amino acid residues.
Large font identifies FR amino acid residues at positions 39, 55 or 66 randomized in the selection library used to identify antibody variable regions.
Italics identifies immunoglobulin constant region amino acid residues or nucleotide sequences encoding immunoglobulin constant region amino acid residues.

TABLE 3

Amino acid sequences of CDRs and of FR residues at heavy chain variable domain positions 39, 55 and 66 of antibody variable region RW01 and antibody variable region RW03.

| Antibody | Antibody segment | Amino acid sequence |
|---|---|---|
| IgG | CDR-L1 | QGSSY |

TABLE 3-continued

Amino acid sequences of CDRs and of FR residues at heavy chain variable domain positions 39, 55 and 66 of antibody variable region RW01 and antibody variable region RW03.

| Antibody | Antibody segment | Amino acid sequence |
|---|---|---|
| RW01 | | (SEQ ID NO: 6) |
| | CDR-L2 | SAS (SEQ ID NO: 7) |
| | CDR-L3 | QQGVWSLIT (SEQ ID NO: 8) |
| | CDR-H1 | GFNIYYYGS (SEQ ID NO: 9) |
| | CDR-H2 | ISPYYGST (SEQ ID NO: 10) |
| | CDR-H3 | ARHASSGYGHYAVYGIDY (SEQ ID NO: 11) |
| | VH domain position 39 (adjacent to carboxy terminal residue of CDR-H1; FR2 residue) | Met |
| | VH domain position 55 (adjacent to amino terminal residue of CDR-H2; FR2 residue) | Ser |
| | VH domain position 66 (adjacent to carboxy terminal residue of CDR-H2; FR3 residue) | Tyr |
| | Segment spanning CDR-H1 (underlined) and VH domain position 39 | GSMIYYYGS (SEQ ID NO: 32) |
| | Segment spanning VH domain position 55, CDR-H2 (underlined) and VH domain position 66 | SISPYYGSTY (SEQ ID NO: 33) |
| IgG RW03 | CDR-L1 | QSVSSA (SEQ ID NO: 12) |
| | CDR-L2 | SAS (SEQ ID NO: 13) |
| | CDR-L3 | QQYSHAGHLFT (SEQ ID NO: 14) |
| | CDR-H1 | GFNLSSSS (SEQ ID NO: 15) |
| | CDR-H2 | IYPYYSYT (SEQ ID NO: 16) |
| | CDR-H3 | ARFGSVAGFDY (SEQ ID NO: 17) |
| | VH domain position 39 (adjacent to carboxy terminal residue of CDR-H1; FR2 residue) | Ile |
| | VH domain position 55 (adjacent to amino terminal residue of CDR-H2; FR2 residue) | Tyr |
| | VH domain position 66 (adjacent to carboxy terminal residue of CDR-H2; FR3 residue) | Tyr |
| | Segment spanning CDR-H1 (underlined) and VH domain position 39 | GFNLSSSSI (SEQ ID NO: 34) |
| | Segment spanning VH domain position 55, CDR-H2 (underlined) and VH domain position 66 | YIYPYYSYTY (SEQ ID NO: 35) |

TABLE 4

Nucleotide sequences encoding complementarity-determining regions (CDRs) and FR residues at heavy chain variable domain positions 39, 55 and 66 of antibody variable region RW01 and antibody variable region RW03.

| Antibody | Antibody segment | Nucleotide sequence |
|---|---|---|
| IgG RW01 | CDR-L1 | CAGGGTTCTTCTTAC (SEQ ID NO: 36) |
| | CDR-L2 | TCTGCATCC (SEQ ID NO: 37) |
| | CDR-L3 | CAGCAAGGTGTTTGGTCTCTGATCACG (SEQ ID NO: 38) |
| | CDR-H1 | GGCTTCAACATCTACTACTACGGTTCT (SEQ ID NO: 39) |
| | CDR-H2 | ATTTCTCCTTACTACGGCTCTACT (SEQ ID NO: 40) |
| | CDR-H3 | GCTCGCCATGCTTCTTCTGGTTACGGTCATTACGCTGTTTACGGTATTGACTAC (SEQ ID NO: 41) |
| | VH domain position 39 (adjacent to carboxy terminal residue of CDR-H1; FR2 residue) | ATG |
| | VH domain position 55 (adjacent to amino terminal residue of CDR-H2; FR2 residue) | TCT |
| | VH domain position | TAC |

TABLE 4-continued

Nucleotide sequences encoding complementarity-determining regions (CDRs) and FR residues at heavy chain variable domain positions 39, 55 and 66 of antibody variable region RW01 and antibody variable region RW03.

| Antibody | Antibody segment | Nucleotide sequence |
|---|---|---|
| | 66 (adjacent to carboxy terminal residue of CDR-H2; FR3 residue) | |
| | Segment spanning CDR-H1 (underlined) and VH domain position 39 | GGCTTCAACATCTACTACTACGGTTCTATG (SEQ ID NO: 42) |
| | Segment spanning VH domain position 55, CDR-H2 (underlined) and VH domain position 66 | TCTATTTCTCCTTACTACGGCTCTACTTAC (SEQ ID NO: 43) |
| IgG RW03 | CDR-L1 | CAGTCCGTGTCCAGCGCT (SEQ ID NO: 44) |
| | CDR-L2 | TCGGCATCC (SEQ ID NO: 45) |
| | CDR-L3 | CAGCAATACTCTCATGCTGGTCATCTGTTCACG (SEQ ID NO: 46) |
| | CDR-H1 | GGCTTCAACCTCTCTTCTTCTTCT (SEQ ID NO: 47) |
| | CDR-H2 | ATTTATCCTTATTATAGCTATACT (SEQ ID NO: 48) |
| | CDR-H3 | GCTCGCTTCGGTTCTGTTGCTGGTTTTGACTAC (SEQ ID NO: 49) |
| | VH domain position 39 (adjacent to carboxy terminal residue of CDR-H1; FR2 residue) | ATC |
| | VH domain position 55 (adjacent to amino terminal residue of CDR-H2; FR2 residue) | TAT |
| | VH domain position 66 (adjacent to carboxy terminal residue of CDR-H2; FR3 residue) | TAT |
| | Segment spanning CDR-H1 (underlined) and VH domain position 39 | GGCTTCAACCTCTCTTCTTCTTCTATC (SEQ ID NO: 50) |
| | Segment spanning VH domain position 55, CDR-H2 (underlined) and VH domain position 66 | TATATTTATCCTTATTATAGCTATACTTAT (SEQ ID NO: 51) |

The nucleotide sequences of DNA encoding light chain (hK) and heavy chain of IgG RW01 and IgG RW03, and the heavy chain and light chain variable domains of antibody variable regions RW01 and RW03 are shown in Table 5.

TABLE 5

Nucleotide sequences of DNA encoding light chain (hK) and heavy chain of IgG RW01 and IgG RW03, and heavy chain and light chain variable domains of antibody variable regions RW01 and RW03.

Light chain variable domain of antibody variable region RW01:

5'-GATATCCAGATGACCCAGTCCCCGAGCTCCCTGTCCGCCTCTGTGGG
CGATAGGGTCACCATCACCTGCCGTGCCAGTCAGGGTTCTTCTTACGTAG
CCTGGTATCAACAGAAACCAGGAAAAGCTCCGAAGCTTCTGATTTACTCT
GCATCCTACCTCTACTCTACTCTGGAGTCCCTTCTCGCTTCTCTGGTAGC
CGTTCCGGGACGGATTTCACTCTGACCATCAGCAGTCTGCAGCCGGAAGA
CTTCGCAACTTATTACTGTCAGCAAGGTGTTTGGTCTCTGATCACGTTCG
GACAGGGTACCAAGGTGGAGATCAAA-3'
(SEQ ID NO: 52)

Heavy chain variable domain of antibody variable region RW01:

5'-GAGGTTCAGCTGGTGGAGTCTGGCGGTGGCCTGGTGCAGCCAGGGGG
CTCACTCCGTTTGTCCTGTGCAGCTTCTGGCTTCAACCTCTCTTCTTCTT
CTATCCACTGGGTGCGTCAGGCCCCGGGTAAGGGCCTGGA
ATGGGTTGCATATATTTATCCTTATTATAGCTATACT

TABLE 5-continued

Nucleotide sequences of DNA encoding light chain (hK) and heavy chain of IgG RW01 and IgG RW03, and heavy chain and light chain variable domains of antibody variable regions RW01 and RW03.

TAT<sub>T</sub>TATGCCGATAGCGTCAAGGGCCGTTTCACTATAA
GCGCAGACACATCCAAAAACACAGCCTACCTACAAATGAACAGCTTAAGA
GCTGAGGACACTGCCGTCTATTATTGT<u>GCTCGCTTCGGTTCTGTTGCTGG
TTTTGACTAC</u>TGGGGTCAAGGAACCCTGGTCACCGTCTCCTCG-3'
(SEQ ID NO: 53)

IgG RW01 - Light chain (hK) nucleotide sequence:

5'-GATATCCAGATGACCCAGTCCCCGAGCTCCCTGTCCGCCTCTGTGGG
CGATAGGGTCACCATCACCTGCCGTGCCAGT<u>CAGGGTTCTTCTTACGTAG
CCTGGTATCAACAGAAACCAGGAAAAGCTCCGAAGCTTCTGATTTAC</u>TCT
GCATCCTACCTCTACTCTACTCTGGAGTCCCTTCTCGCTTCTCTGGTAGC
CGTTCCGGGACGGATTTCACTCTGACCATCAGCAGTCTGCAGCCGGAAGA
CTTCGCAACTTATTACTGT<u>CAGCAAGGTGTTTGGTCTCTGATCAC</u>GTTCG
GACAGGGTACCAAGGTGGAGATCAAACGTACGGTGGCTGCACCATCTGTC
TTCATCTTCCCGCCATCTGATGAGCAGTTGAAATCTGGAACTGCCTCTGT
TGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAG
CAGGACAGCAAGGACAGCACCTACAGCCTCAGCAGCACCCTGACGCTGAG
CAAAGCAGACTACGAGAAACACAAAGTCTACGCCTGCGAAGTCACCCATC
AGGGCCTGAGCTCGCCCGTCACAAAGAGCTTCAACAGGGGAGAGTGT-3'
(SEQ ID NO: 18)

IgG RW01 - Heavy chain (hG1) nucleotide sequence:

5'-GAGGTTCAGCTGGTGGAGTCTGGCGGTGGCCTGGTGCAGCCAGGGGG
CTCACTCCGTTTGTCCTGTGCAGCTTCT<u>GGCTTCAACATCTACTACTACG
GTTCT</u>ATGCACTGGGTGCGTCAGGCCCCGGGTAAGGGCCT
GGAATGGGTTGCA<sub>TCT</sub>ATTTCTCCTTACTACGGCTCTACT
TAC<sub>ATGCCGATAGCGTCAAGGGCCGTTTCACTATAAGC
CAGACACATCCAAAAACACAGCCTACCTACAAATGAACAGCTTAAGAGCT
GAGGACACTGCCGTCTATTATTGT<u>GCTCGCCATGCTTCTTCTGGTTACGG
TCATTACGCTGTTTACGGTATTGACTAC</u>TGGGGTCAAGGAACCCTGGTCA
CCGTCTCCTCGGCTAGCACCAAGGGCCCATCGGTCTTCCCCCTGGCACCC
TCCTCCAAGAGCACCTCTGGGGGCACAGCGGCCCTGGGCTGCCTGGTCAA
GGACTACTTCCCCGAACCGGTGACGGTGTCGTGGAACTCAGGCGCCCTGA
CCAGCGGCGTGCACACCTTCCCGGCTGTCCTACAGTCCTCAGGACTCTAC
TCCCTCAGCAGCGTGGTGACCGTGCCCTCCAGCAGCTTGGGCACCCAGAC
CTACATCTGCAACGTAATCACAAGCCCAGCAACACCAAGGTGGACAAGA
AAGTTGAGCCCAAATCTTGTGACAAAACTCACACATGCCCACCGTGCCCA
GCACCTGAACCTCCTGGGGGACCGTCAGTCTTCCTCTTCCCCCCAAAACC
CAAGGACACCCTCATGATCTCCCGGACCCCTGAGGTCACATGCGTGGTGG
TGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAA
CAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCC
CCCATCGAGAAAACCATCTCCAAAGCCAAAGGGCAGCCCCGAGAACCACA
GGTGTACACCCTGCCCCCATCCCGGGAGGAGATGACCAAGAACCAGGTCA
GCCTGACCTGCCTGGTCAAAGGCTTCTATCCCAGCGACATCGCCGTGGAG
TGGGAGAGCAATGGGCAGCCGGAGAACAACTACAAGACCACGCCTCCCGT
GCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAG
GCTCTGCACAACCACTACACGCAGAAGAGCCTCTCCCTGTCTCCGGGTAA
A-3'
(SEQ ID NO: 19)

Light chain variable domain of antibody variable region RW03:

5'-GATATCCAGATGACCCAGTCCCCGAGCTCCCTGTCCGCCTCTGTGGG
CGATAGGGTCACCATCACCTGCCGTGCCAGT<u>CAGTCCGTGTCCAGCGCTG
TAGCCTGGTATCAACAGAAACCAGGAAAAGCTCCGAAGCTTCTGATTTAC
TCGGCATCC</u>AGCCTCTACTCTACTCTGGAGTCCCTTCTCGCTTCTCTGGT
AGCCGTTCCGGGACGGATTTCACTCTGACCATCAGCAGTCTGCAGCCGGA
AGACTTCGCAACTTATTACTGT<u>CAGCAATACTCTCATGCTGGTCATCTGT
TCACG</u>TTCGGACAGGGTACCAAGGTGGAGATCAAA-3'
(SEQ ID NO: 54)

Heavy chain variable domain of antibody variable region RW03:

5'-GAGGTTCAGCTGGTGGAGTCTGGCGGTGGCCTGGTGCAGCCAGGGGG
CTCACTCCGTTTGTCCTGTGCAGCTTCT<u>GGCTTCAACCTCTCTTCTTCTT

TABLE 5-continued

Nucleotide sequences of DNA encoding light chain (hK) and heavy chain of IgG RW01 and IgG RW03, and heavy chain and light chain variable domains of antibody variable regions RW01 and RW03.

CT</u><sub>CT</sub>ATC<sub>C</sub>CACTGGGTGCGTCAGGCCCCGGGTAAGGGCCTG
GAATGGGTTGCA<sub>TAT</sub>ATTTATCCTTATTATAGCTATAC
<sub>T</sub>TAT<sub>T</sub>TATGCCGATAGCGTCAAGGGCCGTTTCACTATAA
GCGCAGACACATCCAAAAACACAGCCTACCTACAAATGAACAGCTTAAGA
GCTGAGGACACTGCCGTCTATTATTGT<u>GCTCGCTTCGGTTCTGTTGCTGG
TTTTGACTAC</u>TGGGGTCAAGGAACCCTGGTCACCGTCTCCTCG-3'
(SEQ ID NO: 55)

IgG RW03 - Light chain (hK) nucleotide sequence:

5'-GATATCCAGATGACCCAGTCCCCGAGCTCCCTGTCCGCCTCTGTGGG
CGATAGGGTCACCATCACCTGCCGTGCCAGT<u>CAGTCCGTGTCCAGCGCTG
TAGCCTGGTATCAACAGAAACCAGGAAAAGCTCCGAAGCTTCTGATTTAC
TCGGCATCC</u>AGCCTCTACTCTACTCTGGAGTCCCTTCTCGCTTCTCTGGT
AGCCGTTCCGGGACGGATTTCACTCTGACCATCAGCAGTCTGCAGCCGGA
AGACTTCGCAACTTATTACTGT<u>CAGCAATACTCTCATGCTGGTCATCTGT
TCACG</u>TTCGGACAGGGTACCAAGGTGGAGATCAAACGTACGGTGGCTGCA
CCATCTGTCTTCATCTTCCCGCCATCTGATGAGCAGTTGAAATCTGGAAC
TGCCTCTGTTGTGTGCCTGCTGAATAACTTCTATCCCAGAGAGGCCAAAG
TACAGTGGAAGGTGGATAACGCCCTCCAATCGGGTAACTCCCAGGAGAGT
GTCACAGAGCAGGACAGCAAGGACAGCACCTACAGCCTCAGCAGCACCCT
GACGCTGAGCAAAGCAGACTACGAGAAACACAAAGTCTACGCCTGCGAAG
TCACCCATCAGGGCCTGAGCTCGCCCGTCACAAAGAGCTTCAACAGGGGA
GAGTGT-3'
(SEQ ID NO: 20)

IgG RW03 - Heavy chain (hG1) nucleotide sequence:

5'-GAGGTTCAGCTGGTGGAGTCTGGCGGTGGCCTGGTGCAGCCAGGGGG
CTCACTCCGTTTGTCCTGTGCAGCTTCT<u>GGCTTCAACCTCTCTTCTTCTT
CT</u><sub>CT</sub>ATC<sub>C</sub>CACTGGGTGCGTCAGGCCCCGGGTAAGGGCCTG
GAATGGGTTGCA<sub>TAT</sub>ATTTATCCTTATTATAGCTATAC
<sub>T</sub>TAT<sub>T</sub>TATGCCGATAGCGTCAAGGGCCGTTTCACTATAA
GCGCAGACACATCCAAAAACACAGCCTACCTACAAATGAACAGCTTAAGA
GCTGAGGACACTGCCGTCTATTATTGT<u>GCTCGCTTCGGTTCTGTTGCTGG
TTTTGACTAC</u>TGGGGTCAAGGAACCCTGGTCACCGTCTCCTCGGCTAGCA
CCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACC
GGTGACGGTGTCGTGGAACTCAGGCGCCCTGACCAGCGGCGTGCACACCT
TCCCGGCTGTCCTACAGTCCTCAGGACTCTACTCCCTCAGCAGCGTGGTG
ACCGTGCCCTCCAGCAGCTTGGGCACCCAGACCTACATCTGCAACGTGAA
TCACAAGCCCAGCAACACCAAGGTGGACAAGAAAGTTGAGCCCAAATCTT
GTGACAAAACTCACACATGCCCACCGTGCCCAGCACCTGAACTCCTGGGG
GGACCGTCAGTCTTCCTCTTCCCCCCAAAACCCAAGGACACCCTCATGAT
CTCCCGGACCCCTGAGGTCACATGCGTGGTGGTGGACGTGAGCCACGAAG
ACCCTGAGGTCAAGTTCAACTGGTACGTGGACGGCGTGGAGGTGCATAAT
GCCAAGACAAAGCCGCGGGAGGAGCAGTACAACAGCACGTACCGTGTGGT
CAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATC
TCCAAAGCCAAAGGGCAGCCCCGAGAACACAGGTGTACACCCTGCCCCC
ATCCCGGGAGGAGATGACCAAGAACCAGGTCAGCCTGACCTGCCTGGTCA
AAGGCTTCTATCCCAGCGACATCGCCGTGGAGTGGGAGAGCAATGGGCAG
CCGGAGAACAACTACAAGACCACGCCTCCCGTGCTGGACTCCGACGGCTC
CTTCTTCCTCTACAGCAAGCTCACCGTGGACAAGAGCAGGTGGCAGCAGG
GGAACGTCTTCTCATGCTCCGTGATGCATGAGGCTCTGCACAACCACTAC
ACGCAGAAGAGCCTCTCCCTGTCTCCGGGTAAA-3'
(SEQ ID NO: 21)

Underline identifies nucleotide sequences encoding CDR amino acid residues.
Large-font identifies nucleotide sequences encoding FR amino acid residues at positions 39, 55 and 66 randomized in the selection library used to identify antibody variable regions.
Italics identify nucleotide sequences encoding immunoglobulin constant region amino acid residues.

Figure 4A:
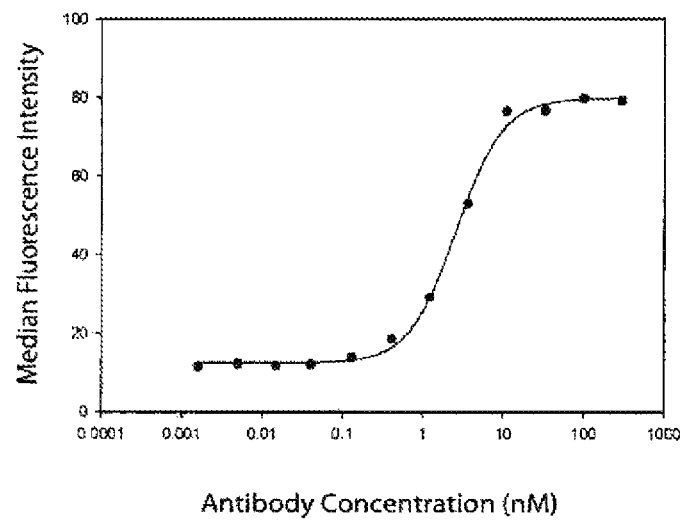
Figure 4B:
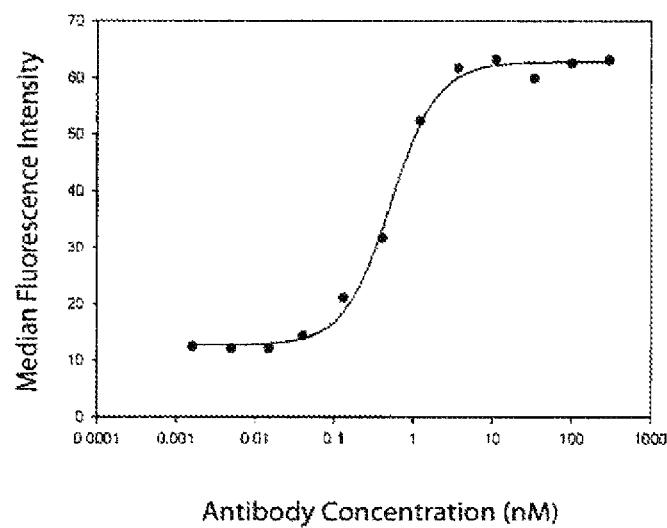

Example 3: IgG RW01 and IgG RW03 Bind CD133 Expressed at the Cell Surface with Approximately Single-Digit Nanomolar and Subnanomolar Affinity, Respectively The IgG RW01 and IgG RW03 antibodies were tested via flow cytometry for their capacity to bind HEK293-CD133 cells, after which half maximal binding concentrations of each antibody to the cells were estimated. Specifically, HEK293-CD133 cells were incubated with serial dilutions of each antibody, binding was detected with an anti-human Fab'2 secondary antibody and the data was fitted to a line of best fit using the Sigma Plot graphing program. FIG. 4 shows the EC50 curve for IgG RW01, which had a calculated EC50 of 2.5 nM and the curve for IgG RW03, which had a calculated EC50 of 0.5 nM.

Figure 5:
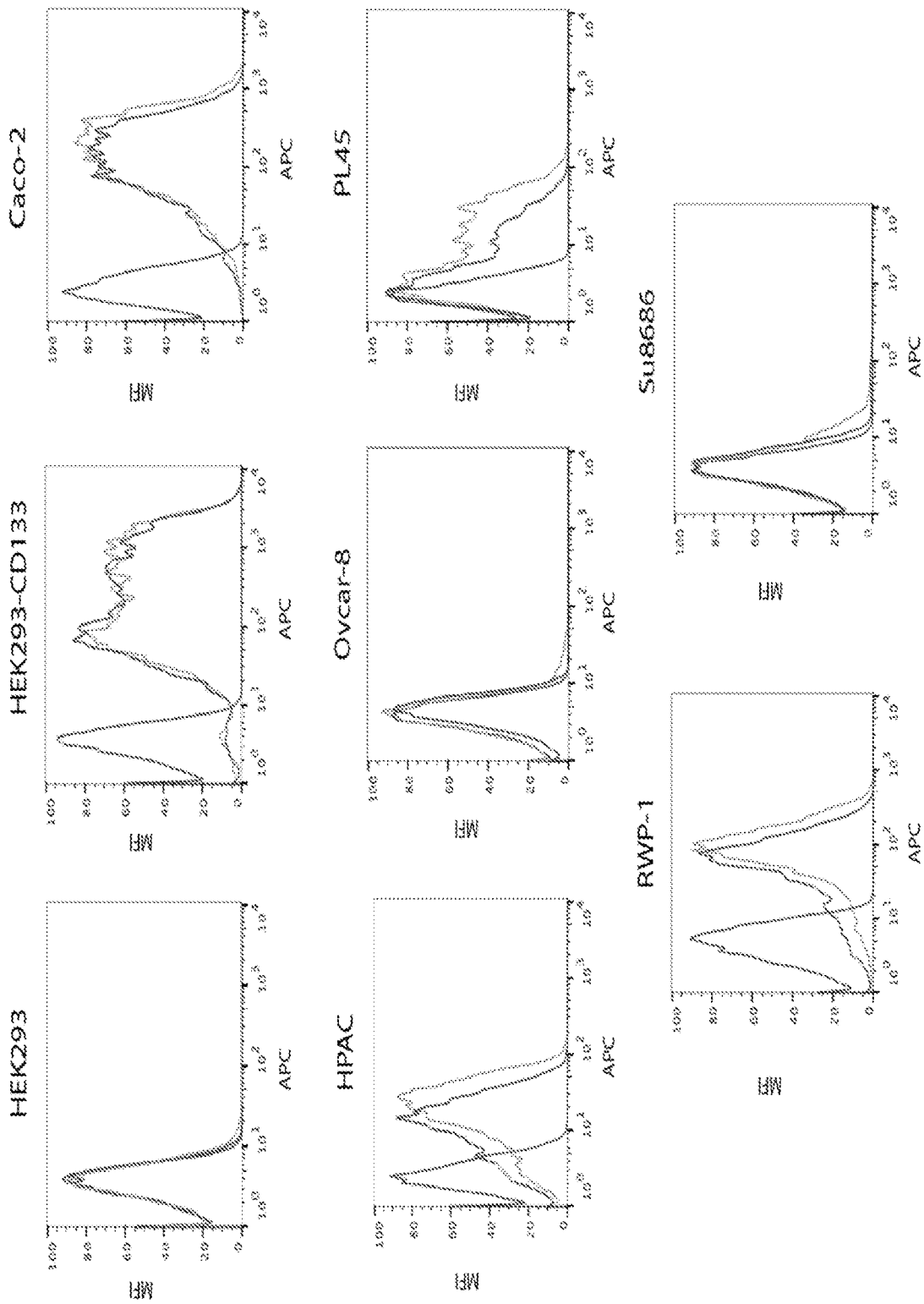
FIG. 5 is a set of fluorescence histograms depicting that IgG RW01 and IgG RW03 can be used to specifically bind and detect cell surface CD133 in pancreatic cancer cells and colorectal cancer cells, as shown via flow cytometry analysis.

Example 4: IgG RW01 and IgG RW03 can be Used to Specifically Bind and Detect Cell Surface CD133 in Pancreatic Cancer Cells and Colorectal Cancer Cells, as Shown Via Flow Cytometry Analysis The IgG RW01 and IgG RW03 antibodies were assessed via flow cytometry for binding to the following cancer cell lines: Caco-2, a colon cancer cell line known to express CD133; the pancreatic cancer cell lines HPAC, PL45, RWP-1 and SU8686; and the ovarian carcinoma cell line Ovcar-8. HEK293 and HEK293-CD133 cells were used as negative and positive controls, respectively. As shown in FIG. 5, both antibodies, at 5 µg/ml, bind CD133 at the surface of HEK293-CD133 control cells, at the surface of Caco-2 colorectal cancer cells and at the surface of HPAC, PL45 and RWP-1 pancreatic cancer cells. Bimodal staining peaks are observed in HPAC and PL45 cells and broader peaks such as those observed for the engineered cell line HEK293-CD133 are most likely a result of a heterogeneously expressing population of cells, contrasted with the narrow peak observed with RWP-1 cells indicating a more homogeneously expressing cell population.

Figure 6:
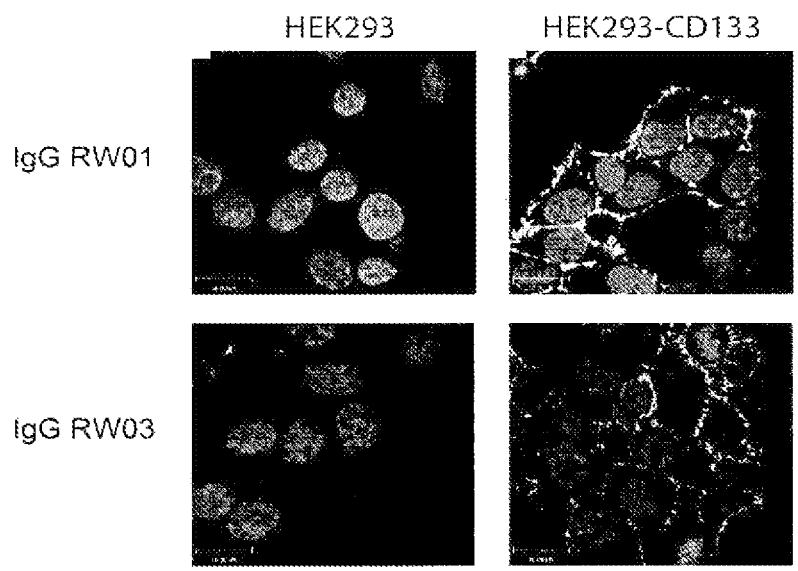
FIG. 6 is a set of fluorescence photomicrographs depicting that IgG RW01 and IgG RW03 can be used to specifically bind, detect and subcellularly localize cellular CD133, as shown via immunofluorescence analysis. The antibodies were tested for binding to HEK293-CD133 and HEK293 cells.

Example 5: IgG RW01 and IgG RW03 can be Used to Specifically Bind, Detect and Subcellularly Localize Cellular CD133, as Shown Via Immunofluorescence Analysis The IgG RW01 and IgG RW03 antibodies were tested for binding to cell-expressed CD133 in an immunofluorescence assay (FIG. 6). The assay shows that IgG RW01 and IgG RW03 bind to HEK293-CD133 cells (indicating cellular sublocalization of CD133), but not to HEK293 cells.

Example 6: IgG RW01 and IgG RW03 can Each be Used to Detect Denatured CD133 in Whole Cell Lysate of Colorectal Cancer Cells, as Shown Via Western Blot Analysis Whole cell lysates of Caco-2 colorectal cancer cells were prepared and the capacity of IgG RW01 and IgG RW03 to detect denatured CD133 in the lysate was analyzed via Western blotting assay. HEK293-CD133 cells and HEK293 cells were used as positive and negative controls, respectively. FIG. 7 shows that IgG RW01 and IgG RW03 each detect denatured CD133 in lysate of Caco-2 cells and HEK293-CD133 cells, which are both CD133-positive, but not in that of HEK293 cells.

Example 7: Epitopes—Fab RW01 and Fab RW03 do not Compete with IgG RW03 and IgG RW01, Respectively, for Binding to CD133

Experiments were performed to determine whether antibody variable region RW01 and antibody variable region RW03 compete with each other for binding to cell-expressed CD133. Cells were initially incubated with a 25 nM concentration of either Fab RW01 or Fab RW03, and serial dilutions of IgG RW03 or IgG RW01, respectively, were added, and the IgG binding was detected using a secondary antibody against human Fc. The results for each antibody can be seen in FIGS. 8 (*a*) and (*b*) and indicate that IgG RW01 can bind the cells in the presence of saturating RW03 Fab and IgG RW03 can bind in the presence of RW01 Fab.

Example 8: Treatment with IgG RW01 or IgG RW03 can be Used to Significantly Reduce Total Cellular CD133 Protein Levels in Caco-2 Colorectal Cancer Cells To investigate the effect of IgG RW01 and IgG RW03 on CD133 protein levels in cancer cells, Caco-2 colorectal cancer cells were incubated with either IgG RW01 or IgG RW03 for 24 hours at 37° C., and whole cell lysates were analyzed by Western blot using AC133 anti-CD133 antibody (Miltenyi Biotec) as probe and anti-human IgG (H+L) antibody (Jackson ImmunoResearch) as negative antibody control. As FIG. 9 shows, treatment with RW01 IgG or RW03 IgG significantly reduced CD133 protein levels, as compared to the untreated and anti-human IgG control treatments. To assess the effect of the observed reduction in CD133 protein levels on Wnt signaling in the cells, β-catenin levels were also analyzed, however there were no observed differences on β-catenin protein stability between control antibody-treated and IgG RW01- or IgG RW03-treated samples.

Example 9: Single-Chain Fab RW03 can be Used for Targeting Bispecific T Cell Engagers (BiTEs) to CD133-Positive Cells Vectors were constructed for expression of four novel anti-CD133×anti-CD3 bi-specific T-cell engagers (BiTEs; FIG. 10A). Each of the four BiTEs incorporates an anti-CD3 scFv, and further incorporates either anti-CD133 Fab RW03 (Fab-based BiTEs) or an anti-CD133 single-chain Fab (scFab) incorporating the variable regions of Fab RW03 ("scFab RW03"; scFab-based BiTEs). In each of the 4 BiTEs, the Fab or scFab is linked to the VH domain of the scFv. The 4 BiTEs include two Fab-based variants, in which the scFv is linked either to the light chain ("BiTE #1") or heavy chain-derived portion ("BiTE #2") of the Fab. The other two BiTEs are scFab-based variants, in which the scFv is similarly linked either to the heavy chain-derived segment ("BiTE #3") or light chain segment ("BiTE #4") of the scFab.

The amino acid sequences of BiTE #1, BiTE #2, BiTE #3 and BiTE #4 are shown in Table 6.

TABLE 6

Configurations and amino acid sequences of BiTE #1, BiTE #2, BiTE #3 and BiTE #4 polypeptides.

BiTE #1
Configuration:
VL-CL (RW03)-(G4S)-VH-(G4S)3-VL (CD3)
VH-CH (RW03)
Amino acid sequence of VL-CL (RW03)-(G4S)-VH-(G4S)3-VL:

DIQMTQSPSSLSASVGDRVTITCRASQSVSSAVAWYQQKPGKAPKLLIYS
ASSLYSGVPSRFSGSRSGTDFTLTISSLQPEDFATYYCQQYSHAGHLFTF
GQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTH

TABLE 6-continued

Configurations and amino acid sequences of BiTE
1, BiTE #2, BiTE #3 and BiTE #4 polypeptides.

QGLSSPVTKSFNRGECGGGGSDIKLQQSGAELARPGASVKMSCKTSGYTF
TRYTMHWVKQRPGQGLEWIGYINPSRGYTNYNQKFKDKATLTTDKSSSTA
YMQLSSLTSEDSAVYYCARYYDDHYCLDYWGQGTTLTVSS**GGGGSGGGGS
GGGGS**DIQLTQSPAIMSASPGEKVTMTCRASSSVSYMNWYQQKSGTSPKR
WIYDTSKVASGVPYRFSGSGSGTSYSLTISSMEAEDAATYYCQQWSSNPL
TFGAGTKLELK
(SEQ ID NO: 22)

Amino acid sequence of VH-CH (RW03):

EVQLVESGGGLVQPGGSLRLSCAASGFN<u>LSSSSI</u>HWVRQAPGKGLEWVA<u>Y
IYPYYSYTY</u>YADSVKGRFTISADTSKNTAYLQMNSLRAEDTAVYYCAR<u>FG
SVAGFD</u>YWGQGTLVTV*SSASTKGPSVFPLAPSSKSTSGGTAALGCLVKDY
FPEPVTVSWNSGALTSGVHTFPAVIQSSGLYSLSSVVTVPSSSLGTQTYI
CNVNHKPSNTKVDKKVEPKSCDKTHT*
(SEQ ID NO: 23)

BiTE #2
Configuration:
VH-CH (RW03)-(G4S)-VH-(G4S)3-VL (CD3)
VL-CL (RW03)
Amino acid sequence of VH-CH (RW03)-(G4S)-VH-(G4S)3-VL (CD3):

EVQLVESGGGLVQPGGSLRLSCAASGFN<u>LSSSSI</u>HWVRQAPGKGLEWVA<u>Y
IYPYYSYTY</u>YADSVKGRFTISADTSKNTAYLQMNSLRAEDTAVYYCAR<u>FG
SVAGFD</u>YWGQGTLVTV*SSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHT*GGGGSDIKLQQSGAELARPGASVK
MSCKTSGYTFTRYTMHWVKQRPGQGLEWIGYINPSRGYTNYNQKFKDKAT
LTTDKSSSTAYMQLSSLTSEDSAVYYCARYYDDHYCLDYWGQGTTLVSS
GGGGSGGGGSGGGGSDIQLTQSPAIMSASPGEKVTMTCRASSSVSYMNWY
QQKSGTSPKRWIYDTSKVASGVPYRESGSGSGTSYSLTISSMEAEDAATY
YCQQWSSNPLTFGAGTKLELK
(SEQ ID NO: 24)

Amino acid sequence of VL-CL (RW03):

DIQMTQSPSSLSASVGDRVTITCRASQ<u>SVSSA</u>VAWYQQKPGKAPKLLIY<u>S
ASSLYS</u>GVPSRESGSRSGTDFTLTISSLQPEDFATYYCQQ<u>YSHAGHLFTF
G</u>GGTKVEIKRT*VAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC*
(SEQ ID NO: 25)

BiTE #3
Configuration:
VL-CL-linker-VH-CH (RW03)-(G4S)-VH-(G4S)3-VL (CD3)
Amino acid sequence:

DIQMTQSPSSLSASVGDRVTITCRASQ<u>SVSSA</u>VAWYQQKPGKAPKLLIY<u>S
ASSLYS</u>GVPSRESGSRSGTDFTLTISSLQPEDFATYYCQQ<u>YSHAGHLFTF
G</u>GGTKVEIKRT*VAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC***GGSSGSGSGTGTSSSGTGTSAGTTGTSASTSGS
GSG**EVQLVESGGGLVQPGGSLRLSCAASGFN<u>LSSSSI</u>HWVRQAPGKGLEW
VA<u>YIYPYYSYTY</u>YADSVKGRFTISADTSKNTAYLQMNSLRAEDTAVYYCA
R<u>FGSVAGFD</u>YWGQGTLVTV*SSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHT*GGGGSDIKLQQSGAELARPGA
SVKMSCKTSGYTETRYTMHWVKQRPGQGLEWIGYINPSRGYTNYNQKFKD
KATLTTDKSSSTAYMQLSSLTSEDSAVYYCARYYDDHYCLDYWGQGTTL
VSSGGGGSGGGGSGGGGSDIQLTQSPAIMSASPGEKVTMTCRASSSVSYM
NWYQQKSGTSPKRWIYDTSKVASGVPYRESGSGSGTSYSLTISSMEAEDA
ATYYCQQWSSNPLTFGAGTKLELK
(SEQ ID NO: 26)

BiTE #4
Configuration:
VH-CH-linker-VL-CL (RW03)-(G4S)-VH-(G4S)3-VL (CD3)
Amino acid sequence:

EVQLVESGGGLVQPGGSLRLSCAASGFN<u>LSSSSI</u>HWVRQAPGKGLEWVA<u>Y
IYPYYSYTY</u>YADSVKGRFTISADTSKNTAYLQMNSLRAEDTAVYYCAR<u>F
GSVAGFD</u>YWGQGTLVTV*SSASTKGPSVFPLAPSSKSTSGGTAALGCLVKD

TABLE 6-continued

Configurations and amino acid sequences of BiTE
1, BiTE #2, BiTE #3 and BiTE #4 polypeptides.

YFPEPVTVSWNSGALTSGVHTFPAVLQSSGLYSLSSVVTVPSSSLGTQTY
ICNVNHKPSNTKVDKKVEPKSCDKTHT***GGSSGSGSGSTGTSSSGTGTSAG
TTGTSASTSGSGSG**DIQMTQSPSSLSASVGDRVTITCRASQ<u>SVSSA</u>VAWY
QQKPGKAPKLLIY<u>SASSLYS</u>GVPSRFSGSRSGTDFTLTISSLQPEDFATY
YCQQ<u>YSHAGHLFT</u>FGQGTKVEIKRT*VAAPSVFIFPPSDEQLKSGTASVVC
LLNNFYPREAKVQWKVDNALQSGNSQESVTEQDSKDSTYSLSSTLTLSKA
DYEKHKVYACEVTHQGLSSPVTKSFNRGEC*GGGGSDIKLQQSGAELARPG
ASVKMSCKTSGYTFTRYTMHWVKQRPGQGLEWIGYINPSRGYTNYNQKFK
DKATLTTDKSSSTAYMQLSSLTSEDSAVYYCARYYDDHYCLDYWGQGTTL
TVSSGGGGSGGGGSGGGGSDIQLTQSPAIMSASPGEKVTMTCRASSSVSY
MNWYQQKSGTSPKRWIYDTSKVASGVPYRFSGSGSGTSYSLTISSMEAED
AATYYCQQWSSNPLTFGAGTKLELK
(SEQ ID NO: 27)

Underline identifies CDR sequence.
Italics represent immunoglobulin constant region amino acids.
Linker amino acids indicated in bold HEK293 cells transiently transfected with the BiTE-expression vectors were capable of readily expressing BiTE #1, BiTE #2, BiTE #3 and BiTE #4 expressed and purified from, as shown via Western blot analysis of reduced and non-reduced whole cell lysates of transfectants (FIG. 10B).

BiTE #1, BiTE #2, BiTE #3 and BiTE #4 have the Capacity to Bind to Cell Surface CD133 and CD3

The capacity of the purified BiTEs to specifically bind cell surface CD133 was determined using flow cytometry analysis of staining of HEK293-CD133 cells vs HEK293 cells with the BiTEs. As shown in FIG. 11A and FIG. 11B, BiTE #1, BiTE #2, BiTE #3 and BiTE #4 each binds to HEK293-CD133 cells significantly more than to HEK293 cells, even at concentrations as low as 0.073-0.11 microgram/ml. The purified BiTEs were further tested in an ELISA to determine their capacity to bind to CD3 in the form of CD3 epsilon/gamma and CD3 epsilon/delta. As shown in FIG. 12, the purified BiTEs bind to CD3 as well as the positive control antibodies (UCHT1, OKT3). These BiTEs can bind to both CD133 and CD3.

Example 10: Human CD133-Specific Chimeric Antigen Receptor (CAR) Modified T Cells Target Patient-Derived Glioblastoma Brain Tumors A single chain variable fragment (scFv) was derived from RW03 (described above) and a second-generation CAR was generated. Anti-CD133 scFv with a myc tag was cloned in frame with a human CD8 leader sequence, CD8a transmembrane domain, CD28, and hCD3 (human CD3zeta) signaling tail in the lentiviral construct pCCL-ΔNGFR vector in two different orientations: Light chain-linker-Heavy chain (CD133 CAR-LH) and Heavy chain-linker-Light chain (CD133 CAR-HL).

Following lentiviral preparation, T cells isolated from PBMCs were transduced with CD133 CAR-LH and CD133 CAR-VH constructs. After successful T cell engineering, the expression of ΔNGFR and myc tag was analyzed using flow cytometry to confirm the efficiency of transduction and surface expression of anti-CD133 respectively. While expression of ΔNGFR was observed in all CAR T cells (including controls), expression of the c-myc tag in both variations of CARs, CD133 CAR-HL and CD133 CAR-LH was found. Furthermore, Presto Blue-based killing assays were used to test the ability of CD133 CARs to selectively bind and kill CD133+ GBM brain tumor initiating cell lines (BTICs). CD133-specific CAR-T cells were cytotoxic to CD133+ GBMs. Co-culturing CD133 CAR-T cells with GBMs triggered T cell activation and proliferation, validating this adoptive T-cell therapeutic strategy.

Human T cells expressing CD133-specific CARs were engineered by cloning scFv comprising the heavy and light chain variable domains of antibody variable region RW03 (disclosed above), a short marker epitope of c-myc, the hinge region from murine CD8 and the transmembrane and cytoplasmic portions of murine CD28 and CD3, (FIG. 13). The human CD133-CAR was cloned into the lentiviral transfer vector pCCL-ΔNGFR and packaged as lentiviruses. The c-myc tag in the extracellular domain was used to validate CAR expression. ΔNGFR was used as a cell-surface marker for tracking and sorting of transduced cells.

Transduced T cells consisted of CD4-positive and CD8-positive cells with both subsets expressing CD133-specific CARs (FIG. 14). After successful transduction, the expression of ΔNGFR (CD271) was observed in all CAR T cells (including controls), however increased expression of the c-myc tag was found in the CD133 CAR-HL and CD133 CAR-LH cells only (FIG. 15).

CD133-specific CAR-T cells were incubated with GBM BT459, stained and analyzed for surface expression of T cell activation markers CD69 and CD25 after 18 hours (FIG. 16). Both, CD4+(T-helper) and CD8+(T-cytotoxic) cells showed upregulation in surface expression levels of activation markers. The elevated expression was detected only in the presence of CD133-specific CAR and not CAR-T control.

CD133-specific CAR T-cells showed enhanced proliferation capability after being co-cultured with CD133$^{high}$ GBM cells (FIG. 17, top row). CD133-specific CAR T cells specifically recognized and kill tumor cells in CD133$^{high}$ GBMs and medulloblastoma (Control), while having no effect on CD133$^{low}$ GBM cells (FIG. 17, bottom row). CD133$^{high}$ and CD133$^{low}$ GBMs were defined based on the percentage of CD133-positive cells present in the tumor cell culture. GBM cultures with >90% CD133+ cells were defined as CD133$^{high}$ GBMs and cultures with <5% CD133+ cells were defined as CD133$^{low}$ GBMs.

Tumor-engrafted mice were injected i.e. with CAR-CON (control) T cells (FIG. 18A) and with CAR-CD133 T cells at an effector to target ratio (E:T)=2:1 (FIG. 18B). Tumors formed in mouse brain intracranially treated with CAR-CD133 T cells were significantly less aggressive and invasive compared to control (as assessed by COX IV staining for human cells) (n=4). Mouse xenografts generated after CAR-CD133 T cell treatment had significant less tumor mass (FIG. 18C).

Treatment of GBM tumor-bearing mice with CD133-specific CAR-T cells yielded extended survival in mice and significant reductions in brain tumor burden.

Example 11. Preclinical Validation of a Novel CD133/CD3 Bispecific T-Cell Engager (BiTE) Antibody to Target Patient-Derived Glioblastoma Cells The BiTE format has been evaluated against a variety of tumor-associated antigens, including CD19, CD20, EpCAM, EGFR, MUC-1, CEA, CD133, EphA2 and HER2/neu (reviewed in Baeuerle et al. 2009). Clinical trials investigating BiTEs include Blinatumomab for leukemia patients (NCT00274742), AMG110/MT110 for lung/colorectal/breast/ovarian cancer patients (NCT00635596), AMG211/MED1565 for gastrointestinal adenocarcinoma patients (NCT01284231) and AMG212/BAY2010112 for prostate cancer patients (NCT0173475). BiTEs exhibiting specificity for two GBM tumor cell surface antigens CD133 (Prasad et al, 2015) and EGFRvIII (Choi et al, 2013) have also been shown to be induce anti-tumorigenic activity in xenograft tumor models. Importantly, preclinical evaluation of EGFRvIII-specific BiTEs delivered intravenously showed tumor reduction/shrinkage, extending survival in mice with well-established EGFRvIII-expressing GBM.

As described in Example 9, CD133-specific BiTEs or RW03×CD3 were constructed that consist of two arms; one arm recognizes the tumor antigen (CD133) while the second is specific to CD3 antigen. The BiTEs were constructed in four different conformations and dual binding specificity was confirmed using flow cytometry. Using CD133$^{high}$ and CD133$^{low}$ primary GBM lines, the binding of BiTEs to CD133+ cells was validated. Further analysis showed binding of BiTEs to human T cells known to express CD3 within a population of healthy donor peripheral blood mononuclear cells. BiTEs redirecting T cells to kill GBMs were observed, with greater efficiency observed in CD133$^{high}$ GBMs, validating BiTE target specificity.

Specifically, using CellectSeq, a novel methodology that combines use of phage-displayed synthetic antibody libraries and high-throughput DNA sequencing technology, CD133-specific monoclonal antibody 'RW03' was developed (FIG. 19A). Following validation of CD133 RW03 antibody, CD133-specific BiTEs or RW03×CD3 was constructed that had two arms; one arm recognizes the tumor antigen (CD133) while the second is specific to CD3 antigen. The BiTEs were constructed in four different conformations (FIG. 19B).

Figure 20B:
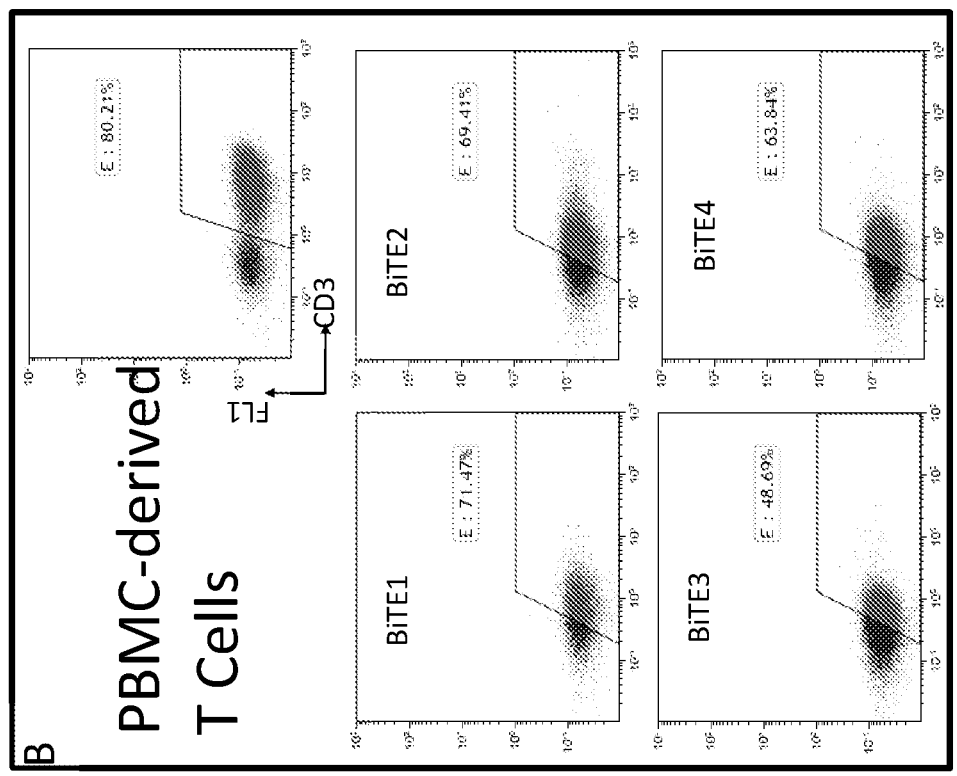

Flow cytometry was used to confirm dual specificity of CD133×CD3 BiTEs against cells expressing the appropriate antigen. CD133×CD3 BiTEs bind to GBM tumor expressing CD133 in similar capacity when compared with binding to commercially available CD133 (Miltenyi) monoclonal antibody (FIG. 20A). Analyses revealed binding of CD133×CD3 BiTEs to human T cells known to express CD3 within a population of healthy donor peripheral blood mononuclear cells (PBMCs) (FIG. 20B).

T cells incubated with BiTEs and CD133$^{high}$ GBM BT459 were stained and analyzed for surface expression of activation markers CD69 and CD25 (FIG. 21). Both, CD4+(T-helper) and CD8+(T-cytotoxic) cells showed upregulation in surface expression levels of the activation markers. The elevated expression was detected only in the presence of CD133 BiTE in the co-culture.

GBM cells form a monolayer when plated alone (FIG. 22A(a) or plated with T cells (FIG. 22A(b)); however, addition of BiTEs (FIG. 22A, c and d) recruits T cells to GBM cells forming spherical clusters. Addition of BiTEs to GBM cells co-cultured with T cells leads to significant cell death of GBM cells as determined through alamar-blue cytotoxicity assay (FIG. 22B). Quantification of tumor cell lysis by flow cytometry-based Live-Dead staining (with IR dye) (FIG. 22C). Tumor cells (CFSE-labeled) and T cells (E:T ratio, 1:2) in presence and absence of CD133 BiTEs after 24 hours show BiTE-mediated GBM cell death.

Figure 23:
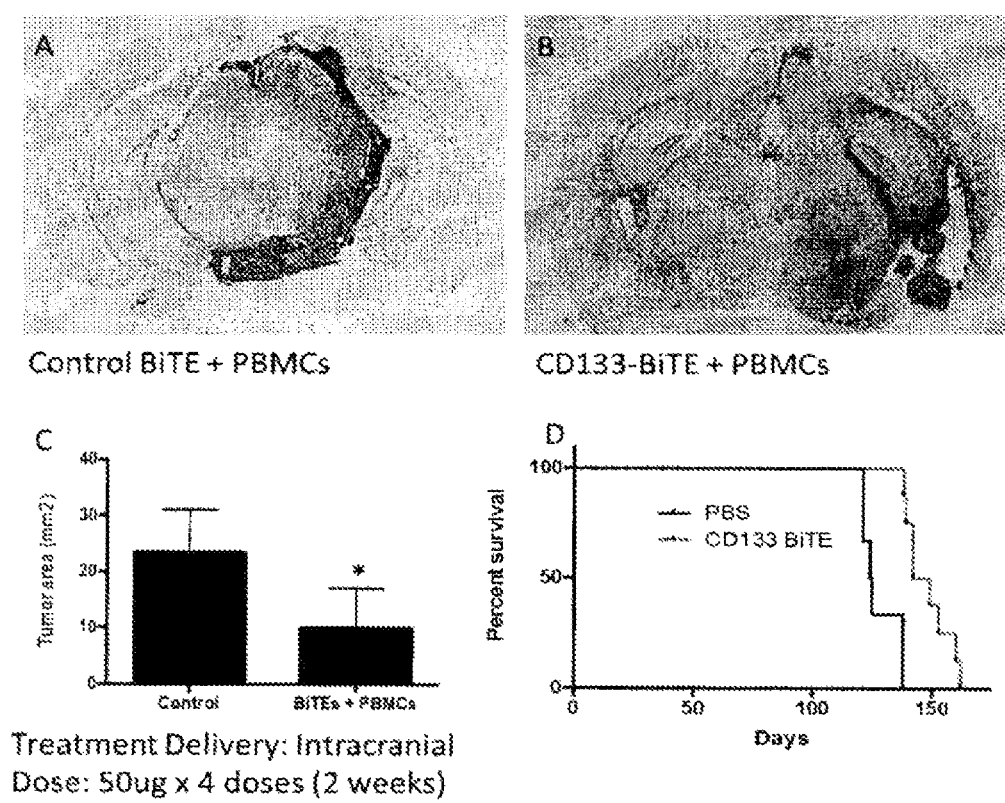

NSG (NOD scid gamma) mice were implanted i.c. with CD133$^{high}$ GBM cells and upon successful engraftment, were treated with unstimulated PBMCs with or without BiTEs (Total 4 doses over 2 weeks) (FIG. 23). Tumors formed in mouse brain intracranially treated with CD133 BiTEs were significantly less aggressive and invasive compared to control (as assessed by COX IV staining for human cells) (n=4) (FIGS. 23, A and B)). Mouse xenografts generated after BiTE treatment had less tumor burden (FIG.

23C) and maintained a significant survival advantage over control mice (n=7) (FIG. 23D).

Methods for Examples 10 and 11

Flow Cytometric Characterization:

Patient-derived GBM lines were dissociated and single cells resuspended in PBS+2 mM EDTA. Cell suspensions were stained with anti-CD133, anti-CD69, anti-CD25, anti-CD8, anti-CD4 or matched isotype controls (Miltenyi/BD Biosciences). Samples were run on a MoFlo XDP Cell Sorter (Beckman Coulter). Dead cells were excluded using the viability dye 7AAD. (1:10; Beckman Coulter). Compensation was performed using mouse IgG CompBeads (BD). Surface marker expression was defined as positive or negative based on the analysis regions established using the isotype control.

Cell Proliferation Assay:

Single cells were plated in a 96-well plate at a density of 1,000 cells/200 µL per well in quadruplicate and incubated for four days. 20 µL of Presto Blue (Invitrogen) was added to each well approximately 2 h prior to the readout time point. Fluorescence was measured using a FLUOstar Omega Fluorescence 556 Microplate reader (BMG LABTECH) at excitation and emission wavelengths of 535 nm and 600 nm, respectively. Readings were analyzed using Omega analysis software.

Quantitative Cytotoxicity Assays:

Prestoblue killing and LDH cytotoxicity assays with different effector/target (E:T) ratios was performed to determine the efficiency of BiTEs to redirect T cells and kill CD133-expressing GBM BTICs.

In Vivo GBM Intracranial Injections and H&E Staining of Xenograft Tumors:

All experimental procedures involving animals were reviewed and approved by McMaster University Animal Research Ethics Board (AREB). NOD-SCID mice were used for all experiments. Mice were anaesthesized using gas anaesthesia (Isoflurane: 5% induction, 2.5% maintenance) identified using ear notches following minimally invasive surgery, and monitored for recovery. Intracranial injections were performed as previously described (1). Briefly, 10 µL of cell suspension was injected into the right frontal lobe of 8-10 week old mice. Mice were monitored weekly for signs of illness, and upon reaching endpoint, brains and lungs (for IT and ICa injections) were harvested, sectioned, and paraffin-embedded for hematoxylin and eosin (H&E). Images were scanned using an Aperio Slide Scanner and analyzed by ImageScope v11.1.2.760 software (Aperio).

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety.

REFERENCES

Abate-Daga and Davila, 2016. Mol Ther Oncolytics. 18:16014
Altschul et al., 1990. J. Mol. Biol. 215:403
Altschul et al., 1997. Nucleic Acids Res. 25:3389-3402
Baeuerle et al., 2009. Current opinion in molecular therapeutics. 11:22-30
Bauer et al., 2008. Organs 188:127
Bao et al, 2006. Nature 444:756
Boman et al., 2008. J. Clin. Oncol. 26:2795
Brown et al., 2016. N Engl J Med. 375:2561
Caron et al., 1992. J Exp Med., 176:1191-1195
Choi, et al., 2013 Cancer immunology research. 1:163
Cole et al., 1985. *Monoclonal Antibodies and Cancer Therapy*, Alan R. Liss, Inc., pp. 77-96
Collins, 2005. Cancer research 65:10946 Cote, et al., 1983. Proc Natl Acad Sci USA 80:2026-2030
Cruse and Lewis, 1989. *Conjugate Vaccines, Contributions to Microbiology and Immunology*, J. M. Cruse and R. E. Lewis, Jr (eds), Carger Press, New York Davies et al., 1990. Annual Rev Biochem 59:439-473
Evangelista et al., 2006. Clin. Cancer Res. 12:5924
Evans et al., 1987. J. Med. Chem. 30:1229
Fauchere, 1986. J. Adv. Drug Res. 15:29 Ferrandina et al., 2009. Expert Opin. Ther. Targets, 13:823Green et al., 1994. Nature Genetics 7:13-21
Green and Sambrook, 2012. *Molecular Cloning: A Laboratory Manual* (4th ed., Cold Spring Harbor Laboratory Press, Cold Spring Harbor, N.Y.)
Greenfield, 2013. *Antibodies: A Laboratory Manual* (Cold Spring Harbor Laboratory Press, Cold Spring Harbor, N.Y.)
Gruber et al., 1994. J. Immunol. 152:5368
Hermann et al., 2007. Cell Stem Cell, 1:313-323
Hollinger et al., 1993. Proc. Natl. Acad. Sci. USA 90:6444-6448
Horst et al., 2009. The Journal of Pathology 219:427 Huse, et al., 1989 Science 246:1275-1281
Kabat et al., 1991. *Sequences of Proteins of Immunological Interest*, 5th Ed. Public Health Service, National Institutes of Health, Bethesda, Md.
Karlin and Altschul, 1990. Proc. Natl. Acad. Sci. U.S.A. 87:2264-2268
Karlin and Altschul, 1993. Proc. Natl. Acad. Sci. U.S.A. 90:5873-5877
Kohler and Milstein, 1975. Nature 256:495 Kostelny et al., 1992. J. Immunol 148(5):1547-1553
Kozbor et al., 1983. Immunol Today 4:72
Lam, 1997. Anticancer Drug Design 12:145
Lefranc et al. 2003. Development and Comparative Immunology 27:55-77
Liu et al., 1987a. Proc. Natl. Acad. Sci. U.S.A. 84:3439
Liu et al., 1987b. J. Immunol. 139:3521
Lugli et al., 2010. British journal of cancer 103:382
Mak et al., 2012a. Cell. Rep. 2:951
Mak et al., 2012b. Cancer research 72:1929
Malmqvist M, 1993. Nature 361:186-87
Maus and June, 2016. Clin Cancer Res. 22:1875-84
McEnaney et al., 2014. J Am Chem Soc. 136:18034
Miki et al., 2007. Cancer research 67:3153
Missol-Kolka et al., 2010. The Prostate 71:254 Moriyama et al., 2010. Cancer 116:3357
Morrison, 1994. Nature 368, 812-13
Myers and Miller, 1988. CABIOS 4:11-17
O'Brien et al., 2006. Nature 445:106
Parashar, 2016. Aptamers in Therapeutics. J Clin Diagn Res. 10:BE01
Pfeiffer and Schalken, 2010. European Urology 57:246
Prasad et al., 2015. Cancer research. 75:2166-76
Rappa et al., 2008. Stem Cells 26:3008
Resetca et al., 2016. J Immunother. 39:249-59
Reverdatto et al., 2015. Curr Top Med Chem. 15:1082

Ricci-Vitiani et al., 2006. Nature: 445:111
Rizo and Gierasch, 1992. Ann. Rev. Biochem. 61:387
Schmohl and Vallera, 2016. Toxins (Basel) 8:165
Shmelkov, 2004. Blood 103:2055
Shopes, 1992. J. Immunol. 148:2918-2922
Singh et al., 2003. Cancer Res. 63:5821-8
Singh et al, 2004. Nature 432:396-401
Smith et al., 2008. British journal of cancer 99:100
Stevenson et al., 1989. Anti-Cancer Drug Design, 3:219-230
Takenobu et al., 2011. Oncogene 30:97
Traunecker et al., 1991. EMBO 10:3655
Tutt et al., 1991. J. Immunol. 147:60
Ulasov et al., 2011. Mol. Med. 17:103
Veber and Freidinger, 1985. TINS p. 392
Venugopal et al., 2015. Clinical cancer research: an official journal of the American Association for Cancer Research. 21:5324-37
Vincke C, et al., 2008. J Biol. Chem. 284:3273.
Wang and Riviere, 2016. Mol Ther Oncolytics 3:16015
Wei et al., 2007 Cancer biology & therapy 6:763
Wilkinson D, 2000. The Scientist 14:25-28
Winter and Harris, 1993. Immunol Today 14:43
Wright et al., 1992. Crit. Reviews in Immunol. 12:125-168
Zhong et al., 2015. Tumor Biol. 36:7623

The invention claimed is:

1. An antibody or an antigen binding fragment thereof that specifically binds to a CD133 polypeptide, wherein said antibody or antigen binding fragment thereof comprises a light chain variable domain comprising complementarity determining regions (CDRs) comprising SEQ ID NOs: 12, 13, and 14 and a heavy chain variable domain comprising CDRs comprising SEQ ID NOs: 15, 16, and 17.

2. The antibody or antigen binding fragment thereof according to claim 1, wherein said antibody is a single chain variable fragment (scFv) antibody or a single chain Fab fragment (scFab) antibody.

3. The antibody or antigen binding fragment thereof according to claim 1, wherein said antigen binding fragment is selected from a Fab fragment, a Fab' fragment, and an Fv fragment.

4. The antibody or antigen binding fragment thereof according to claim 1, wherein said antibody is a humanized antibody or a chimeric antibody.

5. The antibody or antigen binding fragment thereof according to claim 1, wherein the light chain variable domain comprises an amino acid sequence that is at least 70% identical to SEQ ID NO: 30 and/or wherein the heavy chain variable domain comprises an amino acid sequence that is at least 70% identical to SEQ ID NO: 31.

6. The antibody or antigen binding fragment thereof according to claim 1, wherein the light chain variable domain comprises the amino acid sequence of SEQ ID NO: 30 and/or wherein the heavy chain variable domain comprises the amino acid sequence of SEQ ID NO: 31.

7. The antibody or antigen binding fragment thereof according to claim 1, wherein the CD133 polypeptide is a human CD133 polypeptide.

8. The antibody or antigen binding fragment thereof according to claim 7, wherein the human CD133 polypeptide comprises SEQ ID NO: 1.

9. The antibody or antigen binding fragment thereof according to claim 1, wherein the CD133 polypeptide is denatured.

10. The antibody or antigen binding fragment thereof according to claim 1, wherein the CD133 polypeptide is on the surface of a cell.

11. The antibody or antigen binding fragment thereof according to claim 1, wherein said antibody or antigen binding fragment thereof comprises human constant regions.

12. The antibody or antigen binding fragment thereof according to claim 1, wherein said antibody is an IgG antibody.

13. The antibody or antigen binding fragment thereof according to claim 1, wherein said antibody is an IgA1, IgA2, IgD, IgG1, IgG2, IgG3, IgG4, IgE or IgM antibody.

14. The antibody or antigen binding fragment thereof according to claim 1, wherein said antibody is a bispecific antibody.

15. The antibody or antigen binding fragment thereof according to claim 14, wherein said bispecific antibody binds to a CD3 polypeptide.

16. The antibody or antigen binding fragment thereof according to claim 14, wherein said bispecific antibody comprises:
   (a) a polypeptide comprising SEQ ID NO: 22 and a polypeptide comprising SEQ ID NO: 23;
   (b) a polypeptide comprising SEQ ID NO: 24 and a polypeptide comprising SEQ ID NO: 25;
   (c) a polypeptide comprising SEQ ID NO: 26; or
   (d) a polypeptide comprising SEQ ID NO: 27.

17. A chimeric antigen receptor (CAR) that specifically binds to a CD133 polypeptide, wherein said CAR comprises an extracellular antigen binding domain comprising the antibody or antigen binding fragment thereof according to claim 1.

18. The antibody or antigen binding fragment thereof according to claim 1, wherein said antibody or antigen binding fragment thereof is detectably labeled.

19. An immunoconjugate comprising the antibody or antigen binding fragment thereof according to claim 1 and an effector agent.

20. The immunoconjugate according to claim 19, wherein said effector agent is an anti-neoplastic agent or a toxin.

21. A pharmaceutical composition comprising the antibody or antigen binding fragment thereof according to claim 1 and a carrier.

22. A method for treating cancer expressing CD133 in a subject, said method comprising administering to the subject an effective amount of the antibody or antigen binding fragment thereof according to claim 1.

23. The method according to claim 22, wherein said cancer is selected from a metastatic melanoma, a brain cancer, a prostate cancer, a pancreatic cancer, and a colon cancer.

24. The method according to claim 23, wherein said brain cancer is a glioblastoma or a medulloblastoma.

25. A method for treating cancer expressing CD133 in a subject, said method comprising administering to the subject an effective amount of the bispecific antibody according to claim 15.

26. A method for treating cancer expressing CD133 in a subject, said method comprising administering to the subject an effective amount of T cells expressing a CAR according to claim 17.

27. A method for detecting CD133 and/or quantifying the levels of CD133 expressed by cells, said method comprising contacting a sample suspected of comprising CD133 or cells expressing CD133 with the antibody or antigen binding fragment thereof according to claim 1.

* * * * *